(12) United States Patent
Liu et al.

(10) Patent No.: US 9,346,791 B2
(45) Date of Patent: May 24, 2016

(54) ITRACONAZOLE ANALOGS AND USE THEREOF

(75) Inventors: Jun O. Liu, Clarksville, MD (US); Wei Shi, Fayetteville, AR (US); Kalyan Kumar Pasunooti, Singapore (SG)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/343,040

(22) PCT Filed: Sep. 7, 2012

(86) PCT No.: PCT/US2012/054306
§ 371 (c)(1),
(2), (4) Date: Apr. 10, 2014

(87) PCT Pub. No.: WO2013/036866
PCT Pub. Date: Mar. 14, 2013

(65) Prior Publication Data
US 2014/0221393 A1    Aug. 7, 2014

Related U.S. Application Data

(60) Provisional application No. 61/531,819, filed on Sep. 7, 2011.

(51) Int. Cl.
*C07D 405/14* (2006.01)
*A61K 31/496* (2006.01)
*A61K 31/506* (2006.01)

(52) U.S. Cl.
CPC ............ *C07D 405/14* (2013.01); *A61K 31/496* (2013.01); *A61K 31/506* (2013.01)

(58) Field of Classification Search
None
See application file for complete search history.

(56) References Cited

U.S. PATENT DOCUMENTS 6,384,030 B1    5/2002    Meerpoel et al.

FOREIGN PATENT DOCUMENTS

CN    102234267    * 11/2011
WO    WO 94/16700 A1    8/1994

OTHER PUBLICATIONS

Machine English translation for CN 102234267 (Nov. 9, 2011).*
Yang et al. Chemical Abstracts vol. 155, No. 657037 (2011) (Abstract for CN 102234267).*

* cited by examiner

*Primary Examiner* — Emily Bernhardt
(74) *Attorney, Agent, or Firm* — DLA Piper LLP (US)

(57) ABSTRACT

Provided herein are Itraconazole analogs. Also provided herein are methods of inhibition of Hedgehog pathway, vascular endothelial growth factor receptor 2 (VEGFR2) glycosylation, angiogenesis and treatment of disease with Itraconazole analogs.

15 Claims, 7 Drawing Sheets

| | | | |
|---|---|---|---|
| 1a | cis-2S,4R,2'S | 1e | trans-2S,4S,2'S |
| 1b | cis-2S,4R,2'R | 1f | trans-2S,4S,2'R |
| 1c | cis-2R,4S,2'S | 1g | trans-2R,4R,2'S |
| 1d | cis-2R,4S,2'R | 1h | trans-2R,4R,2'R |

Terconazole        Ketoconazole

| Compounds | MB IC$_{90}$ (nM) | Gli1 ΔΔCT |
|---|---|---|
| 17a | 505 | 0.026 |
| 7a | 1,075 | 0.736 |
| 7b | 666 | 0.441 |
| 7c | 238 | 0.145 |
| 7d | 358 | 0.801 |
| 7e | 159 | 0.403 |
| Itra | 291 | 0.068 |
| 7f | 360 | 0.455 |
| 7g | 195 | 0.076 |
| 7h | 115 | 0.035 |
| 7i | 145 | 0.032 |
| 7j | 203 | 0.018 |
| 7k | 85 | 0.633 |
| 7l | 122 | 0.199 |
| 7m | 227 | 0.008 |
| 7n | 211 | 0.145 |
| 7o | 359 | 0.014 |
| 7p | 241 | 0.308 |
| 7q | 451 | 0.951 |
| 7r | 279 | 0.155 |
| 7s | 157 | 0.048 |
| 7t | 310 | 0.109 |
| 7u | 255 | 0.310 |
| 7v | 294 | 0.211 |
| 7w | 293 | 0.184 |
| 7x | 450 | 0.678 |

FIG. 10

ITRACONAZOLE ANALOGS AND USE THEREOF

CROSS-REFERENCE TO RELATED APPLICATIONS

This application is a 35 USC §371 National Stage application of International Application No. PCT/US2012/054306 filed Sep. 7, 2012, now pending; which claims the benefit under 35 USC §119(e) to U.S. Application Ser. No. 61/531,819 filed Sep. 7, 2011, now expired. The disclosure of each of the prior applications is considered part of and is incorporated by reference in the disclosure of this application.

GRANT INFORMATION

This invention was made with government support under Grant No. CA122814 awarded by the National Institutes of Health. The government has certain rights in the invention.

BACKGROUND OF THE INVENTION

1. Field of the Invention

The invention relates generally to derivatives of Itraconazole and more specifically to Itraconazole analogs and compositions as pharmaceuticals for the treatment of disease.

2. Background Information

Itraconazole is known for its use as a clinical agent for the treatment of a broad spectrum of fungal infections. However, it has been shown that Itraconazole also possesses potent in vitro and in vivo anti-angiogenic activity, and additionally inhibits both Hedgehog (Hh) signaling and the growth of murine medulloblastoma (MB) allografts with deregulated Hh activity. These observations have led to expansion of the potential therapeutic application of Itraconazole and have even sparked evaluation of this compound in four ongoing cancer clinical trials.

In an effort to better understand the structural parameters that influence anti-angiogenic activity, all eight stereoisomers of Itraconazole (1a-1h, FIG. 1) have been synthesized and the individual stereoisomers evaluated for in vitro anti-angiogenic and 14α-demethylase inhibition (14DM) dependent antifungal activities. The discrepancy between the activities in one pair of trans-stereoisomers 1e-1f and the other stereoisomers suggests that the molecular mechanism of Itraconazole in anti-angiogenesis is distinct from that for antifungal activity.

Although Itraconazole has demonstrated biological activity outside the realm of antifungal therapeutic regimens, little is known about the correlation between its pharmacological properties and structural features. The precise structural parameters of Itraconazole that are associated with its biological activity (e.g., Hh inhibitory activity) have not yet been ascertained. Thus, a need exists to elucidate the structure-activity relationship, for instance, in both anti-angiogenic and Hh targeting activity, and to exploit this knowledge in order to identify analogs of Itraconazole with greater potency and/or decreased side effects.

SUMMARY OF THE INVENTION

The present invention is based on the seminal discovery of a relationship between the Itraconazole side chain and putative binding site(s), which has been found to have an influence on its biological activity.

Provided herein are compounds of structural Formula I, or an optically pure stereoisomer or pharmaceutically acceptable salt thereof,

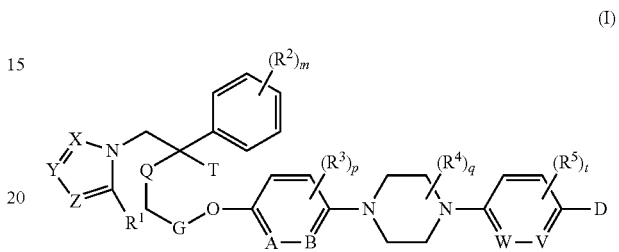

(I)

wherein:
X and Y are each independently CH or N;
A is $CR^6$ or N;
B is $CR^7$ or N;
W is $CR^8$ or N;
V is $CR^9$ or N;
Z is $CR^{10}$ or N;
Q is O or $CH_2$;
$R^6$, $R^7$, $R^8$, and $R^9$ are each independently chosen from the group consisting of hydrogen, alkoxy, alkyl, amino, halogen, hydroxy, haloalkyl, perhaloalkyl, perhaloalkoxy, nitro, and cyano, any of which may be optionally substituted;
each $R^2$, $R^3$, $R^4$, and $R^5$ are independently chosen from the group consisting of alkoxy, alkyl, amino, amido, halogen, hydroxy, haloalkyl, perhaloalkyl, perhaloalkoxy, nitro, and cyano, any of which may be optionally substituted;
T is $-OR^{11}$ or hydrogen;
$R^{11}$ is hydrogen or substituted or unsubstituted alkyl;
G is $-(CH_2)_n$ or G and $R^{11}$ together with the atom to which they are attached may optionally be joined together to form a monocyclic heterocycle including, but not limited to, dioxolane;
$R^1$ and $R^{10}$ are each independently hydrogen or alkyl;
n is an integer between 0 and 2;
p and t are each independently an integer between 0 and 2;
q and m are each independently an integer between 0 and 4;
D is chosen from the group consisting of

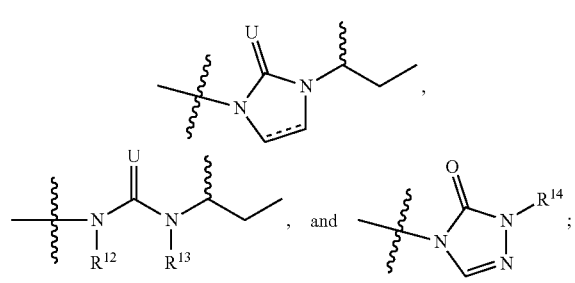

wherein,

----- is a single or double bond;

U is O or S;

$R^{12}$ and $R^{13}$ are each independently chosen from the group consisting of hydrogen and alkyl, any of which may be optionally substituted; and $R^{14}$ is chosen from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, and heterocycloalkylalkyl, any of which may be optionally substituted.

In certain aspects provided herein,

X and Z are each independently N;

Y is CH;

A is $CR^6$;

B is $CR^7$;

W is $CR^8$;

V is $CR^9$;

D is

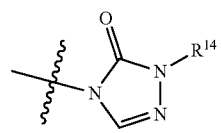

p, t, and q are each independently 0;

m is 2; and $R^1$, $R^6$, $R^7$, $R^8$, and $R^9$ are each independently hydrogen.

Also provided herein are compounds of structural Formula (II), or an optically pure stereoisomer or pharmaceutically acceptable salt thereof,

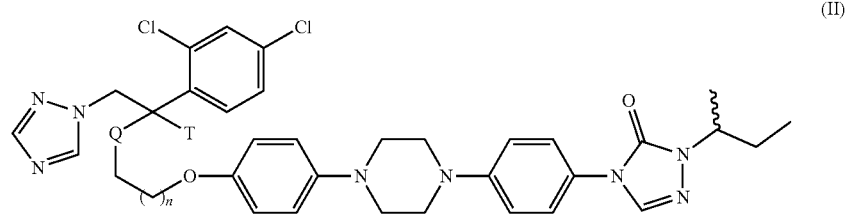

(II)

In certain aspects, Q is $CH_2$. In one aspect, Q is O. In other aspects, T is hydrogen. In yet other aspects, T is $OR^{11}$; and $R^{11}$ is hydrogen. In one embodiment, Q is $CH_2$ and T is hydrogen. In another embodiment, Q is $CH_2$; T is $OR^{11}$; and $R^{11}$ is hydrogen. In yet another embodiment, Q is O and T is hydrogen. In one embodiment, Q is O; T is $OR^{11}$; and $R^{11}$ is hydrogen.

In certain aspects, Q is O; n is 2; T is $OR^{11}$; and G and T are joined together to form a dioxolane moiety:

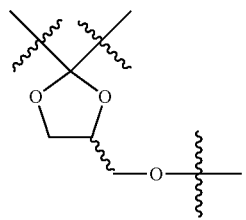 [SMILES: *OCC1COC(*)(*)O1]

Provided herein are compounds of structural Formula (III), or an optically pure stereoisomer or pharmaceutically acceptable salt thereof,

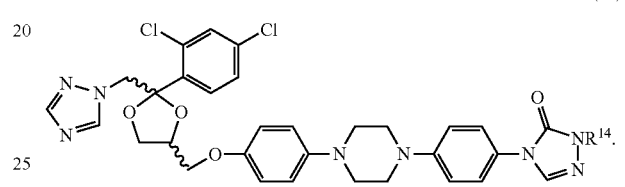

(III)

In one aspect, $R^{14}$ is chosen from the group consisting of hydrogen, alkyl, arylalkyl, alkoxyalkyl, arylalkoxy, alkynylalkyl, alkenylalkyl, cycloalkyl, cyanoalkyl, cycloalkylalkyl, and heterocycloalkylalkyl.

Provided herein are compounds of structural Formula (IV), or an optically pure stereoisomer or pharmaceutically acceptable salt thereof,

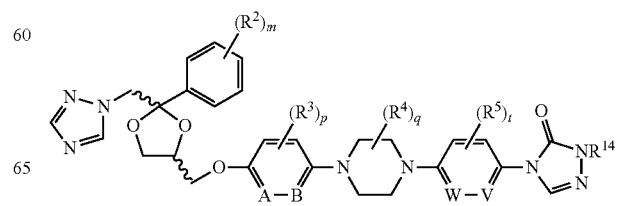

(IV)

In certain aspects, m is 2; and each $R^2$ is independently chlorine.

In other aspects, $R^{14}$ is

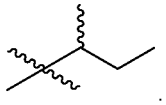 [SMILES: *C(C)CC]

In yet other aspects, W is $CR^8$; and V is $CR^9$. In certain aspects, p is 0. In yet other aspects, each $R^4$ is independently alkyl; and q is 0, 1, or 2. In further aspects, each $R^5$ is independently halogen; and t is 0, 1, or 2.

In one embodiment, W is $CR^8$; V is $CR^9$; p is 0; each $R^4$ and $R^5$ are independently alkyl or halogen; and q and t are 0, 1, or 2. In another embodiment, W is $CR^8$; V is $CR^9$; p is 0; each $R^4$ and $R^5$ are independently alkyl or halogen; q and t are independently 0, 1, or 2; A is $CR^6$ and B is $CR^7$ or N. In yet another embodiment, W is $CR^8$; V is $CR^9$; p is 0; each $R^4$ and $R^5$ are independently alkyl or halogen; q and t are independently 0, 1, or 2; A is N; and B is $CR^7$.

In certain aspects, A is $CR^6$; and B is $CR^7$. In another aspect, t is 0. In other aspects, each $R^3$ is independently halogen; and p is 0, 1, or 2.

In one embodiment, A is $CR^6$; and B is $CR^7$; t is 0; each $R^4$ and $R^3$ are independently alkyl or halogen; and q and p are independently 0, 1, or 2. In another embodiment, A is $CR^6$; and B is $CR^7$; t is 0; each $R^4$ and $R^3$ are independently alkyl or halogen; q and p are independently 0, 1, or 2; W is $CR^8$ and V is $CR^9$ or N. In yet another embodiment, A is $CR^6$; B is $CR^7$; t is 0; each $R^4$ and $R^3$ are independently alkyl or halogen; q and p are independently 0, 1, or 2; W is N; and V is $CR^9$.

In certain embodiments, $R^6$ is hydrogen. In other embodiments, $R^7$ is hydrogen. In yet other embodiments, $R^8$ is hydrogen. In further embodiments, $R^9$ is hydrogen.

Also provided herein are compounds of structural Formula (V) or an optically pure stereoisomer or pharmaceutically acceptable salt thereof, (V)

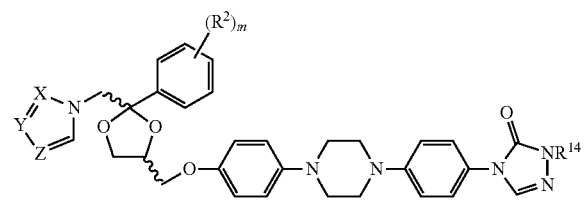

In one aspect, X is CH; Y is CH; and Z is $CR^{10}$. In certain aspects, X is N; Y is CH; and Z is $CR^{10}$. In another aspect, X is CH; Y is CH; and Z is N. In yet another aspect, X is CH; Y is N; and Z is N. In certain embodiments, X, Y and Z are each independently N. In other embodiments, X is CH; Y is N; and Z is $CR^{10}$. In further embodiments, X and Y are each independently N; and Z is $CR^{10}$.

Provided herein are compounds of structural Formula (VI) or an optically pure stereoisomer or pharmaceutically acceptable salt thereof, (VI)

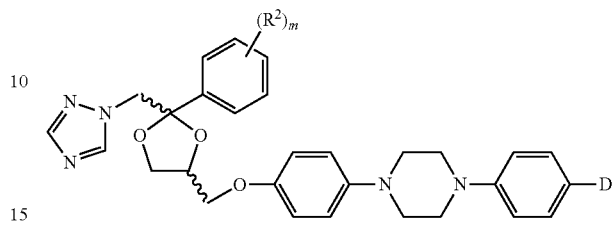

In one aspect, m is 2; each $R^2$ is independently halogen, such as chlorine; and D is

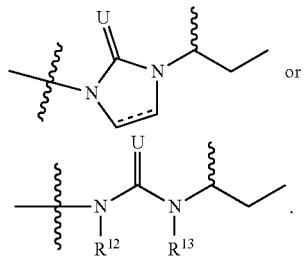

Also provided herein, are compounds of structural Formula (VII) or an optically pure stereoisomer or pharmaceutically acceptable salt thereof, (VII)

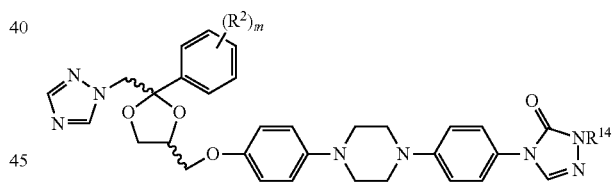

In certain aspects, m is 2; and $R^2$ is independently chosen from the group consisting of hydrogen, halogen, and perhaloalkyl.

In certain aspects, provided herein are compounds of Formula (VIII)

(VIII)

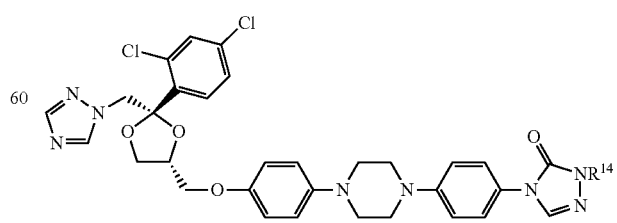

wherein $R^{14}$ is straight chain or branched alkyl.

In other aspects, provided herein are compounds of Formual (VIII) wherein, when $R^{14}$ is straight chain or branched alkyl, then $R^{14}$ is not methyl, ethyl, propyl, iso-propyl, n-butyl, iso-butyl, or iso-pentyl.

In yet other aspects, provided herein are compounds of Formulae (I)-(VIII), wherein $R^{14}$ is chosen from:

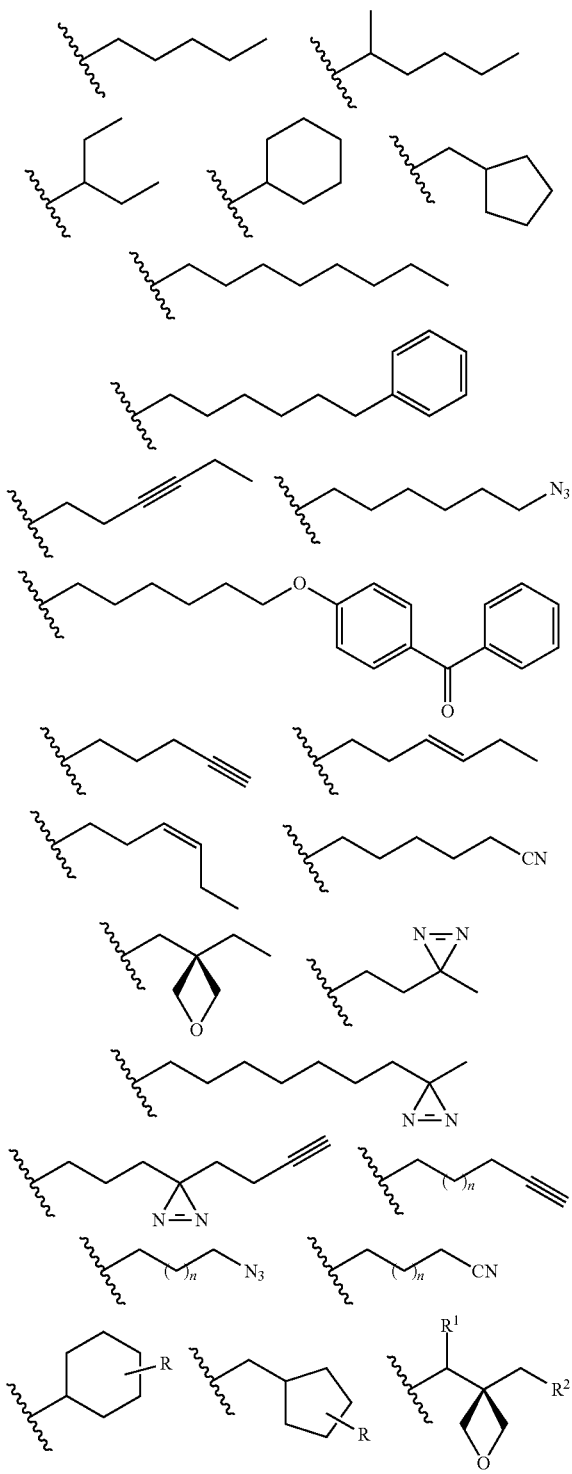

Certain embodiments also provide pharmaceutical compositions comprising one or more compounds disclosed herein together with a pharmaceutically acceptable carrier, as well as methods of making and using the compounds and compositions Provided herein are methods of inhibiting Hedgehog (Hh) pathway, comprising contacting a cell with a compound of structural Formula I, thereby inhibiting Hh pathway. Certain aspects provide for methods of treating a Hh pathway-mediated disease, comprising administering a therapeutically effective amount of a compound of structural Formula (I) to a patient in need thereof.

Also provided herein are methods of inhibiting angiogenesis. The methods include contacting a cell with a compound of structural Formula (I), thereby inhibiting angiogenesis. Also provided are methods for treating a disease or disorder associated with angiogenesis, comprising administering to a subject in need thereof, a therapeutically effective amount of a compound of structural Formula (I).

The compounds disclosed herein may possess useful vascular endothelial growth factor receptor 2 (VEGFR2) inhibiting activity, and may be used in the treatment or prophylaxis of a disease or condition in which VEGFR2 plays an active role. In certain embodiments, VEGFR2 glycosylation is inhibited by compounds of structural Formula (I). In one aspect, methods for treating a VEGFR2-mediated disorder in a patient in need of such treatment, comprising administering to the patient a therapeutically effective amount of a compound or composition are disclosed herein. In other aspects, the compounds disclosed herein may be useful for treating fungal infection, either systemically or topically.

As used herein, the terms below have the meanings indicated.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.). When n is set at 0 in the context of "0 carbon atoms", it is intended to indicate a bond or null.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon group having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl groups include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether group, wherein the term alkyl is as defined below. Examples of suitable alkyl ether groups include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur may be singly or doubly oxidized. Examples of suitable alkyl thioether groups include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched-chain hydrocarbon group having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C amido" as used herein, alone or in combination, refers to a C(═O)NR$_2$ group with R as defined herein. The term "N amido" as used herein, alone or in combination, refers to a RC(═O)NH group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C6H4═derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O carbamyl" as used herein, alone or in combination, refers to a OC(O)NRR' group with R and R' as defined herein.

The term "N carbamyl" as used herein, alone or in combination, refers to a ROC(O)NR' group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O carboxy" group refers to a RC(O)O— group, where R is as defined herein. A "C carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, may have an iodo, bromo, chloro or fluoro atom within the group. Dihalo and polyhaloalkyl groups may have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene.

(—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either:
1) monocyclic heteroaryl comprising five or six ring members, of which between one and four said members may be heteroatoms selected from the group consisting of O, S, and N; or
2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N sulfonamido" refers to a RS(=O)$_2$NR' group with R and R' as defined herein.

The term "S sulfonamido" refers to a S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N thiocarbamyl" refers to an ROC(S)NR'— group, with R and R' as defined herein.

The term "O thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, C(O)$CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and $R_n$ where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "optically pure stereoisomer" refers to stereosiomeric, such as enantiomeric or diastereomeric excess or the absolute difference between the mole fraction of each enantiomer or diastereomer.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition). Inhibition may be phrased in terms of an $IC_{50}$, defined below.

"Inhibitor" is used herein to refer to a compound that exhibits an $IC_{50}$ activity with respect to its target of no more than about 100 µM and more typically not more than about 50 µM, as measured in the assays described generally herein below. "$IC_{50}$" is that concentration of inhibitor which reduces the activity of an enzyme to half-maximal level. Certain representative compounds of the present invention have been discovered to exhibit inhibition VEGFR2 or Hedgehog (Hh) pathway. In certain embodiments, compounds will exhibit an $IC_{50}$ with respect to VEGFR2 or Hh pathway of no more than about 10 µM; in further embodiments, compounds will exhibit an $IC_{50}$ with respect to VEGFR2 or Hh pathway of no more than about 5 µM; in yet further embodiments, compounds will exhibit an $IC_{50}$ with respect VEGFR2 or Hh pathway of not more than about 1 µM, as measured in the VEGFR2 or Hh pathway assay described herein. In yet further embodiments, compounds will exhibit an IC50 with respect to VEGFR2 or Hh pathway of not more than about 200 nM.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations of the present invention may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic, otic, or nasal administration, the formulation may be a solution, a suspension, or a gel. In preferred aspects, the formulations are for topical application to the eye, nose, or ear in aqueous solution in the form of drops. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

For ophthalmic disorders, components of the invention may be delivered to the eye as a concentrated gel or a similar vehicle, or as dissolvable inserts that are placed beneath the eyelids.

The formulations of the present invention that are adapted for topical administration to the eye are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions of the present invention are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present invention may be used with contact lenses or other ophthalmic products.

Preferred formulations are prepared using a buffering system that maintains the formulation at a pH of about 4.5 to a pH of about 8. A most preferred formulation pH is from 6 to 8.

In particular embodiments, a formulation of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations are administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower ($C_1$-$C_6$) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose), synthetic polymers, galactomannan polymers (such as guar and derivatives thereof) and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating Rho kinase-mediated disorders in a human or animal subject in need of such treatment comprising administering to said subject an amount of a compound disclosed herein effective to reduce or prevent said disorder in the subject in combination with at least one additional agent for the treatment of said disorder that is known in the art. In a related aspect, certain embodiments provide therapeutic compositions comprising at least one compound of disclosed herein in combination with one or more additional agents for the treatment of Rho kinase-mediated disorders.

BRIEF DESCRIPTION OF THE DRAWINGS

FIG. 3 is a bar graph that depicts how the number of carbons and branching of the Itraconazole side chain influence the degree of glycosylation inhibition.

FIG. 4 is a scatter plot showing the correlation between potency in MB and HUVEC proliferation.

FIG. 10 is a table of the $IC_{90}$ values for MB proliferation assay and associated Gli1 transcript levels.

DETAILED DESCRIPTION OF THE INVENTION

Figure 1:
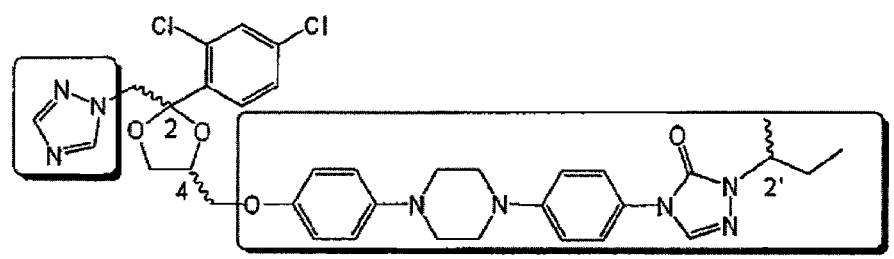
FIG. 1 shows the structures of the eight Itraconazole diastereomers arising from three stereogenic centers numbered 2, 4, and 2'. The cis-designation denotes that the two substituents in the boxes are on the same side of the 1,3-dioxolane ring, while trans-denotes the opposite orientation.
Figure 2:
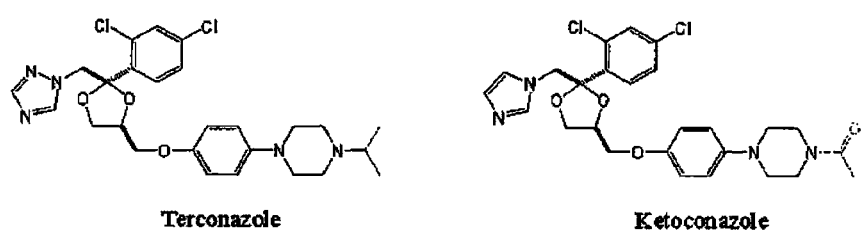
FIG. 2 shows the structures of terconazole (A) and ketoconazole (B).

Itraconazole shares a large degree of structural similarity with the other azole antifungals, such as terconazole and ketoconazole (FIGS. 1 and 2), which, despite their equipotent antifungal activity in comparison to Iitraconazole, do not inhibit proliferation of human umbilical vein endothelial cells (HUVEC) and fail to induce the VEGFR2 glycosylation defect (data not shown). The structural differences are particularly evident with respect to the triazolone ring and its sec-butyl side chain. This is suggestive that these moieties may be associated with the unique activities of Itraconazole. Thus, a library of twenty-five itraconazole analogs has been synthesized in which the sec-butyl side chain was replaced by a group of substituents with diverse structural variations. These analogs were evaluated in several assays, including HUVEC proliferation, VEGFR2 glycosylation, medulloblastoma (MB) proliferation, and Hh signaling as measured by Gli1 transcript levels as a pharmacodynamic marker of pathway activation.

Studies designed to investigate the molecular basis of the anti-angiogenic activity of itraconazole have revealed several cellular and biochemical effects in HUVEC. Itraconazole inhibits cholesterol trafficking in late endsomes/lysosomes and blocks mTORC1 and mTORC2 signaling. More recently, Itraconazole has been shown to impede the maturation of N-linked sugars appended to vascular endothelial growth factor receptor 2 (VEGFR2) and block VEGF-activated phosphorylation of the receptor, thereby arresting downstream signaling. Despite these new mechanistic insights, however, the direct target(s) of Itraconazole remains unknown; therefore, the preparation and analysis of the biological activity of a variety of Itraconazole analogs was undertaken.

The synthetic route for the syntheses of Itraconazole analogs 7a-7n (Table 1) with linear, branched, or cyclic hydrocarbon side chains is shown in Scheme 1. Because the 2S,4R-cis-stereochemistry on the 1,3-dioxolane ring is most favored for antiangiogenic activity, (unless otherwise stated) one single diastereomer 6a was used as the starting material to make the analogs.

TABLE 1

Side chain structures of compounds 4a-4n, 5a-5n, and 7a-7n

| Compounds | R |
|---|---|
| 4a/5a/7a | |
| 4b/5b/7b | |
| 4c/5c/7c | |
| 4d/5d/7d | |
| 4e/5e/7e | |
| 4f/5f/7f | |
| 4g/5g/7g | |
| 4h/5h/7h[a] | |
| 4i/5i/7i | |
| 4j/5j/7j | |
| 4k/5k/7k | |
| 4l/5l/7l | |
| 4m/5m/7m | |
| 4n/5n/7n | |

[a] Racemic on the side chain.

Alkylated compounds 4a-4-n (Table 1) were prepared by reaction of the free triazolone precursor 2 with commercially available alkyl bromides or alkyl tosylates synthesized from commercially available alcohols. For alkyl bromides or tosylates with a low boiling point, or potentially low stability or high reactivity at high temperatures, the reactions were carried out at room temperature with potassium carbonate and 18-crown-6. De-methylation of 4a-4-n with concentrated aqueous hydrobromic acid at 110° C. afforded the corresponding phenols 5a-5n (Table 1) in excellent yields. Final coupling of 5a-5n with 1,3-dioxolane tosylate 6a gave the desired side chain analogs 7a-7n.

Scheme 1[a]

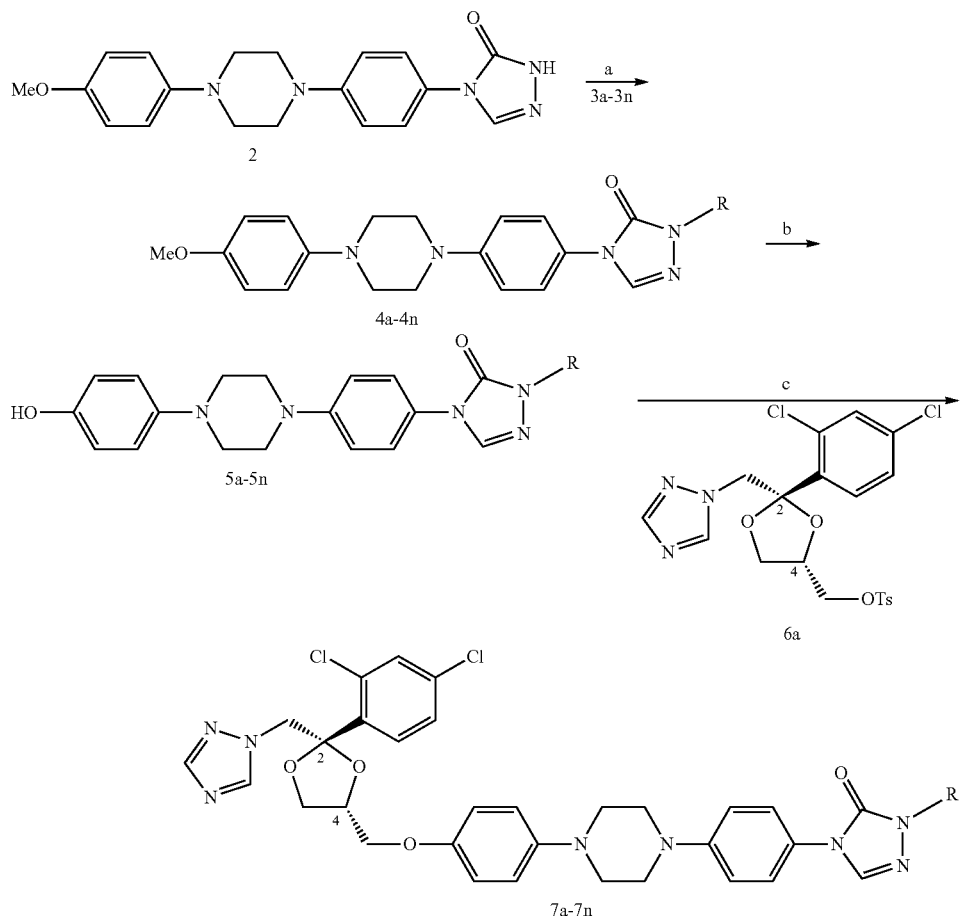

[a] Reagents and conditions: (a) K₂CO₃, 18-Crown-8, DMSO, rt, or K₂CO₃, KI, DMSO, 80° C.; (b) 48% aqueous HBr, 110° C.; (c) NaH, DMSO, 50° C. → 85° C.

The analogs 7o-7q (Table 2) were prepared according to the synthetic route shown in Scheme 2. To incorporate the functional groups (azido, internal alkyne, and benzophenone) into the side chain, the methyl protecting group of the phenolic hydroxyl group was replaced with the methoxymethyl (MOM) group to avoid the harsh demethylation conditions (HBr, 110° C.). To start with, N-(4-hydroxyphenyl)-N'-(4-nitrophenyl)-piperazine 10 was prepared by heating the mixture of commercially available N-(4-hydroxylphenyl)-piperazine 8 and 1-chloro-4-nitrobenzene 9 in N-methylpyrrolidone (NMP) overnight. The crude product, isolated from isopropanol precipitation, was directly reacted with methoxymethyl chloride to afford the MOM-protected intermediate 11, which was purified by column chromatography. Subsequently, the nitro group in 11 was reduced to the amino group by refluxing with hydrazine monohydrate in the presence of 10% palladium on charcoal. In a three-step sequence, the aniline intermediate 12 was then reacted with phenyl chloroformate, hydrazine monohydrate, and formamidine acetate to construct the triazolone ring in 51% yield over three steps. Next, the N-alkylation of 13 with the corresponding alkylating reagents 3o-3q (see Examples) under basic conditions afforded the intermediates 14a-14c (Table 2), which were in turn treated with 50% trifluoroacetic acid in dichloromethane at room temperature to remove the MOM group. The acquired phenols 5o-5q were subjected to the aforementioned coupling conditions to give the final products 7o-7q.

Scheme 2

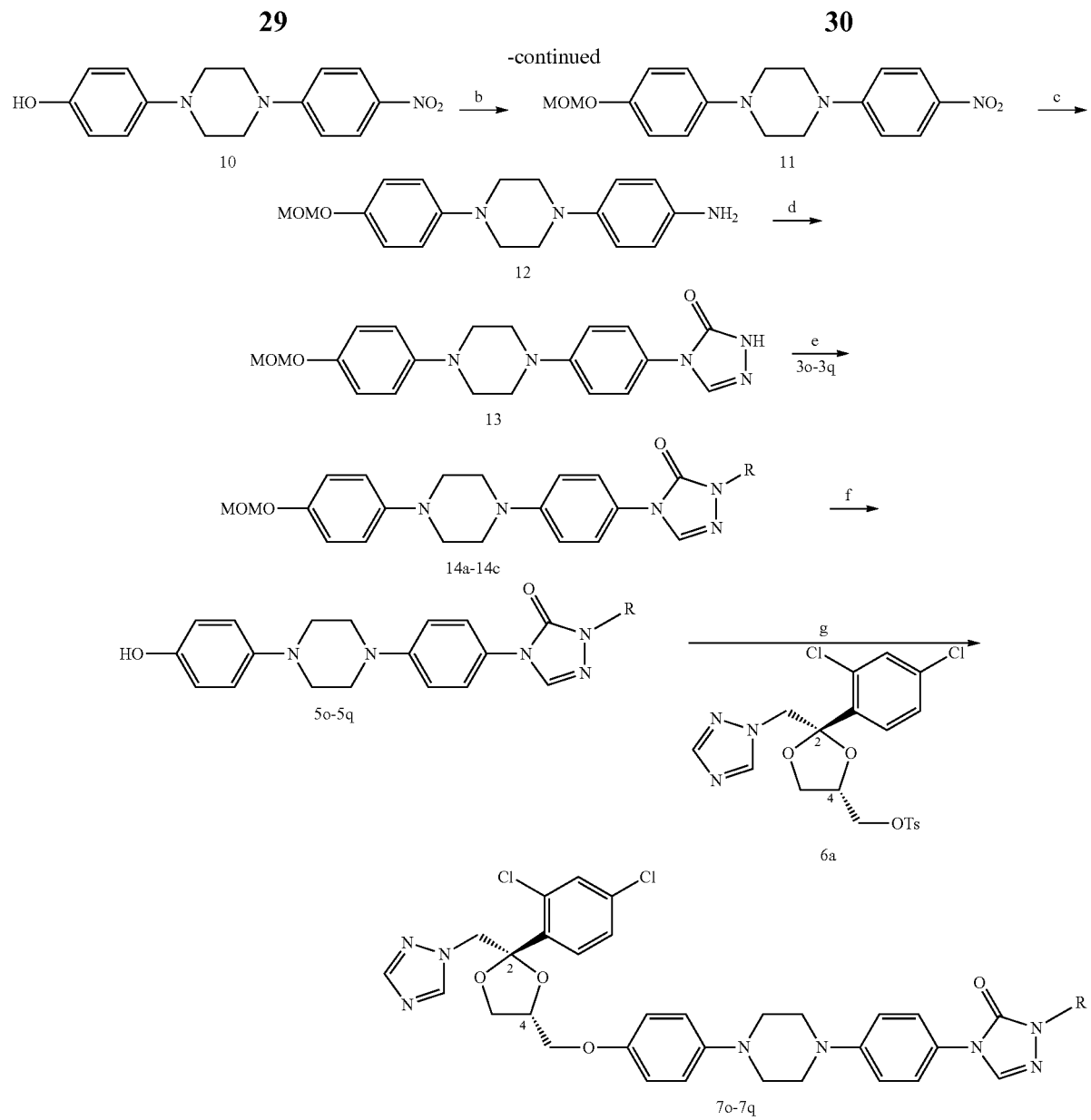

[a] Reagents and conditions: (a) DIPEA, NMP, 125° C.; (b) MOMCl, DIPEA, rt, 79% over two steps; (c) 10% Pd/C, NH$_2$NH$_2$·H$_2$O, EtOH, reflux, 99%; (d) i) Phenyl chloroformate, pyridine, CH$_3$CN; ii) NH$_2$NH$_2$·H$_2$O, 1,4-dioxane, reflux; iii) Formamidine acetate, 1-propanol, 110° C., 51% over 3 steps; (e) K$_2$CO$_3$, KI, DMSO, 80° C.; (f) TFA, 0° C.→rt; (g) NaH, DMSO, 50° C. → 85° C.

TABLE 2

Side chain structures of compounds 14a-14c, 5o-5q, and 7o-7q

| Compounds | Structure of the R group |
|---|---|
| 14a/5o/7o | (pent-2-ynyl chain) |
| 14b/5p/7p | (azidohexyl chain, N$_3$) |
| 14c/5q/7q | (hexyloxy-phenyl-benzoyl chain) |

Although the synthetic route described in Scheme 2 can accommodate a broad range of functional groups, two column purifications were usually required to remove DMSO and obtain the final products in good quality. To avoid the use of DMSO as the reaction solvent, a linear synthetic methodology, as shown in Scheme 3, was adopted. The reaction sequence was first examined by using 2R,4R-cis-tosylate 6b as the starting material due to its relatively high abundance and similar biological activity according to the reported stereoisomers.[3] N-(4-hydroxyphenyl)-N'-(4-nitrophenyl)-piperazine 10 was purified by column chromatography before it was coupled with 6b. Formation of the triazolone moiety in 17b from the nitro group in 15b was achieved by following the similar reaction conditions described in Scheme 2. Using potassium carbonate in combination with 18-crown-6 as the deprotonation reagents, the final N-alkylation of 17b with 4-pentynyl-1-tosylate 3s was performed in acetonitrile at 40° C. to give the final product 7r in 63% yield. Analogs 7s-7x (Table 3) were obtained from 2S, 4S-cis-tosylate 6a and the corresponding alkyl bromides or tosylates 3s-3x in a similar fashion.

Scheme 3[a]

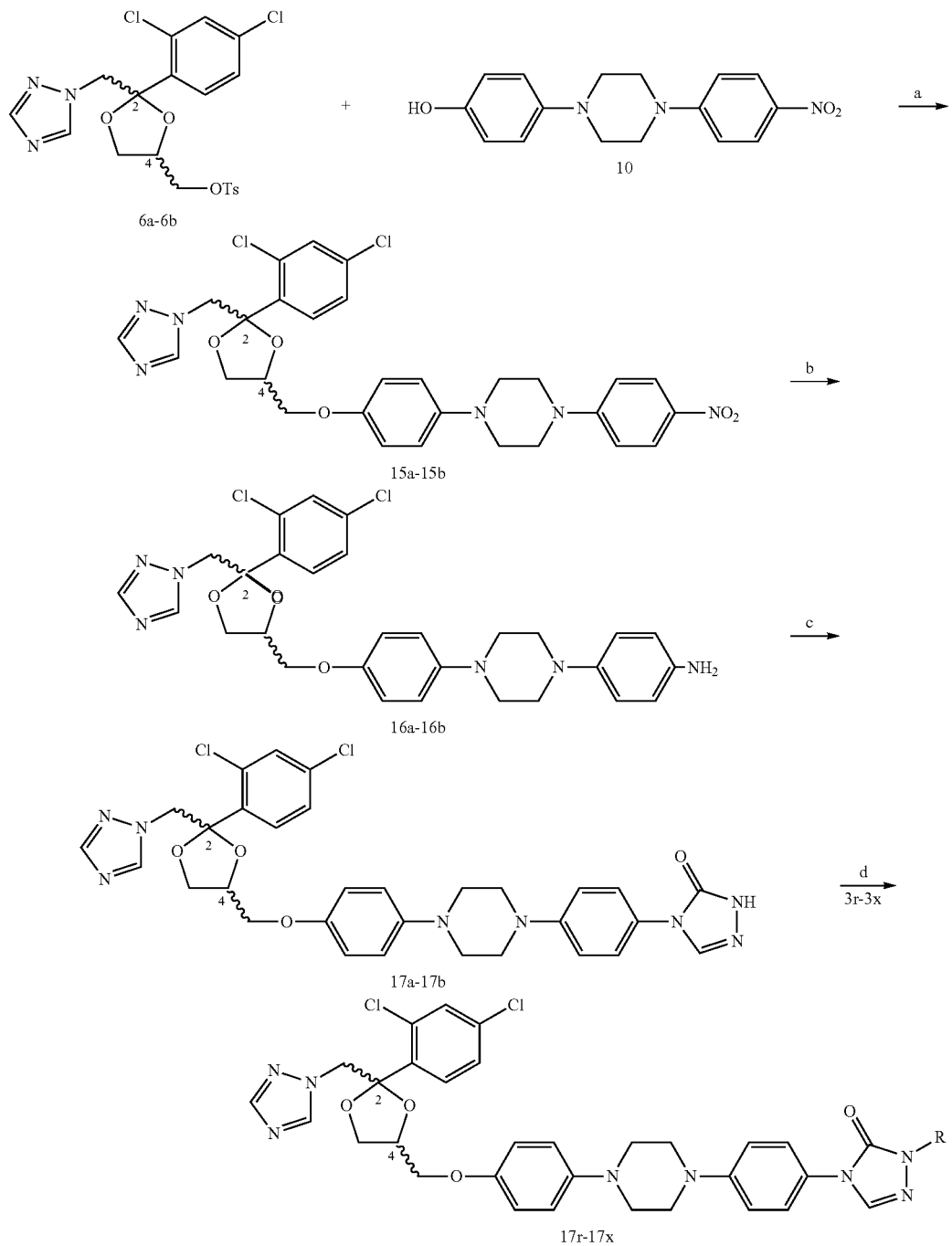

[a] Reagents and conditions: (a) NaH, DMF, 50° C., 88%; (b) 10% Pd/C, NH$_2$NH$_2$•H$_2$O, EtOH, reflux, 99%; (c) i) Phenyl chloroformate, pyridine, CH$_3$CN; ii) NH$_2$NH$_2$•H$_2$O, 1,4-dioxane, reflux; iii) Formanidine acetate, 1-propanol, 110° C., 48% over 3 steps; (d) K$_2$CO$_3$, 18- crown-6, CH$_3$CN, 40° C..

The activity of the analogs against HUVEC proliferation, an in vitro proxy for angiogenesis inhibition (Table 3) was analyzed. From Table 3, it is clear that modification of the side chain in most analogs did not dramatically affect the activity. Those analogs with extremely short side chains (7a and 7b) or lacking any side chain (17a) had lower potency for inhibition of HUVEC proliferation than Itraconazole. A few analogs, however, possessed considerably higher potency, including 7r and 7u.

TABLE 3

Inhibition of HUVEC proliferation and VEGFR2 glycosylation, MB proliferation and Gli1 transcription by Itraconazole stereoisomers 1a-1h and side chain analogs 17a and 7a-7x[a]

| Compounds | R | (structure) | Proliferation (IC$_{50}$/IC$_{50}$ Itra) | Glycosylation (2 μM dose) | MB Proliferation (IC$_{50}$/IC$_{50}$ Itra) | Gli1 Inhibition (IC$_{90}$ Prolif. dose) |
|---|---|---|---|---|---|---|
| 1a | 2S,4R,2'S | sec-butyl | 0.8[b] | ++ | 1.3 | nd |
| 1b | 2S,4R,2'R | sec-butyl | 1.1[b] | ++ | 1.4 | nd |
| 1c | 2R,4S,2'S | sec-butyl | 1.6[b] | ++ | 1.3 | nd |
| 1d | 2R,4S,2'R | sec-butyl | 2.5[b] | ++ | 1.7 | nd |
| 1e | 2S,4S,2'S | sec-butyl | 3.1[b] | + | 2.1 | nd |
| 1f | 2S,4S,2'R | sec-butyl | 3.9[b] | − | 1.7 | nd |
| 1g | 2R,4R,2'S | sec-butyl | 3.2[b] | + | 1.5 | nd |
| 1h | 2R,4R,2'R | sec-butyl | 3.7[b] | − | 2.3 | nd |
| 17a[c,d] | H | | 2.78 | − | 0.89 | ++ |

TABLE 3-continued

Inhibition of HUVEC proliferation and VEGFR2 glycosylation, MB proliferation and Gli1 transcription by Itraconazole stereoisomers 1a-1h and side chain analogs 17a and 7a-7x[a]

| Compounds | R | Proliferation (IC$_{50}$/IC$_{50}$ Itra) | Glycosylation (2 μM dose) | MB Proliferation (IC$_{50}$/IC$_{50}$ Itra) | Gli1 Inhibition (IC$_{90}$ Prolif. dose) |
|---|---|---|---|---|---|
| 7a[d] | methyl | 4.00 | − | 2.71 | − |
| 7b[d] | ethyl | 2.94 | − | 1.62 | − |
| 7c[d] | n-propyl | 1.06 | + | 1.01 | ++ |
| 7d[d] | isopropyl | 2.18 | − | 1.06 | − |
| 7e[d] | n-butyl | 2.10 | − | 0.70 | − |
| Itra[f] | sec-butyl | 1.00 | ++ | 1.00 | ++ |
| 7f[d] | isobutyl | 1.32 | ++ | 0.86 | − |
| 7g | n-pentyl | 1.09 | − | 0.66 | ++ |
| 7h[c] | 3-pentyl | 0.75 | ++ | 0.38 | ++ |
| 7i[d] | isopentyl | 1.42 | + | 0.41 | ++ |
| 7j | 2-ethylbutyl | 1.10 | + | 0.54 | ++ |

TABLE 3-continued

Inhibition of HUVEC proliferation and VEGFR2 glycosylation, MB proliferation and Gli1 transcription by Itraconazole stereoisomers 1a-1h and side chain analogs 17a and 7a-7x[a]

| Compounds | R | Proliferation (IC$_{50}$/IC$_{50}$ Itra) | Glycosylation (2 μM dose) | MB Proliferation (IC$_{50}$/IC$_{50}$ Itra) | Gli1 Inhibition (IC$_{90}$ Prolif. dose) |
|---|---|---|---|---|---|
| 7k | cyclohexyl | 0.44 | ++ | 0.37 | − |
| 7l | cyclopentylmethyl | 0.50 | ++ | 0.50 | + |
| 7m | octyl chain | 2.24[g] | − | 0.67 | ++ |
| 7n | phenylhexyl | 1.45[g] | − | 0.69 | ++ |
| 7o | hex-3-ynyl | 1.09 | − | 1.07 | ++ |
| 7p | azidohexyl | 0.30 | + | 0.70 | + |
| 7q | (4-benzoylphenoxy)hexyl | >69.9[g] | − | 0.80 | − |
| 7r[a] | pent-4-ynyl | 0.14 | − | 0.71 | ++ |
| 7s | (E)-hex-3-enyl | 1.57 | − | 0.63 | ++ |
| 7t | (Z)-hex-3-enyl | 0.73 | − | 0.94 | ++ |

TABLE 3-continued

Inhibition of HUVEC proliferation and VEGFR2 glycosylation, MB proliferation and Gli1 transcription by Itraconazole stereoisomers 1a-1h and side chain analogs 17a and 7a-7x[a]

| Compounds | R | Proliferation ($IC_{50}/IC_{50}$ Itra) | Glycosylation (2 μM dose) | MB Proliferation ($IC_{50}/IC_{50}$ Itra) | Gli1 Inhibition ($IC_{90}$ Prolif. dose) |
|---|---|---|---|---|---|
| 7u | ~~~~~CN | 0.18 | ++ | 0.84 | + |
| 7v | ~~~(branched ethyl/oxetane) | 0.77 | ++ | 0.74 | + |
| 7w | ~~~(diazirine methyl) N=N | >13.8 | + | 1.32 | + |
| 7x | ~~~~~~~(long chain diazirine) N=N | 1.1[g] | − | 1.18 | − |

[a]Stereochemistry on the 1,3-dioxolane ring is 2S,4R for 17a, 7a-7q, and 7s-7x and 2R,4S for 7r;
[b]Proliferation data from ref. 3;
[c]Purity is 94.0%, $t_R$ = 6.92 min;
[d]Already reported in Ref. 7;
[e]Mixture of the four cis-diastereomers, from Sigma-Aldrich;
[f]Mixture of stereoisomers on the side chain;
[g]$EC_{50}/IC_{50}$ Itra.

The similar or even improved potency for compounds 7k, 7l and 7v, all of which have bulky side chains, suggests a putative binding site that is not sterically hindered. The relatively rigid conformation in 7o, 7s, and 7t further supports this idea and further suggests that the binding pocket in the putative target may be quite deep; however, the loss of activity in 7w does not appear to be consistent with this trend. One possible explanation for this observation is that the loss of lipophilicity resulting from the incorporation of two nitrogens may have affected activity. This may be supported by the data for 7x in which an increase in lipophilicity appears to have compensated for the presence of the diazirine. The near total loss of activity in 7q may be indicative of a limit to the size of the side chain with respect to inhibition of HUVEC proliferation.

Perhaps most notably, the potency of Itraconazole against HUVEC proliferation was significantly increased by the incorporation of relatively small functional groups, such as the azido group in 7p, the terminal alkyne in 7r, and the cyano group in 7u. This implies that there are some interactions in the binding site of the side chain that are not utilized by the sec-butyl group in Itraconazole. These results also suggest that substituents in place of the sec-butyl group of Itraconazole can be further explored to optimize the potency of Itraconazole.

Figures 3, 4:
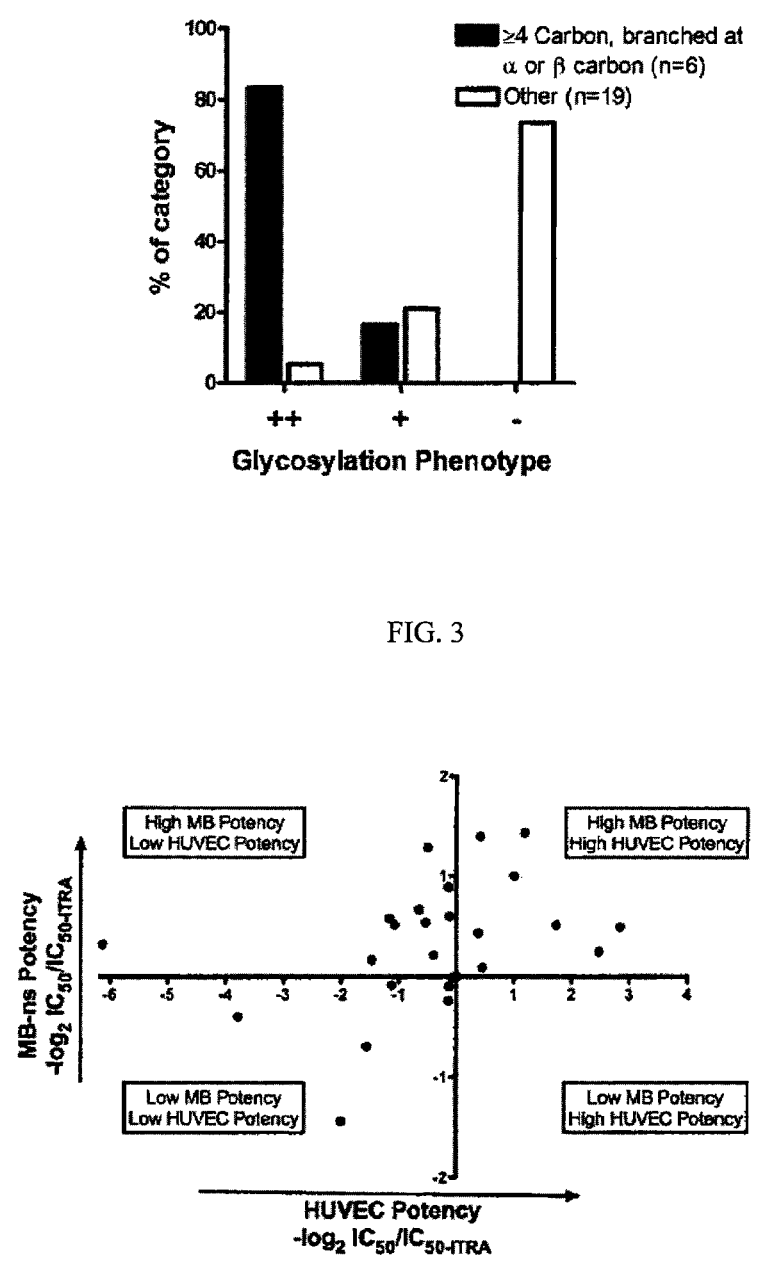
Figure 6:
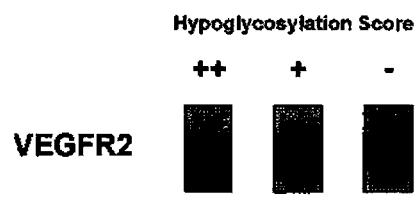
FIG. 6 is a schematic representation of the VEGFR2 glycosylation scoring system.

Because Itraconazole was found to block the normal maturation of N-glycans on VEGFR2, the influence of the side chain structure on this activity was analyzed as well (Table 3). VEGFR2 hypoglycosylation was scored either robust (++), intermediate (+), or absent (−) (FIG. 6). Robust inhibitors of glycosylation had significantly ($p<0.05$) greater potencies against proliferation than the group in which the hypoglycosylation was absent, suggesting that this phenotype makes an overall contribution to inhibition of HUVEC proliferation (Table 4). Side chains comprised of 4 carbons or greater with branching at the α or β position appeared to strongly favor robust glycosylation inhibition compared with all other structural isomers (FIG. 3). However, compound 7j produced an intermediate glycosylation defect and was an exception to this observation. Compared with 7k, 7l, and 7v, the other analogs, which contained bulky side chains and retained glycosylation inhibition, 7j had the greatest number of possible rotational isomers, suggesting that only certain conformations may be suitable for glycosylation inhibition.

TABLE 4

Correlation between HUVEC proliferation inhibition and glycosylation phenotype

| Glycosylation Inhibition | − | + | ++ |
|---|---|---|---|
| n | 10 | 7 | 16 |
| Mean $IC_{50}^a$ (μM) | 6.3 | 3.4 | 1.0 |

TABLE 4-continued

Correlation between HUVEC proliferation inhibition and glycosylation phenotype

| Glycosylation Inhibition | − | + | ++ |
|---|---|---|---|
| Mean Log2 (IC$_{50}$$^a$) | 1.0 | 0.9 | −0.32 |
| p-value$^{b, c}$ | N/A | 0.83 | 0.04 |

$^a$Relative to Itraconazole (IC$_{50}$ analog/IC$_{50}$ itraconazole);
$^b$p-value calculated by a two-tailed Student's t-test from log transformed data;
$^c$compared to the "−" group.

Itraconazole has recently found to inhibit Hh pathway signaling in a 3T3 cell-based reporter system and in medulloblastoma allografts exhibiting Hh pathway-dependent growth. This activity against Hh signaling also seems to be unrelated to inhibition of 14DM, as other azole antifungal agents demonstrate decreased potency against this pathway, regardless of their activity on human 14DM. To explore the relation of the anti-angiogenic and anti-Hh signaling capacity of Itraconazole, the anti-proliferative potency of the side chain analogs in MB cultures was assessed. These cultures were derived from Ptch$^{+/+}$;p53$^{−/−}$ mice that spontaneously develop medulloblastoma associated with ligand independent Hh pathway activation. IC$_{50}$ values for proliferation were determined for analogs and are represented as relative potencies compared to that of Itraconazole (Table 3). Overall, there was poor correlation between analog potency ratios for MB and HUVEC proliferation (Spearman r=0.327; p=0.063) (FIG. 4). Notably, compounds 7q and 7w, which lost >69.9- and >13.8-fold of activity against HUVEC, respectively, had respective relative activities of 0.8 and 1.32 against MB proliferation when compared to Itraconazole. Furthermore, the lack of data points in the lower right quadrant of FIG. 4 illustrates that without exception, all analogs demonstrating equivalent or increased potency against HUVEC proliferation with respect to Itraconazole also demonstrate equivalent or increased potency against MB proliferation. These findings are consistent with the possibility that the target of Itraconazole in HUVEC may also contribute to the potency of Itraconazole against MB proliferation.

Inhibitors of the Hh pathway are known to inhibit MB cell proliferation. However, MB cell proliferation is also affected by drugs with targets other than Hh signaling. Therefore, to determine the extent to which the demonstrated potencies on MB proliferation are associated with Hh pathway inhibition, established MB colonies were exposed to the Itraconazole analogs at the IC$_{90}$ for MB proliferation and quantified transcript levels of Gli1, a transcriptional gene target of the Hh pathway. These data were then scored based on transcript levels associated with exposure of MB to synthetic Smoothened inhibitors, Hh Antag and GDC-0449 (vismogedib) at the IC$_{90}$ for proliferation. The results are listed in Table 3.

Figure 7:
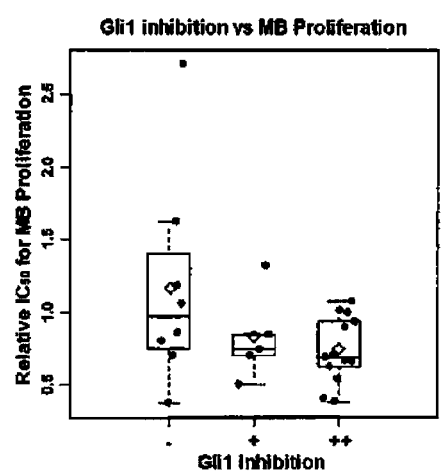
FIG. 7 is a graph that shows the correlation between MB proliferation potency and Hh pathway inhibition. Box=interquartile range, Wiskers=adjacent values, Bars=median, Diamond=mean, Circles=data points, p-value=0.05 as determined by Cuzick test for trend.

Overall, there was a statistically significant association between inhibition of MB proliferation and inhibition of Hh pathway activity (p=0.05; FIG. 7). However, some analogs with relatively weak inhibition of Gli1 expression demonstrated potent inhibition of MB proliferation, suggesting that in these instances, anti-proliferative activity was predominantly Hh pathway independent.

Figure 8:
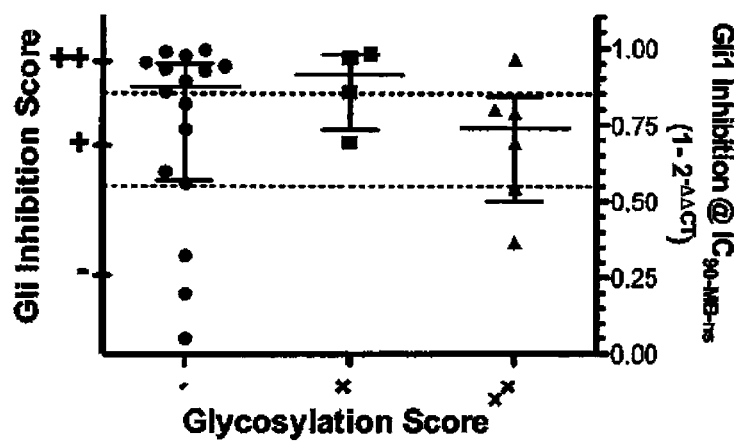
FIG. 8 is a graph showing discordance between VEGFR2 glycosylation in HUVEC and Hh pathway inhibition in MB cells. bars=median±interquartile range.

There was no evident association between inhibition of VEGFR2 glycosylation and targeting of the Hh pathway (FIG. 8). Nine of ten analogs demonstrating strong inhibition of the Hh pathway did not inhibit VEGFR2 glycosylation. Furthermore, of the six strongest inhibitors of VEGFR2 glycosylation, two were not associated with Hh-dependent inhibition, three were intermediate inhibitors, and only one strongly inhibited Hh signaling. Notably, with the exception of compound 7h, all analogs demonstrating strong inhibition of VEGFR2 glycosylation also demonstrated increased potency against MB proliferation. These findings reveal a high level of discordance between these pharmacodynamic markers.

Figure 5:
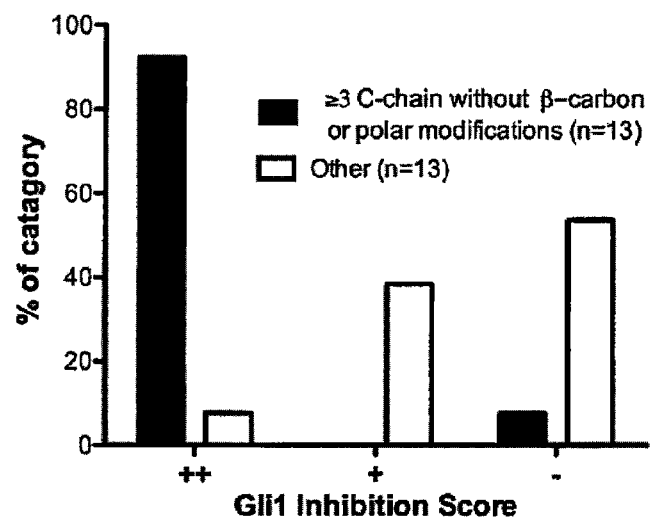
FIG. 5 is a bar graph that shows length, branching and polarity of Itraconazole side chain influences Hh pathway inhibition.

A study of side chain modifications associated with strong Hh pathway inhibition reveals several structure-activity relationship (SAR) trends. Analogs with side chains of three carbons or more in length without polar groups or branching at the β carbon demonstrated strong inhibition of Hh pathway activity (FIG. 5). Compound 7e is an exception, as it was not associated with strong Hh pathway inhibition, yet structurally closely related analogs 7c and 7g exhibited strong Hh inhibition.

Examination of the side chains included in this defined set reveals that the criteria for potent inhibition of the Hh pathway is permissive to extension of the side chain beyond 3 carbons in length, as elongation up to n-octane (compound 7m) generally resulted in increased potency for Hh pathway inhibition and MB proliferation. Retention of potency for Hh pathway inhibition with compound 7n and loss of pathway specific activity with compound 7q suggests that there is some allowance for bulk at the distal end of these extensions, but not to the extent necessary to accommodate a benzophenone group, similar to the herein described observations for HUVEC proliferation. Pathway inhibition was also permissive to branching on the α or γ carbon as demonstrated by Itraconazole, 7h, 7i, and 7j. Compound 7k appears to be an exception, which exception, in the context of the activity demonstrated by 7j, suggests that branching from the a position was not permissive to moieties with either large displacement volume or restricted rotational degrees of freedom. Pathway inhibition was also favored in compound 7r, containing a terminal alkyne. Alkene and alkyne linkages between γ and δ carbons were also active against the pathway.

Taken together, the SAR trends and defined side chain sets derived from these analyses provide criteria for examining the relationship between activities against the Hh pathway and those targeting glycosylation and HUVEC proliferation. Overall, divergence between the activity of 7g and 7m demonstrate MB selectivity for saturated alkane chains greater than 4 carbons in length. Functional groups associated with the distal ends of 7n, 7p, and 7u further differentiate these activities and identify a preference for small, polar cyano and azido functional groups in the pharmacophore associated with effects on HUVEC proliferation and VEGFR2 glycosylation, whereas a more bulky, hydrophobic phenyl group is preferred for activity against Hh signaling. Compounds 7k and 7l identify large groups proximal to the core triazolone ring as having improved activity in HUVEC proliferation and favoring inhibition of VEGFR2 glycosylation, whereas these structures were disfavored for inhibition of the Hh pathway. Interestingly, the sec-pentyl modification associated with compound 7h represents the only side chain composition in the analogue set that simultaneously inhibits glycosylation and the Hh pathway. Most notably, this compound was also the only analog demonstrating increased potency across all parameters as compared with Itraconazole.

Through N-alkylation of the triazolone moiety in three different synthetic routes, a focused library of twenty-five side chain analogs of Itraconazole was synthesized. These analogs were screened for effects on HUVEC proliferation, VEGFR2 glycosylation, inhibition of Gli1 transcription in MB cells, and inhibition of MB proliferation. Analogs that were robust inhibitors of glycosylation were significantly associated with greater potency against HUVEC proliferation, suggesting that glycosylation inhibition contributes to the overall antiangiogenic activity of Itraconazole. The SAR study on antiangiogenic activity suggests that the binding site of the side chain may be mainly hydrophobic and relatively deep and flexible. It was also possible to incorporate additional functional groups, such as terminal alkyne, azido, and cyano, which led to enhancement of antiangiogenic activity. However, to achieve potent inhibition against VEGFR2 glycosylation, there were more stringent structural and functional requirements for the side chain, mainly that side chains of at least four carbons with branching at the α or β position were generally required for high potency. Surprisingly, it was found that some compounds with relatively potent inhibitory activity against MB proliferation were not similarly potent inhibitors of Gli1 transcription. Of the derivatives tested, 12 were found to exert strong Hh pathway inhibition associated with their anti-proliferative effects in MB, as indicated by inhibition Gli1 transcript levels. These compounds were generally characterized by side chains with extensions of at least three carbons in length and lacking branching from the β position. The distinct trends demonstrated by the SAR of these two molecular activities, together with the lack of correlation between the potency of the analogs in HUVEC and MB proliferation, suggest that Itraconazole's effect on the Hh pathway is largely unrelated to the activity of Itraconazole in HUVEC. It is possible that the effects of Itraconazole on HUVEC and Hh signaling pathway are mediated by distinct molecular targets. Together, the results presented herein have deepened the understanding of the role of the Itraconazole side chain in the antiangiogenic and anti-Hh pathway activities of this drug and will likely facilitate the design of future analogs with increased potency for specific activities. Analogs with selectivity for one or more pathways may be useful in animal studies to clarify the role for each activity in in vivo tumor suppression.

The following examples are intended to illustrate but not limit the invention.

GENERAL EXPERIMENTAL CONDITIONS

Reactions were carried out in oven-dried glassware. All reagents were purchased from commercial sources and were used without further purification unless noted. Unless stated otherwise, all reactions were carried out under a positive pressure of argon monitored by Merck precoated silica gel 60E-254 plates and visualized using 254 nm UV light. Column chromatography was performed on silica gel (200-400 mesh, Merck). The ratio between silica gel and crude product ranged from 100 to 50:1 (w/w). NMR data were collected on a Varian Unity-400 (400 MHz $^1$H, 100 MHz $^{13}$C) machine in the Department of Pharmacology and Molecular Sciences, the Johns Hopkins University. $^1$H NMR spectra were obtained in deuteriochloroform (CDCl$_3$) with either tetramethylsilane (TMS, δ=0.00 for $^1$H) or chloroform (CHCl$_3$, δ=7.27 for $^1$H) as an internal reference. $^{13}$C NMR spectra were proton decoupled and were in CDCl$_3$ with either TMS (δ=0.0 for $^{13}$C) or CHCl$_3$ (δ=77.0 for $^{13}$C) as an internal reference. Chemical shifts are reported in ppm (δ). Data are presented in the form: chemical shift (multiplicity, coupling constants, and integration). $^1$H data are reported as though they were first order. The errors between the coupling constants for two coupled protons were less than 0.5 Hz, and the average number was reported. Low-resolution mass spectra were obtained on a API 150EX™ single quadrupole LC/ESI-MS system in the Department of Pharmacology and Molecular Sciences or on a Voyager DE-STR, MALDI-TOF instrument at the AB Mass Spectrometry/Proteomics Facility at the Johns Hopkins University. The MALDI-samples were prepared by mixing droplets of the sample solutions in chloroform or methanol and 2,5-dihydroxybenzoic acid solution in acetone, where the latter served as the matrix. The reported purity values were obtained with a JASCO PU-2089S Plus quaternary pump system, using an MD-2010 Plus PDA detector at the wavelength of 256 nm, and a Varian Microsorb-MV 100-5 C18 column. The eluant consisted of acetonitrile and 0.125% diethylamine in water, the ratio and flow rate of which depends on the compound. When the purity derived from HPLC analysis is greater than 99%, it is reported as >99%.

The experimental procedures and analytical data for new compounds 3h, 3l, 3n-3t, 3v-3x, 4a-4-n, 5a-5q, 11-13 and 14a-14c; VEGFR2 glycosylation scoring, characterization of MB culture system, experimentally determined IC$_{90}$ and associated ΔΔCt values, and correlations between Gli1 inhibition and MB proliferation as well as VEGFR2 glycosylation are described below.

Compounds 3h, 3l, 3n-3t, 3v-3x, 4a-4-n, 5a-5q, 11-13 and 14a-14c can be synthesized according to the following synthetic procedures.

Tosylation or brosylation of alcohols: To a solution of alcohol (1 equiv.), Et$_3$N (1.5-2.0 equiv.), and N,N-dimethylamino-pyridine (DMAP, 0.5-1 equiv.) in CH$_2$Cl$_2$ was slowly added a solution of p-toluenesulfonic chloride (TsCl) or 4-bromobenzene-1-sulfonyl chloride (BsCl) (1.1-1.3 equiv.) in CH$_2$Cl$_2$ at 0° C. The reaction mixture was stirred at 0° C. for 1 h, and then warmed to room temperature for another 3 h. After diluted with water, the reaction mixture was extracted with more CH$_2$Cl$_2$. The organic layer was combined, dried (Na$_2$SO$_4$), filtered, and concentrated to yield the crude product, which was then purified by column chromatography.

Alkylation of triazolone (Method A): To a suspension of triazolone 2 or 13 (1 equiv.) in DMSO was added K$_2$CO$_3$ (2.0-2.2 equiv.) or Cs$_2$CO$_3$ (1.6-2.0 equiv.). The resulting mixture was stirred at room temperature for 1 h. After the addition of alkyl bromide, alkyl tosylate, or alkyl brosylate (1.3-2.0 equiv.), the temperature was increased to 80° C. and kept overnight. In most cases, KI (0.2-0.5 equiv.) was also added to accelerate the reaction. After cooling to room temperature, the reaction mixture was diluted with water and extracted with CH$_2$Cl$_2$. The combined organic layer was dried (Na$_2$SO$_4$), filtered, and concentrated to yield the crude product, which was purified by column chromatography.

Alkylation of triazolone (Method B): To a suspension of triazolone 2 (1 equiv.) in DMSO was added K$_2$CO$_3$ (1.6-6.6 equiv.) or Cs$_2$CO$_3$ (1.6-2.0 equiv.), 18-Crown-6 (1 equiv.), and alkyl bromide or alkyl tosylate (1.3-6.0 equiv.). The resulting mixture was stirred at room temperature overnight, followed by the dilution with water and the extraction with CH$_2$Cl$_2$. The combined organic layer was dried (Na$_2$SO$_4$), filtered, and concentrated to yield the crude product, which was purified by column chromatography.

De-methylation of the phenolic methoxy group: The suspension of compound 4a-4-n (1 equiv.) in 48% aqueous HBr was heated to reflux for 6 h. After cooling to room temperature, the solution was neutralized with saturated aqueous Na$_2$CO$_3$ and extracted with CH$_2$Cl$_2$. The combined organic layer was dried (Na$_2$SO$_4$), filtered, and concentrated to yield the product. Unless otherwise stated, the resulted product was used directly for the next coupling reaction without any purification.

Removal of the methoxymethoxy (MOM) protecting group: To a solution of compound 14a-14c (1 equiv.) in CH$_2$Cl$_2$ was added trifluoroacetic acid (TFA) in large excess. The resulting mixture was stirred at room temperature and monitored by TLC. Once the reaction was over, the solution was neutralized with saturated aqueous $Na_2CO_3$ and extracted with $CH_2Cl_2$. The combined organic layer was dried ($Na_2SO_4$), filtered, and concentrated to yield the product. Unless otherwise stated, the resulted product was used directly for the next coupling reaction without any purification.

Synthesis of diazirine: To a 100 mL thick wall pressure vessel containing a ketone compound (1 equiv.) in an ice bath was added 7N ammonia in methanol (MeOH) (7 equiv.). After the vessel was sealed, the reaction mixture was stirred at 0° C. for 4 h. Hydroxylamine O-Sulfonic acid (1.15 equiv.) was dissolved in methanol and then added drop-wise into the reaction mixture. After stirring overnight, most ammonia was removed by gently blowing air through the suspension using a glass pipette, and then the white precipitate was filtered off. After solvents were removed under vacuum, the residue was re-dissolved in methanol followed by the addition of triethylamine (1.5 equiv.). Subsequently, the solution was cooled to 0° C., and iodine was slowly added until the color of iodine persists for 1 min. After 2 h, methanol was evaporated and the reaction mixture was extracted with ether and dried ($Na_2SO_4$), filtered, and concentrated to yield the crude product, which was used directly for the next reaction without any purification.

1-(4-(Methoxymethoxy)phenyl)-4-(4-nitrophenyl)piperazine (11): To a mixture of 10 (263.4 mg, 0.88 mmol) and diisopropylamine (DIPEA) (170.6 mg, 1.32 mmol) in $CH_2Cl_2$ (12 mL) was added slowly chloromethyl methyl ether (77.9 mg, 0.97 mmol) at room temperature. The reaction was stirred for 16 h, and then quenched by the addition of saturated aqueous ammonium chloride (10 mL). The resulting solution was extracted with more $CH_2O_2$, dried ($Na_2SO_4$), filtered, and concentrated to yield the crude product, which was purified by column chromatography (neat $CH_2Cl_2 \rightarrow 100:1$ $CH_2Cl_2$-Acetone) to afford 11 (250.8 mg, 83%) as a yellow amorphous solid; $^1H$ NMR (400 MHz, $CDCl_3$, $\delta_H$) 8.20-8.08 (m, 2H), 7.07-6.97 (m, 2H), 6.97-6.82 (m, 4H), 5.13 (s, 2H), 3.62-3.51 (m, 4H), 3.48 (s, 3H), 3.30-3.18 (m, 4H); $^{13}C$ NMR (100 MHz, $CDCl_3$, $\delta_C$) 154.99, 151.98, 146.31, 138.84, 126.18, 118.59, 117.58, 113.04, 95.28, 56.13, 50.42, 47.43. MALDI-MS: 344.2 (M+H+), 366.2 (M+Na+).

4-(4-(Methoxymethoxy)phenyl)piperazin-1-yl)aniline (12): The nitro group in 11 (250.8 mg, 0.73 mmol) was reduced in the presence of 10% Pd/C (46.8 mg, 5% mole ratio) and hydrazine monohydrate (365.4 mg, 7.3 mmol) in EtOH (10 mL) at reflux. Once the starting material was fully consumed (about 3.5 h), the reaction mixture was filtered through a Celite pad and concentrated to afford 12 as white amorphous solid (226.5 mg, 99%), which was used directly for the next step without any purification: $^1H$ NMR (400 MHz, $CDCl_3$, $\delta_H$) 7.07-6.81 (m, 6H), 6.72-6.63 (m, 2H), 5.13 (s, 2H), 3.49 (d, J=1.3 Hz, 3H), 3.46-3.34 (m, 2H), 3.22 (qd, J=7.1, 3.1 Hz, 8H); $^{13}C$ NMR (100 MHz, $CDCl_3$, $\delta_C$) 151.53, 146.97, 144.63, 140.64, 119.05, 118.30, 117.51, 116.43, 95.36, 56.10, 51.45, 50.93. MALDI-MS: 314.2 (M+H+), 336.2 (M+Na+).

4-(4-(4-(Methoxymethoxy)phenyl)piperazin-1-yl)phenyl)-1H-1,2,4-triazol-5(4H)-one (13): To a solution of 12 (349.1 mg, 1.11 mmol) and pyridine (131.7 mg, 1.67 mmol) in $CH_3CN$ (5 mL), phenyl chloroformate (191.9 mg, 1.23 mmol) was dropwise added at 0° C. The reaction mixture was allowed to warm to room temperature overnight. Then water (10 mL) was added and the mixture was stirred for 30 min. The precipitated light gray solid was filtered, washed with acetonitrile, and then dried under vacuum to obtain the carbamate intermediate (428.3 mg, 89%). To a suspension of carbamate (268.8 mg, 0.62 mmol) in 1,4-dioxane (5 mL) was added hydrazine monohydrate (170.7 mg, 3.41 mmol). The resulting mixture was heated to reflux for 4 h, cooled down to room temperature, and then diluted with water. The precipitate was filtered, washed with acetonitrile, and then dried under vacuum to obtain the hydrazinecarboxamide intermediate (142.1 mg, 62%) as a light orange solid. The mixture of hydrazinecarboxamide (74.5 mg, 0.20 mmol) and formamidine acetate (114.5 mg, 1.10 mmol) in 1-propanol (3 mL) was heated to reflux for 3 h. After cooling to room temperature, the reaction mixture was diluted with water. The solid was filtered, washed with 50% aqueous 1-propanol, and then dried under vacuum to give 13 (44.1 mg, 63%) as an off-white amorphous solid: $^1H$ NMR (400 MHz, $CDCl_3$, $\delta_H$) 11.86 (s, 1H), 8.23 (s, 1H), 7.46 (d, J=9.0 Hz, 2H), 7.08 (d, J=9.1 Hz, 2H), 6.93 (d, J=2.2 Hz, 4H), 5.07 (s, 2H), 3.34 (s, 3H), 3.31-3.24 (m, 4H), 3.18-3.13 (m, 4H). MALDI-MS: 382.2 (M+H+), 404.2 (M+Na+).

4-(4-(4-(4-Methoxyphenyl)piperazin-1-yl)phenyl)-1-methyl-1H-1,2,4-triazol-5(4H)-one (4a). This compound was synthesized as an off-white amorphous solid from 2 (99.7 mg, 0.284 mmol), methyl tosylated 3a (68.6 mg, 0.369 mmol), $Cs_2CO_3$ (148.0 mg, 0.454 mmol), and 18-Crown-6 (75.0 mg, 0.284 mmol) in 21% yield by following general procedure 1.3: $^1H$ NMR (400 MHz, $CDCl_3$, $\delta_H$) 7.60 (s, 1H), 7.45-7.34 (m, 2H), 7.07-6.83 (m, 6H), 3.78 (s, 3H), 3.53 (s, 3H), 3.40-3.32 (m, 4H), 3.28-3.19 (m, 4H); $^{13}C$ NMR (100 MHz, $CDCl_3$, $\delta_C$) 154.40, 152.61, 150.93, 145.66, 134.23, 125.90, 123.90, 118.83, 116.85, 114.73, 55.80, 51.02, 49.42, 32.90. MALDI-MS: 366.2 (M+H+), 388.2 (M+Na+).

4-(4-(4-(4-Hydroxyphenyl)piperazin-1-yl)phenyl)-1-methyl-1H-1,2,4-triazol-5(4H)-one (5a). This compound was synthesized as a white amorphous solid from 4a (21.8 mg, 0.060 mmol) in 48% aqueous HBr (1 mL) in 96% yield by following general procedure 1.4: MALDI-MS: 352.2 (M+H+), 374.2 (M+Na+).

1-Ethyl-4-(4-(4-(4-methoxyphenyl)piperazin-1-yl)phenyl)-1H-1,2,4-triazol-5(4H)-one (4b). This compound was synthesized as an off-white amorphous solid from 2 (60.0 mg, 0.171 mmol), ethyl tosylated 3b (44.5 mg, 0.222 mmol), $K_2CO_3$ (37.8 mg, 0.273 mmol), and 18-Crown-6 (45.2 mg, 0.171 mmol) in 32% yield by following general procedure 1.3: $^1H$ NMR (400 MHz, $CDCl_3$, $\delta_H$) 7.61 (s, 1H), 7.40 (d, J=8.9 Hz, 2H), 7.08-6.92 (m, 4H), 6.92-6.82 (m, 2H), 3.91 (q, J=12 Hz, 2H), 3.78 (s, 3H), 3.36 (dd, J=6.2, 3.8 Hz, 4H), 3.23 (dd, J=6.2, 3.8 Hz, 4H), 1.39 (t, J=7.2 Hz, 3H); $^{13}C$ NMR (100 MHz, $CDCl_3$, $\delta_C$) 154.40, 152.10, 150.85, 145.65, 134.25, 125.99, 123.86, 118.84, 116.85, 114.73, 55.79, 51.02, 49.43, 40.78, 14.11. MALDI-MS: 380.2 (M+H+), 402.2 (M+Na+).

1-Ethyl-4-(4-(4-(4-Hydroxyphenyl)piperazin-1-yl)phenyl)-1H-1,2,4-triazol-5(4H)-one (5b). This compound was synthesized as a white amorphous solid from 4b (20.9 mg, 0.055 mmol) in 48% aqueous HBr (1 mL) in 93% yield by following general procedure 1.4: MALDI-MS: 366.2 (M+H+), 388.2 (M+Na+).

4-(4-(4-(4-Methoxyphenyl)piperazin-1-yl)phenyl)-1-propyl-1H-1,2,4-triazol-5(4H)-one (4c). This compound was synthesized as a yellowish amorphous solid from 2 (69.5 mg, 0.198 mmol), 1-bromopropane 3c (38.9 mg, 0.316 mmol), $K_2CO_3$ (54.7 mg, 0.396 mmol), and 18-Crown-6 (52.3 mg, 0.198 mmol) in 69% yield by following general procedure 1.3: $^1H$ NMR (400 MHz, $CDCl^3$, $\delta_H$) 7.60 (s, 1H), 7.51-7.36 (m, 2H), 7.07-6.92 (m, 4H), 6.92-6.80 (m, 2H), 3.83-3.78 (m, 2H), 3.76 (s, 3H), 3.39-3.32 (m, 4H), 3.25-3.18 (m, 4H), 1.93-1.72 (m, 2H), 0.97 (t, J=7.4 Hz, 3H); $^{13}C$ NMR (100 MHz, $CDCl_3$, $\delta_C$) 154.48, 152.39, 150.78, 145.48, 134.17, 126.06, 123.77, 118.88, 116.86, 114.73, 55.78, 51.08, 49.40, 47.40, 22.27, 11.35. MALDI-MS: 394.2 (M+H$^+$) 416.2 (M+Na$^+$).

4-(4-(4-(4-Hydroxyphenyl)piperazin-1-yl)phenyl)-1-propyl-1H-1,2,4-triazol-5(4H)-one (5c). This compound was synthesized as a white amorphous solid from 4c (53.6 mg, 0.136 mmol) in 48% aqueous HBr (1.5 mL) in 97% yield by following general procedure 1.4: $^1$H NMR (400 MHz, CDCl$_3$, $\delta_H$) 7.62 (s, 1H), 7.38 (d, J=8.6 Hz, 2H), 7.06-6.90 (m, 4H), 6.74 (d, J=8.4 Hz, 2H), 3.83 (t, J=7.1 Hz, 2H), 3.37-3.31 (m, 4H), 3.24-3.18 (m, 4H), 1.83 (dd, J=14.5, 7.2 Hz, 2H), 0.98 (t, J=7.3 Hz, 3H). MALDI-MS: 380.2 (M+H$^+$), 402.2 (M+Na$^+$).

1-Isopropyl-4-(4-(4-(4-methoxyphenyl)piperazin-1-yl)phenyl)-1H-1,2,4-triazol-5(4H)-one (4d). This compound was synthesized as a yellowish amorphous solid from 2 (60.0 mg, 0.171 mmol), isopropyl tosylate 3d (47.6 mg, 0.222 mmol), K$_2$CO$_3$ (37.8 mg, 0.273 mmol), and 18-Crown-6 (45.2 mg, 0.171 mmol) in 47% yield by following general procedure 1.3: $^1$H NMR (400 MHz, CDCl$_3$, $\delta_H$) 7.60 (s, 1H), 7.41 (d, J=8.4 Hz, 2H), 7.11-6.83 (m, 6H), 4.56 (dt, J=13.4, 6.7 Hz, 1H), 3.78 (d, J=0.8 Hz, 3H), 3.47-3.31 (m, 4H), 3.30-3.15 (m, 4H), 1.41 (d, J=6.7 Hz, 6H); $^{13}$C NMR (100 MHz, CDCl$_3$, $\delta_C$) 154.39, 151.67, 150.81, 145.69, 134.13, 126.03, 123.86, 118.82, 116.84, 114.73, 55.79, 51.01, 49.46, 47.17, 21.40. MALDI-MS: 394.2 (M+H$^+$), 416.2 (M+Na$^+$).

4-(4-(4-(4-Hydroxyphenyl)piperazin-1-yl)phenyl)-1-isopropyl-1H-1,2,4-triazol-5(4H)-one (5d). This compound was synthesized as a white amorphous solid from 4d (31.6 mg, 0.080 mmol) in 48% aqueous HBr (1.0 mL) in 96% yield by following general procedure 1.4: MALDI-MS: 380.2 (M+H$^+$), 402.2 (M+Na$^+$).

1-Butyl-4-(4-(4-(4-methoxyphenyl)piperazin-1-yl)phenyl)-1H-1,2,4-triazol-5(4H)-one (4e). This compound was synthesized as a yellowish amorphous solid from 2 (132.0 mg, 0.376 mmol), 1-bromobuane 3e (82.4 mg, 0.601 mmol), K$_2$CO$_3$ (103.9 mg, 0.752 mmol), and KI (31.2 mg, 0.188 mmol) in 73% yield by following general procedure 1.2: $^1$H NMR (400 MHz, CDCl$_3$, $\delta_H$) 7.60 (s, 1H), 7.47-7.35 (m, 2H), 7.07-6.81 (m, 6H), 3.85 (t, J=7.2 Hz, 2H), 3.78 (s, 3H), 3.36 (dd, J=6.3, 3.8 Hz, 4H), 3.22 (dd, J=6.3, 3.8 Hz, 4H), 1.78 (dq, J=12.7, 7.6 Hz, 2H), 1.40 (dq, J=14.7, 7.4 Hz, 2H), 0.96 (t, J=7.4 Hz, 3H); $^{13}$C NMR (100 MHz, CDCl$_3$, $\delta_C$) 154.40, 152.35, 150.84, 145.69, 134.13, 126.05, 123.78, 118.83, 116.85, 114.73, 55.79, 51.01, 49.46, 45.55, 30.92, 20.02, 13.89. MALDI-MS: 408.2 (M+H$^+$), 430.2 (M+Na$^+$).

1-Butyl-4-(4-(4-(4-hydroxyphenyl)piperazin-1-yl)phenyl)-1H-1,2,4-triazol-5(4H)-one (5e). This compound was synthesized as a white amorphous solid from 4e (144.6 mg, 0.355 mmol) in 48% aqueous HBr (3.0 mL) in 99% yield by following general procedure 1.4: $^1$H NMR (400 MHz, CDCl$_3$, $\delta_H$) 7.61 (s, 1H), 7.40 (d, J=9.0 Hz, 2H), 7.02 (d, J=9.0 Hz, 2H), 6.90 (d, J=8.9 Hz, 2H), 6.79 (d, J=8.9 Hz, 2H), 4.58 (s, 1H), 3.85 (t, J=7.2 Hz, 2H), 3.36 (dd, J=6.2, 3.9 Hz, 4H), 3.22 (dd, J=6.2, 3.9 Hz, 4H), 1.78 (dt, J=12.7, 7.5 Hz, 2H), 1.40 (td, J=14.9, 7.5 Hz, 2H), 0.96 (t, J=7.4 Hz, 3H). MALDI-MS: 394.2 (M+H$^+$), 416.2 (M+Na$^+$).

1-Isobutyl-4-(4-(4-(4-methoxyphenyl)piperazin-1-yl)phenyl)-1H-1,2,4-triazol-5(4H)-one (4f). This compound was synthesized as a yellowish amorphous solid from 2 (60.0 mg, 0.171 mmol), 1-bromo-2-methylpropane 3f (30.4 mg, 0.222 mmol), K$_2$CO$_3$ (42.5 mg, 0.308 mmol), and KI (8.5 mg, 0.051 mmol) in 67% yield by following general procedure 1.2: $^1$H NMR (400 MHz, CDCl$_3$, $\delta_H$) 7.62 (s, 1H), 7.47-7.36 (m, 2H), 7.09-6.76 (m, 6H), 3.78 (s, 3H), 3.66 (d, J=12 Hz, 2H), 3.35 (dd, J=6.2, 3.8 Hz, 4H), 3.22 (dd, J=6.2, 18 Hz, 4H), 2.20 (dt, J=13.6, 6.8 Hz, 1H), 0.98 (d, J=6.8 Hz, 6H); $^{13}$C NMR (100 MHz, CDCl$_3$, $\delta_C$) 154.38, 152.63, 150.81, 145.68, 134.07, 126.08, 123.70, 118.82, 116.85, 114.72, 55.79, 53.03, 51.00, 49.46, 28.47, 20.14. MALDI-MS: 408.2 (M+H$^+$), 430.2 (M+Na$^+$).

4-(4-(4-(4-Hydroxyphenyl)piperazin-1-yl)phenyl)-1-isobutyl-1H-1,2,4-triazol-5(4H)-one (5l). This compound was synthesized as a white amorphous solid from 4f (64.0 mg, 0.152 mmol) in 48% aqueous HBr (1.5 mL) in 91% yield by following general procedure 1.4: MALDI-MS: 394.2 (M+H$^+$), 416.2 (M+Na$^+$).

4-(4-(4-(4-Methoxyphenyl)piperazin-1-yl)phenyl)-1-pentyl-1H-1,2,4-triazol-5(4H)-one (4g). This compound was synthesized as a yellowish amorphous solid from 2 (64.4 mg, 0.183 mmol), 1-bromopentane 3g (44.3 mg, 0.293 mmol), K$_2$CO$_3$ (50.6 mg, 0.366 mmol), and KI (9.1 mg, 0.055 mmol) in 53% yield by following general procedure 1.2: $^1$H NMR (400 MHz, CDCl$_3$, $\delta_H$) 7.61 (s, 1H), 7.41 (d, J=8.9 Hz, 2H), 7.08-6.92 (m, 4H), 6.92-6.81 (m, 2H), 3.83 (t, J=7.2 Hz, 2H), 3.77 (s, 3H), 3.42-3.31 (m, 4H), 3.22 (dd, J=6.0, 3.8 Hz, 4H), 1.90-1.72 (m, 2H), 1.41-1.32 (m, 4H), 0.90 (t, J=6.9 Hz, 3H); $^{13}$C NMR (100 MHz, CDCl$_3$, $\delta_C$) 154.40, 152.32, 150.81, 145.63, 134.14, 126.05, 123.76, 118.84, 116.85, 114.72, 55.78, 51.02, 49.44, 45.83, 28.93, 28.59, 22.51, 14.22. MALDI-MS: 422.2 (M+H$^+$), 444.2 (M+Na$^+$).

4-(4-(4-(4-Hydroxyphenyl)piperazin-1-yl)phenyl)-1-pentyl-1H-1,2,4-triazol-5(4H)-one (5g). This compound was synthesized as a white amorphous solid from 4g (43.4 mg, 0.103 mmol) in 48% aqueous HBr (1.0 mL) in 89% yield by following general procedure 1.4: $^1$H NMR (400 MHz, CDCl$_3$, $\delta_H$) 7.62 (s, 1H), 7.40 (t, J=10.1 Hz, 2H), 7.05-6.94 (m, 4H), 6.75 (d, J=8.5 Hz, 2H), 3.85 (t, J=7.2 Hz, 2H), 3.48-3.40 (m, 4H), 3.43-3.35 (m, 4H), 1.90-1.72 (m, 2H), 1.40-1.33 (m, 4H), 0.91 (t, J=6.9 Hz, 3H). MALDI-MS: 408.2 (M+H$^+$), 430.2 (M+Na$^+$).

2-Pentyl tosylate (3h). This compound was synthesized as a colorless oil from 2-pentanol (122.0 mg, 1.384 mmol), TsCl (316.6 mg, 1.66 mmol), Et$_3$N (280.3 mg, 2.77 mmol), and DMAP (169.0 mg, 1.384 mmol) in 92% yield by following general procedure 1.1: $^1$H NMR (400 MHz, CDCl$_3$; $\delta_H$) 7.75 (d, J=8.3 Hz, 2H), 7.30 (d, J=8.3 Hz, 2H), 4.63-4.51 (m, 1H), 2.40 (s, 3H), 1.56 (dddd, J=14.0, 10.0, 7.2, 5.4 Hz, 1H), 1.49-1.35 (m, 1H), 1.35-1.04 (m, 5H), 0.77 (t, J=1A Hz, 3H); $^{13}$C NMR (100 MHz, CDCl$_3$, $\delta_C$) 144.57, 134.63, 129.84, 127.78, 80.55, 38.70, 21.73, 20.90, 18.28, 13.74. ESI-MS: 243.1 (M+H$^+$), 265.1 (M+Na$^+$).

4-(4-(4-(4-Methoxyphenyl)piperazin-1-yl)phenyl)-1-(pentan-2-yl)-1H-1,2,4-triazol-5(4H)-one (4h). This compound was synthesized as a yellowish amorphous solid from 2 (70.0 mg, 0.199 mmol), 3h (79.5 mg, 0.328 mmol), K$_2$CO$_3$ (55.0 mg, 0.398 mmol), and 18-Crown-6 (52.6 mg, 0.199 mmol) in 57% yield by following general procedure 1.3: $^1$H NMR (400 MHz, CDCl$_3$, $\delta_H$) 7.61 (s, 1H), 7.41 (d, J=8.6 Hz, 2H), 7.06-6.91 (m, 4H), 6.86 (d, J=8.8 Hz, 2H), 4.44-4.33 (m, 1H), 3.77 (s, 3H), 3.46-3.30 (m, 4H), 3.31-3.15 (m, 4H), 1.93-1.77 (m, 1H), 1.72-1.53 (m, 1H), 1.46-1.18 (m, 5H), 0.92 (t, J=7.3 Hz, 3H); $^{13}$C NMR (100 MHz, CDCl$_3$, $\delta_C$) 154.52, 152.13, 150.72, 145.43, 134.16, 126.15, 123.73, 118.91, 116.88, 114.74, 55.78, 51.10, 51.06, 49.43, 37.69, 19.88, 19.71, 14.01. MALDI-MS: 422.2 (M+H), 444.2 (M+Na$^+$).

4-(4-(4-(4-Hydroxyphenyl)piperazin-1-yl)phenyl)-1-pentyl-1H-1,2,4-triazol-5(4H)-one (5h). This compound was synthesized as a white amorphous solid from 4h (41.1 mg, 0.098 mmol) in 48% aqueous HBr (1.0 mL) in 97% yield by following general procedure 1.4: $^1$H NMR (400 MHz, CDCl$_3$, $\delta_H$) 7.62 (s, 1H), 7.36 (d, J=8.4 Hz, 2H), 6.95 (d, J=8.5 Hz, 2H), 6.83 (d, J=8.4 Hz, 2H), 6.68 (d, J=8.5 Hz, 2H), 4.52-4.28 (m, 1H), 3.39-3.28 (m, 4H), 3.25-3.14 (m, 4H), 1.94-1.78 (m, 1H), 1.64 (ddd, J=19.7, 12.6, 5.8 Hz, 1H), 1.44-1.23 (m, 5H), 0.92 (t, J=7.3 Hz, 3H); $^{13}$C NMR (100 MHz, CDCl$_3$, $\delta_C$) 152.47, 151.60, 150.98, 144.38, 134.64, 125.52, 124.54, 119.17, 116.75, 116.28, 51.48, 51.42, 49.20, 37.67, 19.87, 19.70, 14.00. MALDI-MS: 408.2 (M+H$^+$), 430.2 (M+Na$^+$).

1-Isopentyl-4-(4-(4-(4-methoxyphenyl)piperazin-1-yl)phenyl)-1H-1,2,4-triazol-5(4B)-one (4i). This compound was synthesized as a yellowish amorphous solid from 2 (64.6 mg, 0.184 mmol), 1-bromo-3-methylbutane 3i (47.2 mg, 0.313 mmol), K$_2$CO$_3$ (50.8 mg, 0.368 mmol), and KI (15.3 mg, 0.092 mmol) in 56% yield by following general procedure 1.2: $^1$H NMR (400 MHz, CDCl$_3$, $\delta_H$) 7.61 (s, 1H), 7.40 (d, J=8.9 Hz, 2H), 6.99 (dd, J=20.1, 8.9 Hz, 4H), 6.86 (d, J=9.0 Hz, 2H), 3.87 (d, J=7.1 Hz, 2H), 3.77 (s, 3H), 3.43-3.31 (m, 4H), 3.28-3.14 (d, J=4.6 Hz, 4H), 1.70-1.62 (m, 3H), 0.96 (d, J=6.2 Hz, 6H); $^{13}$C NMR (100 MHz, CDCl$_3$, $\delta_C$) 154.47, 152.26, 150.78, 145.53, 134.14, 126.07, 123.75, 118.89, 116.87, 114.72, 55.78, 51.08, 49.41, 44.18, 37.57, 25.81, 22.62. MALDI-MS: 422.2 (M+H$^+$), 444.2 (M+Na$^+$).

4-(4-(4-(4-Hydroxyphenyl)piperazin-1-yl)phenyl)-1-isopentyl-1H-1,2,4-triazol-5(4H)-one (5i). This compound was synthesized as a white amorphous solid from 4i (43.4 mg, 0.103 mmol) in 48% aqueous HBr (1.0 mL) in 95% yield by following general procedure 1.4: $^1$H NMR (400 MHz, CDCl$_3$, $\delta_H$) 7.61 (s, 1H), 7.37 (d, J=8.7 Hz, 2H), 7.02-6.91 (m, 4H), 6.73 (d, J=8.4 Hz, 2H), 3.91-3.83 (m, 2H), 3.44-3.35 (m, 4H), 3.29-3.20 (m, 4H), 1.76-1.63 (m, 3H), 0.96 (d, J=5.6 Hz, 6H). MALDI-MS: 408.2 (M+H$^+$), 430.2 (M+Na$^+$).

4-(4-(4-(4-Methoxyphenyl)piperazin-1-yl)phenyl)-1-(pentan-3-yl)-1H-1,2,4-triazol-5(4H)-one (4j). This compound was synthesized as a yellowish amorphous solid from 2 (62.0 mg, 0.176 mmol), 3-bromopentane 3j (45.3 mg, 0.300 mmol), K$_2$CO$_3$ (48.8 mg, 0.353 mmol), and KI (14.6 mg, 0.088 mmol) in 56% yield by following general procedure 1.2: $^1$H NMR (400 MHz, CDCl$_3$, $\delta_H$) 7.64 (s, 1H), 7.53-7.39 (m, 2H), 7.07-6.93 (m, 4H), 6.93-6.81 (m, 2H), 4.14-3.97 (m, 1H), 3.77 (s, 3H), 3.45-3.30 (m, 4H), 3.30-3.13 (m, 4H), 1.94-1.62 (m, 4H), 0.88 (t, J=7.4 Hz, 6H); $^{13}$C NMR (100 MHz, CDCl$_3$, $\delta_C$) 154.55, 153.02, 150.69, 145.42, 134.20, 126.24, 123.64, 118.94, 116.91, 114.74, 58.99, 55.79, 51.14, 49.44, 27.00, 10.98. MALDI-MS: 422.2 (M+H$^+$), 444.2 (M+Na$^+$).

4-(4-(4-(4-Hydroxyphenyl)piperazin-1-yl)phenyl)-1-(pentan-3-yl)-1H-1,2,4-triazol-5(4H)-one (5j). This compound was synthesized as a white amorphous solid from 4j (41.5 mg, 0.099 mmol) in 48% aqueous HBr (1.0 mL) in 98% yield by following general procedure 1.4: $^1$H NMR (400 MHz, CDCl$_3$, $\delta_H$) 7.64 (s, 1H), 7.40 (d, J=8.9 Hz, 2H), 7.04-6.92 (m, 4H), 6.72 (d, J=8.5 Hz, 2H), 4.15-3.97 (m, 1H), 3.42-3.31 (m, 4H), 3.29-3.18 (m, 4H), 1.95-1.62 (m, 4H), 0.89 (t, J=7.4 Hz, 6H); $^{13}$C NMR (100 MHz, CDCl$_3$, $\delta_C$) 153.31, 151.93, 150.78, 143.66, 134.54, 125.92, 124.36, 119.46, 116.94, 116.36, 59.27, 51.82, 49.09, 26.99, 10.97. MALDI-MS: 408.2 (M+H$^+$), 430.2 (M+Na$^+$).

1-Cyclohexyl-4-(4-(4-(4-methoxyphenyl)piperazin-1-yl)phenyl)-1H-1,2,4-triazol-5(4H)-one (4k). This compound was synthesized as a yellowish amorphous solid from 2 (70.3 mg, 0.20 mmol), cyclohexyl bromide 3k (195.7 mg, 1.20 mmol), K$_2$CO$_3$ (182.4 mg, 1.32 mmol), and 18-Crown-6 (52.9 mg, 0.20 mmol) in 24% yield by following general procedure 1.3: $^1$H NMR (400 MHz, CDCl$_3$, $\delta_H$) 7.59 (s, 1H), 7.50-7.36 (m, 2H), 7.09-7.01 (m, 2H), 7.01-6.92 (m, 2H), 6.92-6.80 (m, 2H), 4.15 (tt, J=11.8, 3.9 Hz, 1H), 3.78 (s, 3H), 3.37 (dd, J=6.2, 3.7 Hz, 4H), 3.23 (dd, J=6.2, 3.7 Hz, 4H), 2.03-1.65 (m, 7H), 1.51-1.34 (m, 2H), 1.34-1.16 (m, 1H); $^{13}$C NMR (100 MHz, CDCl$_3$, $\delta_C$) 154.38, 151.75, 150.81, 145.68, 134.03, 126.06, 123.89, 118.83, 116.86, 114.72, 55.80, 54.34, 51.03, 49.47, 31.70, 25.66, 25.46. MALDI-MS: 434.2 (M+H$^+$), 456.2 (M+Na$^+$).

1-Cyclohexyl-4-(4-(4-(4-hydroxyphenyl)piperazin-1-yl)phenyl)-1H-1,2,4-triazol-5(4H)-one (5k). This compound was synthesized as a white amorphous solid from 4k (24.2 mg, 0.056 mmol) in 48% aqueous HBr (1.0 mL) in 92% yield by following general procedure 1.4: MALDI-MS: 420.2 (M+H$^+$), 442.2 (M+Na$^+$).

Cyclopentylmethyl tosylate (3l). This compound was synthesized as a colorless oil from cyclopentylmethanol (235.0 mg, 2.35 mmol), TsCl (581.5 mg, 3.05 mmol), Et$_3$N (473.2 mg, 4.70 mmol), and DMAP (287.1 mg, 2.35 mmol) in 95% yield by following general procedure 1.1: $^1$H NMR (400 MHz, CDCl$_3$, $\delta_H$) 7.77 (d, J=8.2 Hz, 2H), 7.33 (d, J=8.4 Hz, 2H), 3.88 (d, J=7.1 Hz, 2H), 2.44 (s, 3H), 2.18 (dt, J=15.0, 7.5 Hz, 1H), 1.80-1.62 (m, 2H), 1.62-1.41 (m, 4H), 1.25-1.09 (m, 2H); $^{13}$C NMR (100 MHz, CDCl$_3$, $\delta_C$) 144.83, 133.40, 130.02, 128.07, 74.51, 38.79, 29.19, 25.45, 21.86. ESI-MS: 255.1 (M+H$^+$), 277.1 (M+Na$^+$).

1-(Cyclopentylmethyl)-4-(4-(4-(4-methoxyphenyl)piperazin-1-yl)phenyl)-1H-1,2,4-triazol-5(4H)-one (4l). This compound was synthesized as a yellowish amorphous solid from 2 (50.0 mg, 0.142 mmol), 3l (54.2 mg, 0.213 mmol), K$_2$CO$_3$ (39.3 mg, 0.285 mmol), and KI (11.8 mg, 0.071 mmol) in 59% yield by following general procedure 1.2: $^1$H NMR (400 MHz, CDCl$_3$, $\delta_H$) 7.61 (s, 1H), 7.50-7.36 (m, 2H), 7.08-6.91 (m, 4H), 6.89-6.81 (m, 2H), 3.80-3.73 (m, 5H), 3.35 (dd, J=6.3, 3.8 Hz, 4H), 3.22 (dd, J=6.3, 3.8 Hz, 4H), 2.49-2.39 (m, 1H), 1.83-1.49 (m, 6H), 1.42-1.28 (m, 2H); $^{13}$C NMR (100 MHz, CDCl$_3$, $\delta_C$) 154.38, 152.51, 150.80, 145.67, 134.01, 126.09, 123.71, 118.83, 116.85, 114.72, 55.79, 51.01, 50.52, 49.47, 39.54, 30.36, 25.31. MALDI-MS: 434.2 (M+H$^+$), 456.2 (M+Na$^+$).

1-(Cyclopentylmethyl)-4-(4-(4-(4-hydroxyphenyl)piperazin-1-yl)phenyl)-1H-1,2,4-triazol-5(4H)-one (5l). This compound was synthesized as a white amorphous solid from 4l (36.2 mg, 0.084 mmol) in 48% aqueous HBr (1.0 mL) in 94% yield by following general procedure 1.4: MALDI-MS: 420.2 (M+H), 442.2 (M+Na$^+$).

4-(4-(4-(4-Methoxyphenyl)piperazin-1-yl)phenyl)-1-octyl-1H-1,2,4-triazol-5(4H)-one (4m). This compound was synthesized as a yellowish amorphous solid from 2 (55.0 mg, 0.157 mmol), 1-bromooctane 3m (39.3 mg, 0.203 mmol), K$_2$CO$_3$ (43.4 mg, 0.314 mmol), and KI (13.0 mg, 0.078 mmol) in 69% yield by following general procedure 1.2: $^1$H NMR (400 MHz, CDCl$_3$, $\delta_H$) 7.61 (s, 1H), 7.47-7.35 (m, 2H), 7.07-6.99 (m, 2H), 6.99-6.94 (m, 2H), 6.94-6.85 (m, 2H), 3.89-3.80 (m, 2H), 3.78 (s, 3H), 3.35 (dd, J=6.2, 3.8 Hz, 4H), 3.22 (dd, J=6.2, 3.8 Hz, 4H), 1.88-1.71 (m, 2H), 1.49-1.14 (m, 10H), 0.88 (t, J=6.9 Hz, 3H); $^{13}$C NMR (100 MHz, CDCl$_3$, $\delta_C$) 154.38, 152.32, 150.82, 145.68, 134.13, 126.05, 123.76, 118.82, 116.84, 114.72, 55.78, 51.01, 49.45, 45.87, 32.01, 29.39, 28.89, 26.80, 22.87, 14.35. MALDI-MS: 464.3 (M+H$^+$), 486.3 (M+Na$^+$).

4-(4-(4-(4-Hydroxyphenyl)piperazin-1-yl)phenyl)-1-octyl-1H-1,2,4-triazol-5(4H)-one (5m). This compound was synthesized as a white amorphous solid from 4m (50.2 mg, 0.108 mmol) in 48% aqueous HBr (1.0 mL) in 95% yield by following general procedure 1.4: MALDI-MS: 450.3 (M+H$^+$), 472.3 (M+Na$^+$).

6-Phenylhexyl tosylate (3n). This compound was synthesized as a colorless oil from 6-phenylhexan-1-ol (137.0 mg, 0.77 mmol), TsCl (190.7 mg, 1.00 mmol), Et$_3$N (155.0 mg, 1.54 mmol), and DMAP (93.8 mg, 0.77 mmol) in 81% yield by following general procedure 1.1: $^1$H NMR (400 MHz, CDCl$_3$, $\delta_H$) 7.87-7.77 (m, 2H), 7.35 (d, J=8.0 Hz, 2H), 7.33-7.24 (m, 2H), 7.23-7.13 (m, 3H), 4.03 (t, J=6.5 Hz, 2H), 2.65-2.53 (m, 2H), 2.45 (s, 3H), 1.75-1.50 (m, 4H), 1.45-1.19 (m, 4H); $^{13}$C NMR (100 MHz, CDCl$_3$, 144.93, 142.73, 133.40, 130.08, 128.60, 128.52, 128.11, 125.92, 70.89, 35.99, 31.44, 28.98, 28.78, 25.47, 21.88. ESI-MS: 333.1 (M+H$^+$), 355.1 (M+Na$^+$).

4-(4-(4-(4-Methoxyphenyl)piperazin-1-yl)phenyl)-1-(6-phenylhexyl)-1H-1,2,4-triazol-5(4H)-one (4n). This compound was synthesized as a yellowish amorphous solid from 2 (56.5 mg, 0.161 mmol), 3n (64.1 mg, 0.193 mmol), K$_2$CO$_3$ (44.5 mg, 0.322 mmol), and KI (8.0 mg, 0.048 mmol) in 61% yield by following general procedure 1.2: $^1$H NMR (400 MHz, CDCl$_3$, $\delta_H$) 7.60 (s, 1H), 7.41 (d, J=8.8 Hz, 2H), 7.32-7.23 (m, 1H), 7.22-7.13 (m, 2H), 7.03 (d, J=8.9 Hz, 2H), 7.00-6.93 (m, 2H), 6.93-6.83 (m, 2H), 3.84 (t, J=7.2 Hz, 2H), 3.79 (s, 3H), 3.37 (dd, J=6.2, 3.8 Hz, 4H), 3.23 (dd, J=6.1, 3.8 Hz, 4H), 2.69-2.52 (m, 2H), 1.89-1.71 (m, 2H), 1.71-1.57 (m, 2H), 1.50-1.33 (m, 4H); $^{13}$C NMR (100 MHz, CDCl$_3$, $\delta_C$) 154.41, 152.34, 150.85, 145.67, 142.89, 134.16, 128.62, 128.46, 126.02, 125.83, 123.80, 118.85, 116.86, 114.74, 55.80, 51.03, 49.46, 45.82, 36.07, 31.52, 29.07, 28.82, 26.66. MALDI-MS: 512.3 (M+H$^+$), 534.3 (M+Na$^+$).

4-(4-(4-(4-Hydroxyphenyl)piperazin-1-yl)phenyl)-1-(6-phenylhexyl)-1H-1,2,4-triazol-5(4H)-one (5n). This compound was synthesized as a white amorphous solid from 4n (27.4 mg, 0.054 mmol) in 48% aqueous HBr (1.0 mL) in 73% yield by following general procedure 1.4: MALDI-MS: 498.3 (M+H$^+$), 520.3 (M+Na$^+$).

Hex-3-ynyl 4-methylbenzenesulfonate (3o). This compound was synthesized as a colorless oil from hex-3-yn-1-ol (117.0 mg, 1.19 mmol), TsCl (295.5 mg, 1.55 mmol), Et$_3$N (181.3 mg, 1.79 mmol), and DMAP (145.6 mg, 1.19 mmol) in 98% yield by following general procedure 1.1: ESI-MS: 253.1 (M+H$^+$), 275.1 (M+Na$^+$).

1-(Hex-3-ynyl)-4-(4-(4-(4-(methoxymethoxy)phenyl)piperazin-1-yl)phenyl)-1H-1,2,4-triazol-5(4H)-one (14a). This compound was synthesized as a yellowish amorphous solid from 13 (56.0 mg, 0.147 mmol), 3o (48.2 mg, 0.191 mmol), K$_2$CO$_3$ (40.6 mg, 0.294 mmol), and 18-Crown-6 (38.9 mg, 0.147 mmol) in 60% yield by following general procedure 1.3: $^1$H NMR (400 MHz, CDCl$_3$, $\delta_H$) 7.61 (s, 1H), 7.45-7.34 (m, 2H), 7.10-6.87 (m, 6H), 5.12 (s, 2H), 3.97 (t, J=7.3 Hz, 2H), 3.47 (s, 3H), 3.35 (dd, J=6.3, 3.6 Hz, 4H), 3.23 (dd, J=6.3, 3.6 Hz, 4H), 2.63 (tt, J=7.3, 2.3 Hz, 2H), 2.14 (qt, J=7.5, 2.3 Hz, 2H), 1.09 (t, J=7.5 Hz, 3H); $^{13}$C NMR (100 MHz, CDCl$_3$, $\delta_C$) 152.25, 151.76, 150.85, 146.67, 134.50, 125.93, 123.81, 118.52, 117.50, 116.85, 95.28, 83.95, 75.42, 56.10, 50.72, 49.39, 45.03, 19.25, 14.34, 12.62. MALDI-MS: 462.2 (M+H$^+$), 484.2 (M+Na$^+$).

1-(Hex-3-yayl)-4-(4-(4-(4-hydroxyphenyl)piperazin-1-yl)phenyl)-1H-1,2,4-triazol-5(4H)-one (5o). This compound was synthesized as a white amorphous solid from 4o (40.8 mg, 0.088 mmol) in 99% yield by following general procedure 1.5: $^1$H NMR (400 MHz, CDCl$_3$, $\delta_H$) 7.61 (s, 1H), 7.44-7.30 (m, 2H), 7.07-6.92 (m, 2H), 6.86 (d, J=8.9 Hz, 2H), 6.72 (d, J=8.9 Hz, 2H), 5.52 (br s, 1H), 3.99 (t, J=7.2 Hz, 2H), 3.42-3.28 (m, 4H), 3.28-3.13 (m, 4H), 2.65 (tt, J=7.2, 2.3 Hz, 2H), 2.15 (qt, J=7.5, 2.3 Hz, 2H), 1.10 (t, J=7.5 Hz, 3H). MALDI-MS: 418.2 (M+H$^+$), 440.2 (M+Na$^+$).

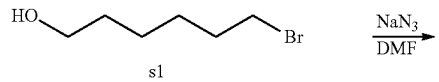

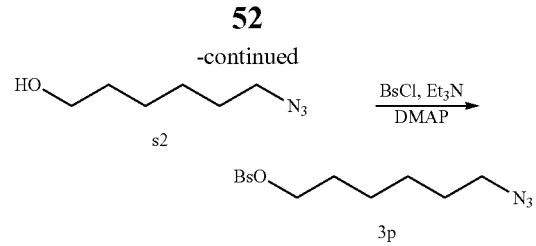

6-Azidohexyl 4-bromobenzenesulfonate (3p). To a flask containing 6-bromo-hexanol s1 (500.0 mg, 2.76 mmol) was added DMF (5.0 mL) followed by sodium azide (500.0 mg, 8.3 mmol). The reaction mixture was heated to 110° C. for 12 h. After cooling to room temperature, the reaction mixture was diluted with water and extracted with ether. The organic layer was combined, dried over Na$_2$SO$_4$, concentrated to yield the crude product, which was purified by column chromatography (10:1→3:1 Hexanes-Ethyl Acetate) to afford s2 (375.6 mg, 95%) as a light yellow oil: $^1$H NMR (400 MHz, CDCl$_3$, $\delta_H$) 3.62 (t, J=6.6 Hz, 2H), 3.25 (t, J=6.9 Hz, 2H), 1.75 (s, 1H), 1.67-1.48 (m, 4H), 1.46-1.30 (m, 4H).

Compound 3p was synthesized as a colorless oil from s2 (463.8 mg, 3.24 mmol), BsCl (1.08 g, 4.21 mmol), Et$_3$N (655.7 mg, 6.48 mmol), and DMAP (197.9 mg, 1.62 mmol) in 79% yield by following general procedure 1.1: $^1$H NMR (400 MHz, CDCl$_3$, $\delta_H$) 7.77 (d, J=8.3 Hz, 2H), 7.70 (d, J=8.3 Hz, 2H), 4.06 (t, J=6.4 Hz, 2H), 3.24 (t, J=6.8 Hz, 2H), 1.73-1.62 (m, 2H), 1.61-1.50 (m, 2H), 1.41-1.29 (m, 4H). ESI-MS: 362.0 (M+H$^+$), 384.0 (M+Na$^+$).

1-(6-Azidohexyl)-4-(4-(4-(4-(methoxymethoxy)phenyl)piperazin-1-yl)phenyl)-1H-1,2,4-triazol-5(4H)-one (14b). This compound was synthesized as a yellowish amorphous solid from 13 (114.4 mg, 0.30 mmol), 3p (130.4 mg, 0.36 mmol), and Cs$_2$CO$_3$ (146.6 mg, 0.45 mmol) in 62% yield by following general procedure 1.2: $^1$H NMR (400 MHz, CDCl$_3$, $\delta_H$) 7.61 (s, 1H), 7.41 (d, J=9.0 Hz, 2H), 7.08-6.93 (m, 6H), 5.13 (s, 2H), 3.85 (t, J=7.1 Hz, 2H), 3.48 (s, 3H), 3.41-3.33 (m, 4H), 3.31-3.22 (m, 6H), 1.88-1.74 (m, 2H), 1.61 (dt, J=14.0, 7.0 Hz, 2H), 1.52-1.35 (m, 4H). ESI-MS: 507.3 (M+H$^+$), 529.3 (M+Na$^+$).

1-(6-Azidohexyl)-4-(4-(4-(4-hydroxyphenyl)piperazin-1-yl)phenyl)-1H-1,2,4-triazol-5(4H)-one (5p). This compound was synthesized as a white amorphous solid from 4p (268.1 mg, 0.53 mmol) in 51% yield by following general procedure 1.5: $^1$H NMR (400 MHz, CDCl$_3$, $\delta_H$) 7.61 (s, 1H), 7.37 (d, J=9.0 Hz, 2H), 6.98 (d, J=9.0 Hz, 2H), 6.86 (d, J=8.8 Hz, 2H), 6.71 (d, J=8.8 Hz, 2H), 3.86 (t, J=7.1 Hz, 2H), 3.42-3.30 (m, 4H), 3.28-3.19 (m, 6H), 1.90-1.72 (m, 2H), 1.65-1.56 (m, 2H), 1.49-1.34 (m, 4H). MALDI-MS: 463.2 (M+H$^+$), 485.2 (M+Na$^+$).

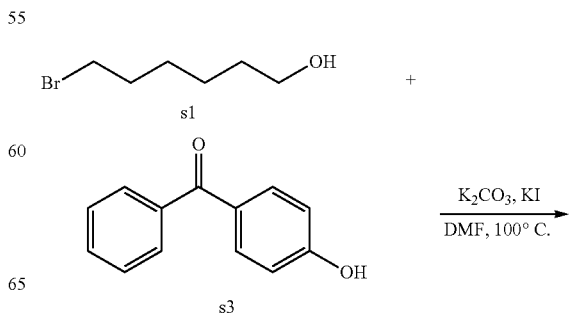

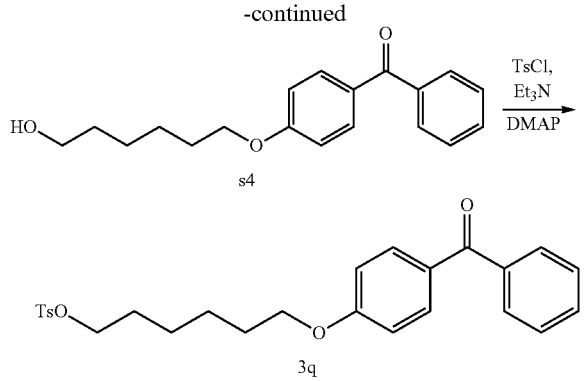

4-(6-Hydroxyhexyloxy)benzophenone (3q). A solution of 4-hydroxybenzophenone s3 (200 mg, 1.01 mmol) and 2.0 g of K$_2$CO$_3$ (101.0 mg, 0.731 mmol) in DMF (3 mL) was stirred at 100° C. for 30 min. A solution of 6-bromo-hexanol s1 (200.0 mg, 1.10 mmol) in 2 mL of DMF was then added dropwise. After addition, the reaction mixture was stirred at 100° C. for 4 h. Then it was cooled, poured into water, and extracted with CH$_2$Cl$_2$. The extract was dried over Na$_2$SO$_4$, concentrated to yield the crude product, which was purified by column chromatography (10:1→2:1 Hexanes-Ethyl Acetate) to afford s4 (298.7 mg, 91%) as a white amorphous solid: $^1$H NMR (400 MHz, CDCl$_3$, δ$_H$) 7.75-7.69 (m, 2H), 7.68-7.63 (m, 2H), 7.46 (t, J=8.3 Hz, 1H), 7.37 (t, J=7.5 Hz, 2H), 6.86 (d, J=5.8 Hz, 2H), 3.93 (t, J=6.5 Hz, 2H), 3.64-3.47 (m, 2H), 3.04 (s, 1H), 1.82-1.64 (m, 2H), 1.62-1.22 (m, 6H); $^{13}$C NMR (100 MHz, CDCl$_3$, δ$_H$) 195.84, 163.06, 161.45, 138.38, 132.75, 132.10, 129.86, 128.36, 114.21, 68.32, 62.60, 32.76, 29.24, 26.01, 25.75. ESI-MS: 299.2 (M+H$^+$), 321.2 (M+Na$^+$).

Compound 3q was synthesized as a colorless oil from s4 (335.6 mg, 1.12 mmol), TsCl (278.3, 1.46 mmol), Et$_3$N (225.7 mg, 2.24 mmol), and DMAP (136.8 mg, 1.12 mmol) in 83% yield by following general procedure 1.1: $^1$H NMR (400 MHz, CDCl$_3$, δ$_H$) 7.82-7.64 (m, 6H), 7.57-7.46 (m, 1H), 7.44-7.38 (m, 2H), 7.29 (d, J=8.5 Hz, 2H), 6.96-6.83 (m, 2H), 4.02-3.93 (m, 4H), 2.37 (s, 3H), 1.79-1.48 (m, 4H), 1.48-1.25 (m, 4H); $^{13}$C NMR (100 MHz, CDCl$_3$, δ$_H$) 195.58, 162.95, 161.28, 144.98, 138.47, 133.29, 132.72, 132.09, 130.08, 129.86, 128.40, 128.02, 114.22, 70.74, 68.15, 29.05, 28.92, 25.59, 25.34, 21.81. ESI-MS: 453.2 (M+H$^+$), 475.2 (M+Na$^+$).

1-(6-(4-Benzoylphenoxy)hexyl)-4-(4-(4-(4-(methoxymethoxy)phenyl)piperazin-1-yl)phenyl)-1H,2,4-triazol-5(4H)-one (14c). This compound was synthesized as a yellowish amorphous solid from 13 (57.2 mg, 0.150 mmol), 3q (82.6 mg, 0.183 mmol), and K$_2$CO$_3$ (41.5 mg, 0.300 mmol) in 36% yield by following general procedure 1.2: $^1$H NMR (400 MHz, CDCl$_3$, δ$_H$) 7.92-7.70 (m, 4H), 7.61 (s, 1H), 7.59-7.52 (m, 1H), 7.50-7.37 (m, 4H), 7.12-6.83 (m, 8H), 5.12 (s, 2H), 4.03 (t, J=6.4 Hz, 2H), 3.87 (t, J=7.1 Hz, 2H), 3.48 (s, 3H), 3.35 (dd, J=6.3, 3.7 Hz, 4H), 3.23 (dd, J=6.3, 3.7 Hz, 4H), 1.99-1.75 (m, 4H), 1.65-1.37 (m, 4H); $^{13}$C NMR (100 MHz, CDCl$_3$, δ$_H$) 195.76, 163.01, 152.37, 151.76, 150.84, 146.69, 138.56, 134.24, 132.78, 132.05, 130.13, 129.94, 128.39, 125.97, 123.75, 118.51, 117.51, 116.84, 114.24, 95.29, 68.26, 56.10, 50.70, 49.38, 45.66, 29.15, 28.77, 26.47, 25.82. ESI-MS: 662.3 (M+H$^+$), 684.3 (M+Na$^+$).

1-(6-(4-Benzoylphenoxy)hexyl)-4-(4-(4-(4-hydroxyphenyl)piperazin-1-yl)phenyl)-1H-1,2,4-triazol-5(4H)-one (5q). This compound was synthesized as a white amorphous solid from 4q (38.1 mg, 0.05 mmol) in 99% yield by following general procedure 1.5: $^1$H NMR (400 MHz, CDCl$_3$, δ$_H$) 7.89- 7.71 (m, 4H), 7.62 (s, 1H), 7.56 (ddd, J=6.7, 3.9, 1.3 Hz, 1H), 7.50-7.42 (m, 2H), 7.35 (d, J=8.9 Hz, 2H), 7.05-6.88 (m, 4H), 6.82 (t, J=6.1 Hz, 2H), 6.71 (d, J=8.9 Hz, 2H), 4.03 (d, J=7.1 Hz, 2H), 3.89 (t, J=7.1 Hz, 2H), 3.40-3.26 (m, 4H), 3.26-3.09 (m, 4H), 1.95-1.73 (m, 4H), 1.60-1.37 (m, 4H); $^{13}$C NMR (100 MHz, CDCl$_3$, δ$_H$) 195.98, 163.07, 152.67, 151.30, 151.06, 144.86, 138.50, 134.63, 132.84, 132.13, 130.07, 129.98, 128.42, 125.43, 124.41, 119.07, 116.70, 116.23, 114.28, 68.28, 51.30, 49.24, 45.83, 29.15, 28.77, 26.46, 25.79. ESI-MS: 618.3 (M+H$^+$), 640.3 (M+Na$^+$).

Pent-4-ynyl 4-methylbenzenesulfonate (3r). This compound was synthesized as a colorless oil from pent-4-yn-1-ol (145.0 mg, 132 mmol), TsCl (426.3 mg, 2.24 mmol), Et$_3$N (349.4 mg, 3.44 mmol), and DMAP (210.1 mg, 1.72 mmol) in 74% yield by following general procedure 1.1: $^1$H NMR (400 MHz, CDCl$_3$, δ$_H$) 7.77 (d, J=8.0 Hz, 2H), 7.33 (d, J=8.0 Hz, 2H), 4.24-3.97 (m, 2H), 2.42 (s, 3H), 2.23 (td, J=6.9, 2.6 Hz, 2H), 1.99-1.67 (m, 3H); $^{13}$C NMR (100 MHz, CDCl$_3$, δ$_H$) 145.06, 133.09, 130.09, 128.12, 82.33, 69.68, 68.98, 27.91, 21.85, 14.90. ESI-MS: 239.1 (M+H$^+$), 261.1 (M+Na$^+$).

(E)-Hex-3-enyl 4-methylbenzenesulfonate (3s). This compound was synthesized as a colorless oil from (E)-hex-3-en-1-ol (130.0 mg, 1.30 mmol), TsCl (322.2 mg, 1.69 mmol), Et$_3$N (196.6 mg, 1.95 mmol), and DMAP (158.8 mg, 1.30 mmol) in 99% yield by following general procedure 1.1: $^1$H NMR (400 MHz, CDCl$_3$, δ$_H$) 7.74 (d, J=8.0 Hz, 2H), 7.33 (d, J=8.0 Hz, 2H), 5.50 (dtt, J=15.3, 6.3, 1.3 Hz, 1H), 5.27-5.14 (m, 1H), 4.00 (t, J=6.9 Hz, 2H), 2.43 (s, 3H), 2.36-2.23 (m, 2H), 2.03-1.86 (m, 2H), 0.91 (t, J=7.5 Hz, 3H);

$^{13}$C NMR (100 MHz, CDCl$_3$, δ$_9$) 144.90, 136.27, 133.43, 130.01, 128.10, 122.71, 70.39, 32.28, 25.74, 21.84, 13.72. ESI-MS: 255.1 (M+H$^+$), 277.1 (M+Na$^+$).

(Z)-Hex-3-enyl 4-methylbenzenesulfonate (3t). This compound was synthesized as a colorless oil from (E)-hex-3-en-1-ol (70.0 mg, 0.70 mmol), TsCl (173.5 mg, 0.91 mmol), Et$_3$N (109.2 mg, 1.05 mmol), and DMAP (85.5 mg, 0.70 mmol) in 99% yield by following general procedure 1.1: $^1$H NMR (400 MHz, CDCl$_3$, δ$_H$) 7.78 (d, J=8.1 Hz, 2H), 7.33 (d, J=8.1 Hz, 2H), 5.58-5.35 (m, 1H), 5.28-5.08 (m, 1H), 3.99 (t, J=7.0 Hz, 2H), 2.44 (s, 3H), 2.42-2.31 (m, 2H), 2.07-1.90 (m, 2H), 0.91 (t, J=7.5 Hz, 3H); $^{13}$C NMR (100 MHz, CDCl$_3$, δ$_H$) 144.94, 135.73, 133.33, 130.03, 128.11, 122.27, 70.06, 27.18, 21.86, 20.82, 14.30. ESI-MS: 255.1 (M+H$^+$), 277.1 (M+Na$^+$).

(3-Ethyloxetan-3-yl)methyl 4-methylbenzenesulfonate (3v). This compound was synthesized as a colorless oil from (3-ethyloxetan-3-yl)methanol (122.4 mg, 1.05 mmol), TsCl (261.2 mg, 1.37 mmol), Et$_3$N (159.4 mg, 1.58 mmol), and DMAP (128.8 mg, 1.05 mmol) in 91% yield by following general procedure 1.1: $^1$H NMR (400 MHz, CDCl$_3$, δ$_H$) 7.80 (d, J=8.3 Hz, 2H), 7.36 (d, J=8.0 Hz, 2H), 4.35 (d, J=6.3 Hz, 2H), 4.29 (d, J=6.3 Hz, 2H), 4.15 (s, 2H), 2.45 (s, 3H), 1.73 (q, J=7.5 Hz, 2H), 0.79 (t, J=7.5 Hz, 3H); $^{13}$C NMR (100 MHz, CDCl$_3$, O$_H$) 145.35, 132.72, 130.21, 128.18, 71.97, 42.99, 26.26, 21.90, 8.05. ESI-MS: 271.1 (M+H$^+$), 293.1 (M+Na$^+$).

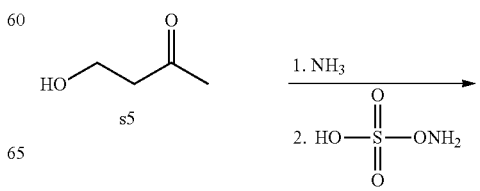

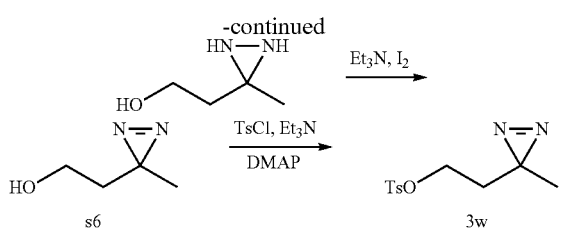

2-(3-Methyl-3H-diazirin-3-yl)ethyl 4-methylbenzenesulfonate (3w). 2-(3-Methyl-3H-diazirin-3-yl)ethanol s6 was synthesized as a crude product from 4-hydroxy-2-butanone s5 by following general procedure 1.6. Compound 3w was synthesized as a colorless oil from crude s6 (500.0 mg, 5.0 mmol), TsCl (1.0 g, 5.25 mmol), Et$_3$N (509.6 mg, 5.5 mmol), and DMAP (600.0 mg, 5.0 mmol) in 12% overall yield from s5 by following general procedure 1.1: $^1$H NMR (400 MHz, CDCl$_3$, $\delta_H$) 7.81 (d, J=7.5 Hz, 2H), 7.38 (d, J=7.5 Hz, 2H), 3.96 (t, J=6.2 Hz, 2H), 2.46 (s, 3H), 1.67 (t, J=6.2 Hz, 2H), 0.99 (s, 3H); $^{13}$C NMR. (100 MHz, CDCl$_3$, $\delta_H$) 145.30, 132.83, 130.15, 128.12, 65.46, 34.29, 23.62, 21.82, 19.89. ESI-MS: 255.1 (M+H$^+$), 277.1 (M+Na$^+$).

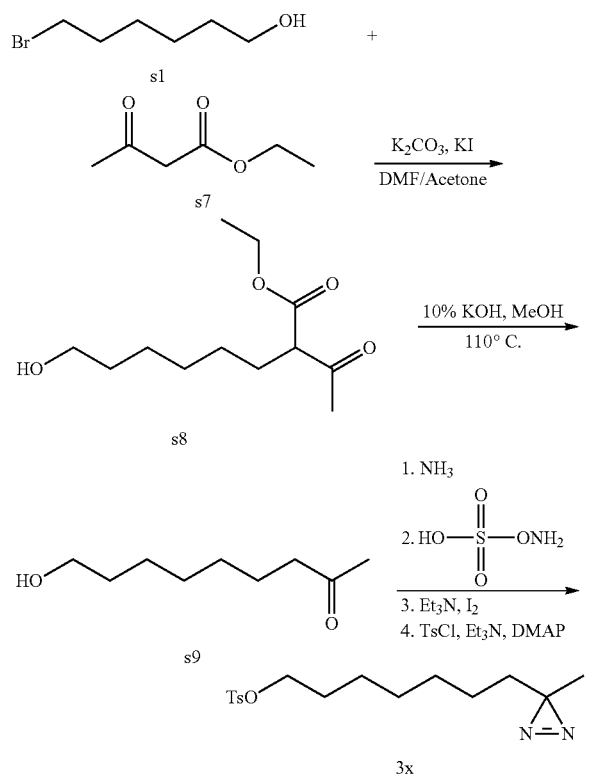

7-(3-Methyl-3H-diazirin-3-yl)heptyl 4-methylbenzenesulfonate (3x). 6-bromo-hexanol s1 (266.0 mg, 1.47 mmol), ethyl acetoacetate s7 (382.6 mg, 2.94 mmol), K$_2$CO$_3$ (609.5 g, 4.41 mmol), and KI (244.0 mg, 1.47 mmol) were mixed in acetone (25 mL) and DMF (1.5 mL), and the mixture was refluxed for 16 h. Most of the acetone was removed under reduced pressure and the residue was worked up with water and diethyl ether. The extract was dried over Na$_2$SO$_4$, concentrated to yield the crude product, which was purified by column chromatography (50:1→1:1 Hexanes-Ethyl Acetate) to afford s8 (331.8 mg, 98%) as a colorless syrup: $^1$H NMR (400 MHz, CDCl$_3$, $\delta_H$) 4.14 (q, J=7.1 Hz, 2H), 3.56 (t, J=6.6 Hz, 2H), 3.35 (t, J=7.4 Hz, 1H), 2.17 (s, 3H), 1.98 (br s, 1H), 1.88-1.70 (m, 2H), 1.57-1.42 (m, 2H), 1.38-1.16 (m, 9H); $^{13}$C NMR (100 MHz, CDCl$_3$, $\delta_H$) 203.64, 170.12, 62.89, 61.51, 60.03, 32.73, 29.27, 28.95, 28.24, 27.49, 25.61, 14.28. ESI-MS: 231.2 (M+H$^+$), 253.2 (M+Na$^+$).

Intermediate s7 (339.7 mg, 1.47 mmol) was mixed with 10% aq solution of KOH (2 mL, 3.57 mmol) and MeOH (2 mL), and the mixture was stirred and heated under reflux for 30 min, and left to stand overnight at room temperature. It was then diluted with water, and extracted with diethyl ether. The ether extract was dried Na$_2$SO$_4$, concentrated to yield the crude product, which was purified by column chromatography (20:1→1:1 Hexanes-Ethyl Acetate) to afford s9 (226.4 mg, 97%) as a colorless oil: $^1$H NMR (400 MHz, CDCl$_3$, $\delta_H$) 3.54 (t, J=6.7 Hz, 2H), 2.35 (t, J=7.4 Hz, 2H), 2.29 (br s, 1H), 2.06 (s, 3H), 1.57-1.42 (m, 4H), 1.35-1.15 (m, 6H); $^{13}$C NMR (100 MHz, CDCl$_3$, $\delta_H$) 209.84, 62.85, 43.89, 32.80, 30.02, 29.33, 29.25, 25.74, 23.89. ESI-MS: 159.1 (M+H$^+$), 181.1 (M+Na$^+$).

Compound 3x was synthesized as a colorless oil from crude s9 (1.0 g, 6.38 mmol) in 9% overall yield by following general procedures 1.6 and 1.1: $^1$H NMR (400 MHz, CDCl$_3$, $\delta_H$) 7.69 (d, J=8.3 Hz, 2H), 7.27 (d, J=8.3 Hz, 2H), 3.93 (t, J=6.4 Hz, 2H), 2.36 (s, 3H), 1.61-1.46 (m, 2H), 1.31-0.95 (m, 10H), 0.89 (s, 3H); $^{13}$C NMR (100 MHz, CDCl$_3$, $\delta_H$) 144.89, 133.28, 130.03, 127.98, 70.77, 34.30, 29.02, 28.85, 28.80, 25.32, 24.01, 21.76, 20.03. ESI-MS: 325.2 (M+H$^+$), 347.2 (M+Na$^+$).

Compounds 7a through 7x can be synthesized using the following general synthetic procedure.

General procedure A for the preparation of 7a-7q. To a solution of the phenol 5a-5q (1 equiv.) in DMSO was added NaH (a 60% dispersion in mineral oil, 4-5 equiv.). After the mixture was stirred at 50° C. under argon for 1 h, a solution of 6a (1.05-1.1 equiv.) in DMSO was added dropwise. After the addition, the temperature was increased to 90° C., and the solution was stirred under argon for another 3 h. The reaction was then quenched by the addition of a 50% aqueous NaCl solution, and the resulting mixture was extracted with CH$_2$Cl$_2$. The organic fractions were dried (Na$_2$SO$_4$), filtered, and concentrated under vacuum to yield the crude product, which was purified by column chromatography using a gradient (1:1 hexanes-EtOAc→neat EtOAc) to afford the desired products, which could be further purified by a second column (neat CH$_2$Cl$_2$→50:1 CH$_2$Cl$_2$-CH$_3$OH) if necessary.

General procedure B for the preparation of 7r-7x. To a slurry of 17a or 17b (1 equiv.) in acetonitrile was added 3r-3x (1.3-1.6 equiv.), K$_2$CO$_3$ (2 equiv.) and 18-Crown-6 (1 equiv.). After the mixture was stirred at 40-50° C. under argon for 6-14 h, the solvent was removed under vacuum to yield the crude product, which was purified by column chromatography (neat CH$_2$Cl$_2$→50:1 CH$_2$Cl$_2$-CH$_3$OH).

Example 1 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-methyl-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-methyl-3H-1,2,4-triazol-3-one (7a). This compound was synthesized as a colorless oil from 5a (20.1 mg, 0.057 mmol), 6a (29.1 mg, 0.060 mmol), and NaH (10.7 mg of a 60% dispersion in mineral oil, 0.27 mmol) in 41% yield by following typical procedure A: $^1$H NMR (400 MHz, CDCl$_3$, $\delta_H$) 8.20 (br s, 1H), 7.89 (br s, 1H), 7.63-7.55 (m, 2H), 7.49-7.36 (m, 3H), 7.25 (dd, J=8.7, 2.4 Hz, 1H), 7.05-6.90 (m, 4H), 6.82-6.76 (m, 2H), 4.79 (q, J=14.7 Hz, 2H), 4.40-4.32 (m, 1H), 3.94-3.88 (m, 1H), 3.85-3.75 (m, 2H), 3.52 (s, 3H), 3.46 (dd, J=9.7, 6.4 Hz, 1H), 3.38-3.33 (m, 4H), 3.25-3.19 (m, 4H); $^{13}$C NMR (100 MHz, CDCl$_3$, $\delta_C$) 152.82, 152.60, 151.61, 150.89, 146.20, 145.20, 136.28, 134.26, 133.34, 131.61, 129.84, 127.48, 125.92, 123.91, 118.69, 116.88, 115.47, 107.83, 74.91, 67.83, 67.65, 53.80, 50.80, 49.38, 32.90. MALDI-MS: 663.2 (M+H$^+$), 685.2 (M+Na$^+$). Purity: 98.5%, $t_R$=6.56 min.

Example 2 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-ethyl-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-ethyl-3H-1,2,4-triazol-3-one (7b). This compound was synthesized as a colorless oil from 5b (18.6 mg, 0.051 mmol), 6a (27.7 mg, 0.057 mmol), and NaH (10.0 mg of a 60% dispersion in mineral oil, 0.25 mmol) in 58% yield by following typical procedure A: $^1$H NMR (400 MHz, CDCl$_3$, $\delta_H$) 8.21 (s, 1H), 7.90 (s, 1H), 7.67-7.53 (m, 2H), 7.49-7.37 (m, 3H), 7.25 (dd, J=8.7, 2.3 Hz, 1H), 7.09-6.87 (m, 4H), 6.83-6.77 (m, 2H), 4.80 (q, J=14.7 Hz, 2H), 4.46-4.27 (m, 1H), 3.99-3.73 (m, 5H), 3.46 (dt, J=23.5, 11.8 Hz, 1H), 3.43-3.32 (m, 4H), 3.32-3.16 (m, 4H), 1.46-1.32 (t, J=7.3 Hz, 3H); $^{13}$C NMR (100 MHz, CDCl$_3$, $\delta_C$) 152.86, 152.11, 151.68, 150.84, 146.20, 136.29, 134.24, 133.35, 131.66, 129.84, 127.48, 126.02, 123.90, 118.71, 116.89, 115.49, 107.85, 74.92, 67.86, 67.67, 53.83, 50.82, 49.40, 40.79, 14.10. MALDI-MS: 677.2 (M+H$^+$), 699.2 (M+Na$^+$). Purity: >99%, $t_R$=7.04 min.

Example 3 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-propyl-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-propyl-3H-1,2,4-triazol-3-one (7c). This compound was synthesized as a colorless oil from 5c (22.9 mg, 0.060 mmol), 6a (32.0 mg, 0.066 mmol), and NaH (10.0 mg of a 60% dispersion in mineral oil, 0.25 mmol) in 53% yield by following typical procedure A: $^1$H NMR (400 MHz, CDCl$_3$, $\delta_H$) 8.24 (s, 1H), 7.90 (s, 1H), 7.65-7.54 (m, 2H), 7.47-7.38 (m, 3H), 7.25 (dd, J=8.4, 2.1 Hz, 1H), 7.13-6.95 (m, 4H), 6.85-6.76 (m, 2H), 4.80 (q, J=14.7 Hz, 2H), 4.45-4.28 (m, 1H), 3.97-3.73 (m, 5H), 3.60-3.10 (m, 9H), 1.94-1.68 (m, 2H), 0.97 (t, J=7.4 Hz, 3H); $^{13}$C NMR (100 MHz, CDCl$_3$, $\delta_C$) 152.38, 151.69, 150.59, 140.03, 136.29, 134.25, 134.12, 133.34, 131.66, 129.83, 127.49, 126.09, 123.80, 119.06, 117.02, 115.54, 107.85, 74.87, 67.81, 67.62, 53.81, 51.09, 49.23, 47.41, 22.26, 11.34. ESI-MS: 690.2 (M+H$^+$), 712.2 (M+Na$^+$). Purity: 97.4%, $t_R$=7.45 min.

Example 4 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-isopropyl-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-isopropyl-3H-1,2,4-triazol-3-one (7d). This compound was synthesized as a colorless oil from 5d (26.9 mg, 0.066 mmol), 6a (35.0 mg, 0.072 mmol), and NaH (10.9 mg of a 60% dispersion in mineral oil, 0.27 mmol) in 50% yield by following typical procedure A: $^1$H NMR (400 MHz, CDCl$_3$, $\delta_H$) 8.23 (s, 1H), 7.90 (s, 1H), 7.67-7.52 (m, 2H), 7.44-7.37 (m, 3H), 7.25 (dd, J=8.3, 2.2 Hz, 1H), 7.07-6.89 (m, 4H), 6.84-6.75 (m, 2H), 4.81 (q, J=14.6 Hz, 2H), 4.60-4.50 (m, 1H), 4.42-4.30 (m, 1H), 3.96-3.72 (m, 3H), 3.56-3.43 (m, 1H), 3.43-3.29 (m, 4H), 3.28-3.17 (m, 4H), 1.41 (d, J=6.7 Hz, 6H); $^{13}$C NMR (100 MHz, CDCl$_3$, $\delta_C$) 152.82, 152.09, 150.80, 146.23, 136.29, 134.27, 134.12, 133.37, 131.66, 129.84, 127.48, 126.06, 123.89, 118.69, 116.89, 115.49, 107.84, 74.92, 67.87, 67.68, 53.92, 50.82, 49.44, 47.17, 21.39. ESI-MS: 690.2 (M+H$^+$), 712.2 (M+Na$^+$). Purity: 94.7%, $t_R$=8.63 min.

Example 5 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-butyl-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-butyl-3H-1,2,4-triazol-3-one (7e). This compound was synthesized as a yellowish oil from 5e (38.8 mg, 0.099 mmol), 6a (52.6 mg, 0.11 mmol), and NaH (17.8 mg of a 60% dispersion in mineral oil, 0.45 mmol) in 52% yield by following typical procedure A: $^1$H NMR (400 MHz, CDCl$_3$, $\delta_H$) 8.21 (s, 1H), 7.89 (s, 1H), 7.64-7.52 (m, 2H), 7.46-7.38 (m, 3H), 7.24 (dd, J=8.6, 2.2 Hz, 1H), 7.08-6.89 (m, 4H), 6.83-6.77 (m, 2H), 4.79 (q, J=14.7 Hz, 2H), 4.42-4.28 (m, 1H), 3.98-3.71 (m, 5H), 3.48 (dd, J=9.6, 6.3 Hz, 1H), 3.55-3.41 (m, 4H), 3.40-3.27 (m, 4H), 1.87-1.70 (m, 2H), 1.40 (dq, J=14.7, 7.4 Hz, 2H), 0.96 (t, J=7.4 Hz, 3H); $^{13}$C NMR (100 MHz, CDCl$_3$, $\delta_C$) 152.83, 152.34, 151.55, 150.79, 146.22, 136.26, 134.28, 134.12, 133.34, 131.64, 129.83, 127.46, 126.07, 123.77, 118.67, 116.85, 115.51, 107.83, 74.93, 67.89, 67.66, 53.84, 50.79, 49.41, 45.55, 30.90, 20.00, 13.87. ESI-MS: 705.2 (M+H$^+$), 727.2 (M+Na$^+$). Purity: >99%, $t_R$=9.89 min.

Example 6 cis-(2S,4R)-4-[4-[4-[4-[[2-(2,4-Dichlorophenyl)-2-(1H,2,4-triazol-1-ylmethyl)-1,3-dioxolan-4-yl]methoxy]phenyl]-lpiperazinyl]phenyl]-2,4-dihydro-2-isobutyl-3H-1,2,4-triazol-3-one cis-(2S,4R)-4-[4-[4-[4-[[2-(2,4-Dichlorophenyl)-2-(1H,2,4-triazol-1-ylmethyl)-1,3-dioxolan-4-yl]methoxy]phenyl]-lpiperazinyl]phenyl]-2,4-dihydro-2-isobutyl-3H-1,2,4-triazol-3-one (7f). This compound was synthesized as a yellowish oil from 5f (20.0 mg, 0.051 mmol), 6a (27.1 mg, 0.058 mmol), and NaH (10.2 mg of a 60% dispersion in mineral oil, 0.26 mmol) in 63% yield by following typical procedure A: ¹H NMR (400 MHz, CDCl₃, δ$_H$) 8.22 (s, 1H), 7.89 (s, 1H), 7.66-7.51 (m, 2H), 7.48-7.37 (m, 3H), 7.25 (dd, J=8.6, 2.2 Hz, 1H), 7.05-6.88 (m, 4H), 6.83-6.76 (m, 2H), 4.80 (q, J=14.7 Hz, 2H), 4.41-4.29 (m, 1H), 3.91 (dd, J=8.3, 6.7 Hz, 1H), 3.86-3.72 (m, 2H), 3.65 (d, J=7.3 Hz, 2H), 3.47 (dd, J=9.6, 6.4 Hz, 1H), 3.38-3.32 (m, 4H), 3.25-3.19 (m, 4H), 2.19 (dt, J=13.7, 6.9 Hz, 1H), 0.97 (d, J=6.7 Hz, 6H); ¹³C NMR (100 MHz, CDCl₃) δ$_C$) 152.82, 152.64, 150.79, 146.22, 136.28, 134.28, 134.06, 133.34, 131.65, 129.84, 127.47, 126.11, 123.72, 118.68, 116.88, 115.48, 107.83, 74.92, 67.86, 67.66, 53.87, 53.04, 50.80, 49.43, 28.46, 20.12. ESI-MS: 705.2 (M+H⁺), 727.2 (M+Na⁺). Purity: >99%, t$_R$=9.63 min.

Example 7 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-pentyl-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-pentyl-3H-1,2,4-triazol-3-one (7g). This compound was synthesized as a yellowish oil from 5g (23.4 mg, 0.057 mmol), 6a (30.0 mg, 0.062 mmol), and NaH (11.4 mg of a 60% dispersion in mineral oil, 0.28 mmol) in 57% yield by following typical procedure A: ¹H NMR (400 MHz, CDCl₃, δ$_C$) 8.24 (s, 1H), 7.90 (s, 1H), 7.62-7.55 (m, 2H), 7.48-7.38 (m, 3H), 7.25 (dd, J=8.3, 2.1 Hz, 1H), 7.15-6.95 (m, 4H), 6.85-6.77 (m, 2H), 4.80 (q, J=14.7 Hz, 2H), 4.42-4.30 (m, 1H), 3.99-3.71 (m, 5H), 3.58-3.19 (m, 9H), 1.88-1.70 (m, 2H), 1.35 (dd, J=7.2, 3.7 Hz, 4H), 0.90 (dd, J=8.8, 5.0 Hz, 3H); ¹³C NMR (100 MHz, CDCl₃, δ$_C$) 152.32, 150.59, 136.31, 134.22, 134.12, 133.34, 131.67, 129.83, 127.50, 123.83, 117.07, 116.68, 115.57, 107.85, 74.86, 67.80, 67.60, 53.82, 51.42, 49.13, 45.85, 28.92, 28.58, 22.51, 14.21. ESI-MS: 719.3 (M+H⁺), 741.3 (M+Na⁺). Purity: >99%, t$_R$=13.19 min.

Example 8 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(1-methylbutyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(1-methylbutyl)-3H-1,2,4-triazol-3-one (7h). This compound was synthesized as a yellowish oil from 5h (23.4 mg, 0.057 mmol), 6a (29.8 mg, 0.062 mmol), and NaH (10.3 mg of a 60% dispersion in mineral oil, 0.26 mmol) in 66% yield by following typical procedure A: ¹H NMR (400 MHz, CDCl₃, δ$_H$) 8.26 (s, 1H), 7.91 (s, 1H), 7.72-7.53 (m, 2H), 7.48-7.37 (m, 3H), 7.25 (dd, J=8.3, 2.1 Hz, 1H), 7.13-6.96 (m, 4H), 6.86-6.79 (m, 2H), 4.81 (q, J=14.7 Hz, 2H), 4.51-4.29 (m, 2H), 3.98-3.86 (m, 1H), 3.86-3.71 (m, 2H), 3.58-3.10 (m, 8H), 1.93-1.77 (m, 1H), 1.62 (ddt, J=13.6, 9.9, 5.9 Hz, 1H), 1.47-1.18 (m, 6H), 0.92 (t, J=7.4 Hz, 3H); ¹³C NMR (100 MHz, CDCl₃, S$_C$) 152.10, 150.56, 136.29, 134.23, 134.11, 133.34, 131.66, 129.83, 127.49, 123.75, 119.06, 117.05, 115.55, 107.84, 74.86, 67.80, 67.61, 53.86, 51.07, 49.24, 37.69, 29.93, 19.88, 19.70, 14.00. ESI-MS: 719.3 (M+H⁺), 741.3 (M+Na⁺). Purity: >99%, t$_R$=9.85 min.

Example 9 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(3-methylbutyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(3-methylbutyl)-3H-1,2,4-triazol-3-one (7i). This compound was synthesized as a yellowish oil from 5i (23.4 mg, 0.057 mmol), 6a (30.3 mg, 0.063 mmol), and NaH (11.1 mg of a 60% dispersion in mineral oil, 0.28 mmol) in 63% yield by following typical procedure A: ¹H NMR (400 MHz, CDCl₃, δ$_H$) 8.23 (s, 1H), 7.90 (s, 1H), 7.67-7.51 (m, 2H), 7.51-7.34 (m, 3H), 7.25 (dd, J=8.4, 2.0 Hz, 1H), 7.15-6.97 (m, 4H), 6.88-6.80 (m, 2H), 4.80 (q, J=14.7 Hz, 2H), 4.43-4.27 (m, 1H), 3.98-3.70 (m, 5H), 3.56-3.08 (m, 9H), 1.73-1.60 (m, 3H), 0.96 (d, J=6.3 Hz, 6H); ¹³C NMR (100 MHz, CDCl₃, δ$_C$) 152.23, 150.60, 136.29, 134.24, 134.08, 133.34, 131.66, 129.83, 127.48, 123.76, 119.07, 117.03, 115.55, 107.84, 74.86, 67.81, 67.61, 53.83, 51.18, 49.21, 44.19, 37.56, 25.81, 22.61. ESI-MS: 719.3 (M+H⁺), 741.3 (M+Na⁺). Purity: >99%, t$_R$=10.10 min.

Example 10 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(1-ethylpropyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(1-ethylpropyl)-3H-1,2,4-triazol-3-one (7j). This compound was synthesized as a yellowish oil from 5j (23.3 mg, 0.057 mmol), 6a (30.1 mg, 0.062 mmol), and NaH (10.4 mg of a 60% dispersion in mineral oil, 0.28 mmol) in 63% yield by following typical procedure A: ¹H NMR (400 MHz, CDCl₃, δ$_H$) 8.26 (s, 1H), 7.91 (s, 1H), 7.69-7.53 (m, 2H), 7.51-7.37 (m, 3H), 7.25 (dd, J=8.4, 2.1 Hz, 1H), 7.10-6.93 (m, 4H), 6.85-6.77 (m, 2H), 4.81 (q, J=14.7 Hz, 2H), 4.47-4.29 (m, 1H), 4.12-3.99 (m, 1H), 3.99-3.86 (m, 1H), 3.87-3.71 (m, 2H), 3.57-3.13 (m, 9H), 1.94-1.62 (m, 4H), 0.88 (t, J=7.4 Hz, 6H); ¹³C NMR (100 MHz, CDCl₃, δ$_C$) 153.05, 150.53, 136.31, 134.22, 133.34, 131.67, 129.84, 127.50, 123.74, 119.15, 117.06, 115.57, 107.84, 74.87, 67.81, 67.61, 59.06, 53.86, 51.34, 49.22, 27.00, 10.97. ESI-MS: 719.3 (M+H⁺), 741.3 (M+Na⁺). Purity: 95.1%, t$_R$=9.17 min.

Example 11 cis-(2S,4R)-4-[4-[4-[4-[[2-(2,4-Dichlorophenyl)-2-(1H-1,2,4-triazol-1-ylmethyl)-1.3-dioxolan-4-yl]methoxy]phenyl]-lpiperazinyl]phenyl]-2,4-dihydro-2-(1-cyclohexyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(1-cyclohexyl)-3H-1,2,4-triazol-3-one (7k). This compound was synthesized as a yellowish oil from 5k (21.8 mg, 0.052 mmol), 6a (25.4 mg, 0.055 mmol), and NaH (10.0 mg of a 60% dispersion in mineral oil, 0.25 mmol) in 69% yield by following typical procedure A: ¹H NMR (400 MHz, CDCl₃, δ$_H$) 8.20 (s, 1H), 7.88 (s, 1H), 7.71-7.51 (m, 2H), 7.47-7.36 (m, 3H), 7.24 (dd, J=8.7, 2.2 Hz, 1H), 7.05-6.87 (m, 4H), 6.82-6.74 (m, 2H), 4.79 (q, J=14.7 Hz, 2H), 4.40-4.28 (m, 1H), 4.20-4.05 (m, 1H), 3.98-3.71 (m, 3H), 3.46 (dd, J=9.6, 6.3 Hz, 1H), 4.43-4.25 (m, 4H), 3.27-3.12 (m, 4H), 1.95-1.63 (m, 6H), 1.49-1.32 (m, 2H), 1.30-1.13 (m, 2H); $^{13}$C NMR (100 MHz, CDCl$_3$, δ$_C$) 152.80, 151.73, 151.60, 150.75, 146.19, 136.26, 134.26, 134.04, 133.33, 131.64, 129.83, 127.48, 126.06, 123.89, 118.68, 116.87, 115.45, 107.82, 74.91, 67.82, 67.65, 54.31, 53.79, 50.80, 49.41, 31.69, 25.65, 25.45. ESI-MS: 731.3 (M+H$^+$), 753.3 (M+Na$^+$). Purity: >99%, t$_R$=7.77 min.

Example 12 cis-(2S,4R)-4-[4-[4-[4-[[2-(2/l-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(1-cyclopentylmethyl)-3H-1,2,4-triazol-3-one cis-(2S,4R)-4-[4-[4-[4-[[2-(2/l-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(1-cyclopentylmethyl)-3H-1,2,4-triazol-3-one (7l). This compound was synthesized as a yellowish oil from 5l (20.0 mg, 0.048 mmol), 6a (25.4 mg, 0.052 mmol), and NaH (10.2 mg of a 60% dispersion in mineral oil, 0.26 mmol) in 68% yield by following typical procedure A: $^1$H NMR (400 MHz, CDCl$_3$, 6$_H$) 8.21 (s, 1H), 7.89 (s, 1H), 7.66-7.53 (m, 2H), 7.51-7.37 (m, 3H), 7.25 (dd, J=8.1, 1.7 Hz, 1H), 7.14-6.89 (m, 4H), 6.82-6.72 (m, 2H), 4.80 (q, J=14.7 Hz, 2H), 4.40-4.32 (m, 1H), 4.01-3.71 (m, 5H), 3.54-3.15 (m, 9H), 2.43 (dt, J=15.3, 7.6 Hz, 1H), 1.95-1.47 (m, 6H), 1.40-1.25 (m, 2H); $^{13}$C NMR (100 MHz, CDCl$_3$, δ$_C$) 152.83, 152.52, 151.61, 150.78, 146.21, 136.28, 134.27, 134.00, 133.34, 131.65, 129.84, 127.48, 126.12, 123.74, 118.70, 116.89, 115.48, 107.84, 74.92, 67.86, 67.66, 53.83, 50.81, 50.53, 49.44, 39.53, 30.36, 25.30. ESI-MS: 731.3 (M+H$^+$), 753.3 (M+Na$^+$). Purity: >99%, t$_R$=7.74 min.

Example 13 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(n-octyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(n-octyl)-3H-1,2,4-triazol-3-one (7m). This compound was synthesized as a yellowish oil from 5m (27.4 mg, 0.055 mmol), 6a (29.3 mg, 0.060 mmol), and NaH (10.9 mg of a 60% dispersion in mineral oil, 0.27 mmol) in 72% yield by following typical procedure A: $^1$H NMR (400 MHz, CDCl$_3$, δ$_H$) 8.21 (s, 1H), 7.90 (s, 1H), 7.70-7.51 (m, 2H), 7.50-7.36 (m, 3H), 7.25 (dd, J=8.4, 1.9 Hz, 1H), 7.13-6.90 (m, 4H), 6.84-6.73 (m, 2H), 4.80 (q, J=14.7 Hz, 2H), 4.42-4.29 (m, 1H), 3.99-3.71 (m, 5H), 3.57-3.12 (m, 9H), 1.85-1.72 (dt, J=14.6, 7.4 Hz, 2H), 1.48-1.16 (m, 10H), 0.87 (t, J=6.8 Hz, 3H); $^{13}$C NMR (100 MHz, CDCl$_3$, δ$_C$) 152.83, 152.33, 151.62, 150.81, 146.22, 136.29, 134.27, 134.11, 133.35, 131.66, 129.83, 127.47, 126.08, 123.80, 118.70, 116.89, 115.49, 107.85, 74.92, 67.86, 67.67, 53.84, 50.82, 49.43, 45.88, 32.00, 29.38, 28.88, 26.80, 22.86, 14.33. ESI-MS: 761.3 (M+H$^+$), 783.3 (M+Na$^+$). Purity: >99%, t$_R$=14.67 min.

Example 14 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(6-phenylhexyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(6-phenylhexyl)-3H-1,2,4-triazol-3-one (7n). This compound was synthesized as a yellowish oil from 5n (25.3 mg, 0.051 mmol), 6a (25.9 mg, 0.054 mmol), and NaH (10.9 mg of a 60% dispersion in mineral oil, 0.27 mmol) in 70% yield by following typical procedure A: $^1$H NMR (400 MHz, CDCl$_3$, δ$_H$) 8.21 (s, 1H), 7.90 (s, 1H), 7.69-7.53 (m, 2H), 7.52-7.35 (m, 3H), 7.33-7.22 (m, 3H), 7.22-7.12 (m, 3H), 7.08-6.99 (m, 2H), 6.97-6.89 (m, 2H), 6.83-6.76 (m, 2H), 4.80 (q, J=14.7 Hz, 2H), 4.39-4.32 (m, 1H), 4.01-3.72 (m, 5H), 3.47 (dd, J=9.7, 6.4 Hz, 1H), 3.41-3.32 (m, 4H), 3.28-3.18 (m, 4H), 2.67-2.52 (d, J=7.5 Hz, 2H), 1.83-1.72 (m, 2H), 1.70-1.56 (m, 2H), 1.46-1.33 (m, 4H); $^{13}$C NMR (100 MH$_z$, CDCl$_3$, δ$_C$) 152.82, 152.33, 151.62, 150.81, 146.20, 142.88, 136.28, 134.27, 134.17, 133.34, 131.66, 129.84, 128.62, 128.46, 127.49, 126.04, 125.83, 123.81, 118.70, 116.89, 115.47, 107.84, 74.92, 67.83, 67.66, 53.81, 50.81, 49.42, 45.81, 36.07, 31.53, 29.07, 28.83, 26.66. ESI-MS: 808.3 (M+H$^+$), 830.3 (M+Na$^+$). Purity: >99%, t$_R$=12.78 min.

Example 15 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(hex-3-ynyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(hex-3-ynyl)-3H-1,2,4-triazol-3-one (7o). This compound was synthesized as a yellowish oil from 5o (25.9 mg, 0.062 mmol), 6a (31.6 mg, 0.065 mmol), and NaH (12.8 mg of a 60% dispersion in mineral oil, 0.32 mmol) in 65% yield by following typical procedure A: $^1$H NMR (400 MHz, CDCl$_3$, δ$_H$) 8.19 (s, 1H), 7.88 (s, 1H), 7.69-7.51 (m, 2H), 7.51-7.33 (m, 3H), 7.24 (dd, J=8.2, 2.0 Hz, 1H), 7.06-6.87 (m, 4H), 6.79 (d, J=9.0 Hz, 2H), 4.78 (q, J=14.7 Hz, 2H), 4.48-4.25 (m, 1H), 4.06-3.72 (m, 5H), 3.54-3.12 (m, 9H), 2.63 (tt, J=7.3, 2.3 Hz, 2H), 2.13 (qt, J=7.5, 2.3 Hz, 2H), 1.17-0.99 (t, J=7.2 Hz, 3H); $^{13}$C NMR (100 MHz, CDCl$_3$, δ$_C$) 152.81, 152.25, 151.60, 150.84, 146.19, 145.15, 136.26, 134.51, 134.27, 133.33, 131.65, 129.84, 127.48, 125.92, 123.83, 118.68, 116.87, 115.46, 107.83, 83.95, 75.41, 74.91, 67.83, 67.65, 53.80, 50.79, 49.38, 45.02, 19.26, 14.34, 12.62. ESI-MS: 729.2 (M+H$^+$), 751.2 (M+Na$^+$). Purity: >99%, t$_R$=7.93 min.

Example 16 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(6-azidohexyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(6-azidohexyl)-3H-1,2,4-triazol-3-one (7p). This compound was synthesized as a yellowish oil from 5p (33.1 mg, 0.072 mmol), 6a (36.4 mg, 0.075 mmol), and NaH (14.4 mg of a 60% dispersion in mineral oil, 0.36 mmol) in 44% yield by following typical procedure A: $^1$H NMR (400 MHz, CDCl$_3$, δ$_H$) 8.19 (s, 1H), 7.87 (s, 1H), 7.60 (s, 1H), 7.55 (d, J=8.4 Hz, 1H), 7.44 (d, J=2.1 Hz, 1H), 7.39 (t, J=6.0 Hz, 2H), 7.23 (dd, J=8.4, 2.1 Hz, 1H), 7.00 (d, J=9.0 Hz, 2H), 6.93 (d, J=8.8 Hz, 2H), 6.78 (d, J=9.0 Hz, 2H), 4.77 (q, J=14.7 Hz, 2H), 4.41-4.25 (m, 1H), 3.94-3.70 (m, 5H), 3.44 (dd, J=9.7, 5.9 Hz, 1H), 3.41-3.30 (m, 4H), 3.28-3.16 (m, 6H), 1.88-1.71 (m, 2H), 1.65-1.52 (m, 2H), 1.45-1.33 (m, 4H); $^{13}$C NMR (100 MHz, CDCl$_3$, δ$_C$) 152.93, 152.32, 151.59, 150.76, 136.24, 134.25, 133.32, 131.63, 129.84, 127.47, 126.00, 123.77, 118.75, 116.87, 115.47, 107.82, 74.90, 67.81, 67.62, 53.78, 51.53, 50.87, 49.33, 45.60, 28.91, 28.72, 26.50, 26.31. ESI-MS: 774.2 (M+H$^+$), 796.2 (M+Na$^+$). Purity: >99%, t$_R$=7.26 min.

Example 17 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(6-(4-benzoylphenoxy)hexyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(6-(4-benzoylphenoxy)hexyl)-3H-1,2,4-triazol-3-one (7q). This compound was synthesized as a yellowish oil from 5q (38.8 mg, 0.063 mmol), 6a (34.1 mg, 0.070 mmol), and NaH (12.3 mg of a 60% dispersion in mineral oil, 0.31 mmol) in 74% yield by following typical procedure A: $^1$H NMR (400 MHz, CDCl$_3$, δ$_H$) 8.22 (s, 1H), 7.89 (s, 1H), 7.84-7.77 (m, 2H), 7.73 (dd, J=8.3, 1.2 Hz, 2H), 7.61 (s, 1H), 7.58-7.52 (m, 2H), 7.48-7.42 (m, 3H), 7.39 (d, J=8.9 Hz, 2H), 7.24 (dd, J=8.4, 2.0 Hz, 1H), 7.01 (d, J=9.0 Hz, 2H), 6.93 (d, J=8.8 Hz, 4H), 6.79 (d, 7-8.8 Hz, 2H), 4.79 (q, J=14.7 Hz, 2H), 4.46-4.25 (m, 1H), 4.02 (t, J=6.4 Hz, 2H), 3.96-3.71 (m, 5H), 3.47 (dd, J=9.5, 6.4 Hz, 1H), 3.42-3.28 (m, 4H), 3.28-3.12 (m, 4H), 1.83 (dq, J=12.9, 6.6 Hz, 4H), 1.64-1.36 (m, 4H); $^{13}$C NMR (100 MHz, CDCl$_3$, 195.78, 163.01, 152.82, 152.36, 151.68, 150.82, 146.21, 138.54, 136.26, 134.24, 133.33, 132.77, 132.05, 131.64, 130.11, 129.93, 129.84, 128.39, 127.47, 125.96, 123.77, 118.67, 116.84, 115.49, 114.23, 107.82, 74.92, 68.26, 67.86, 67.64, 53.86, 50.78, 49.37, 45.66, 29.14, 28.76, 26.46, 25.81. ESI-MS: 929.3 (M+H$^+$), 951.3 (M+Na$^+$). Purity: >99%, t$_R$=15.68 min.

Example 18 cis-(2R,4S)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(pent-4-ynyl)-3H-1,2,4-triazol-3-one cis-(2R,4S)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(pent-4-ynyl)-3H-1,2,4-triazol-3-one (7r). This compound was synthesized as a yellowish oil from 17b (25.6 mg, 0.039 mmol), 3r (14.1 mg, 0.059 mmol), K$_2$CO$_3$ (10.9 mg, 0.079 mmol), and 18-Crown-6 (10.4 mg, 0.039 mmol) in 40% yield by following typical procedure B: $^1$H NMR (400 MHz, CDCl$_3$, δ$_H$) 8.22 (s, 1H), 7.90 (s, 1H), 7.62 (s, 1H), 7.58 (d, J=8.4 Hz, 1H), 7.48 (d, J=2.1 Hz, 1H), 7.42 (dd, J=7.1, 5.1 Hz, 2H), 7.25 (dd, J=8.7, 2.3 Hz, 1H), 7.03 (d, J=9.1 Hz, 2H), 6.94 (d, J=9.0 Hz, 2H), 6.80 (d, J=9.0 Hz, 2H), 4.81 (q, J=14.7 Hz, 2H), 4.41-4.33 (m, 1H), 4.04-3.88 (m, 3H), 3.87-3.74 (m, 2H), 3.49 (dd, J=9.7, 6.4 Hz, 1H), 3.42-3.34 (m, 4H), 3.27-3.19 (m, 4H), 2.32 (td, J=7.0, 2.6 Hz, 2H), 2.11-1.96 (m, 3H); $^{13}$C NMR (100 MHz, CDCl$_3$, δ$_C$) 152.84, 152.38, 151.68, 150.86, 146.24, 136.29, 134.35, 133.35, 131.66, 129.83, 127.47, 125.95, 123.79, 118.69, 116.86, 115.51, 107.85, 83.19, 74.93, 69.28, 67.89, 67.67, 53.87, 50.80, 49.40, 44.74, 27.71, 16.16. ESI-MS: 715.2 (M+H$^+$), 737.2 (M+Na$^+$). Purity: >99%, t$_R$=7.35 min.

Example 19 cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-((E)-hex-3-enyl)-3H-1,2,4-triazol-3-one cis-(2S,4R)-4-[4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-((E)-hex-3-enyl)-3H-1,2,4-triazol-3-one (7s). This compound was synthesized as a yellowish oil from 17a (19.8 mg, 0.031 mmol), 3s (12.3 mg, 0.048 mmol), K$_2$CO$_3$ (8.4 mg, 0.061 mmol), and 18-Crown-6 (8.1 mg, 0.031 mmol) in 55% yield by following typical procedure B: $^1$H NMR (400 MHz, CDCl$_3$, δ$_H$) 8.23 (s, 1H), 7.90 (s, 1H), 7.61-7.55 (m, 2H), 7.51-7.37 (m, 3H), 7.25 (dd, J=8.4, 1.8 Hz, 1H), 7.03 (d, J=9.0 Hz, 2H), 6.95 (d, J=8.9 Hz, 2H), 6.81 (d, J=8.9 Hz, 2H), 5.50 (dtt, J=15.3, 6.3, 1.3 Hz, 1H), 5.31-5.15 (m, 1H), 4.84 (q, J=14.7 Hz, 2H), 4.49-4.32 (m, 1H), 3.92-3.73 (m, 6H), 3.52 (dd, J=9.7, 6.5 Hz, 1H), 3.41-3.33 (m, 4H), 3.26-3.17 (m, 4H), 2.43 (q, J=7.0 Hz, 2H), 2.08-1.92 (m, 2H), 0.92 (t, J=7.5 Hz, 3H); $^{13}$C NMR (100 MHz, CDCl$_3$, δ$_C$) 152.83, 152.36, 151.66, 150.85, 146.21.136.28, 134.77, 134.29, 133.34, 131.67, 129.84, 127.49, 126.00, 124.52, 123.81, 118.70, 116.88, 115.48, 107.85, 74.92, 67.83, 67.66, 53.82, 50.82, 49.42, 45.57, 25.90, 21.82, 14.03. ESI-MS: 731.2 (M+H$^+$), 753.2 (M+Na$^+$). Purity: 95.3%, t$_R$=9.15 min.

Example 20 cis-(2S,4R)-4-[4-[4-[4-[[2-(2,4-Dichlorophenyl)-2-(1H-1,2,4-triazol-1-ylmethyl)-13-dioxolan-4-yl]methoxy]phenyl]-lpiperazinyl]phenyl]-2,4-dihydro-2-((Z)-hex-3-enyl)-3H-1,2,4-triazol-3-one cis-(2S,4R)-4-[4-[4-[4-[[2-(2,4-Dichlorophenyl)-2-(1H-1,2,4-triazol-1-ylmethyl)-13-dioxolan-4-yl]methoxy]phenyl]-lpiperazinyl]phenyl]-2,4-dihydro-2-((Z)-hex-3-enyl)-3H-1,2,4-triazol-3-one (7t). This compound was synthesized as a yellowish oil from 17a (18.7 mg, 0.029 mmol), 3t (11.0 mg, 0.043 mmol), K$_2$CO$_3$ (8.0 mg, 0.058 mmol), and 18-Crown-6 (7.6 mg, 0.029 mmol) in 70% yield by following typical procedure B: $^1$H NMR (400 MHz, CDCl$_3$, δ$_H$) 8.21 (s, 1H), 7.89 (s, 1H), 7.62-7.55 (m, 2H), 7.50-7.36 (m, 3H), 7.25 (dd, J=8.5, 1.7 Hz, 1H), 7.02 (d, J=9.0 Hz, 2H), 6.94 (d, J=8.9 Hz, 2H), 6.80 (d, J=8.9 Hz, 2H), 5.50 (dt, J=10.7, 7.2 Hz, 1H), 5.44-5.31 (m, 1H), 4.85 (q, J=14.7 Hz, 2H), 4.48-4.30 (m, 1H), 3.95-3.75 (m, 6H), 3.49 (dd, J=9.9, 6.3 Hz, 1H), 3.42-3.34 (m, 4H), 3.27-3.19 (m, 4H), 2.54 (q, J=7.0 Hz, 2H), 2.12-1.97 (m, 2H), 0.93 (t, J=7.5 Hz, 3H); $^{13}$C NMR (100 MHz, CDCl$_3$, δ$_C$) 152.83, 152.34, 151.64, 150.84, 146.19.136.29, 134.93, 134.21, 133.34, 131.66, 129.84, 127.49, 126.01, 124.33, 123.83, 118.71, 116.89, 115.47, 107.84, 74.92, 67.83, 67.66, 53.82, 50.82, 49.42, 45.60, 26.89, 20.80, 14.47. ESI-MS: 731.2 (M+H$^+$), 753.2 (M+Na$^+$). Purity: 95.0%, $t_R$=8.91 min.

Example 21 cis-(2S,4R)-4-[4-[4-[[2-(2,4-Dichlorophenyl)-2-(1H-1,2,4-triazol-1-ylmethyl)-1,3-dioxolan-4-yl]methoxy]phenyl]-]piperazinyl]phenyl]-2,4-dihydro-2-(5-cyanopentyl)-3H-1,2,4-triazol-3-one cis-(2S,4R)-4-[4-[4-[[2-(2,4-Dichlorophenyl)-2-(1H-1,2,4-triazol-1-ylmethyl)-1,3-dioxolan-4-yl]methoxy]phenyl]-]piperazinyl]phenyl]-2,4-dihydro-2-(5-cyanopentyl)-3H-1,2,4-triazol-3-one (7u). This compound was synthesized as a yellowish oil from 17a (40.0 mg, 0.062 mmol), 3u (16.3 mg, 0.092 mmol), K$_2$CO$_3$ (17.1 mg, 0.124 mmol), and 18-Crown-6 (16.3 mg, 0.062 mmol) in 41% yield by following typical procedure B: $^1$H NMR (400 MHz, CDCl$_3$, $\delta_H$) 8.25 (s, 1H), 7.90 (s, 1H), 7.65-7.55 (m, 2H), 7.48 (d, J=1.7 Hz, 1H), 7.41 (d, J=8.8 Hz, 2H), 7.25 (dd, J=8.4, 2.0 Hz, 1H), 7.03 (d, J=8.9 Hz, 2H), 6.94 (d, J=8.7 Hz, 2H), 6.81 (d, J=8.7 Hz, 2H), 4.81 (q, J=14.7 Hz, 2H), 4.50-4.25 (m, 1H), 4.05-3.71 (m, 5H), 3.49 (t, J=7.8 Hz, 1H), 3.43-3.33 (m, 4H), 3.29-3.20 (m, 4H), 2.37 (t, J=7.1 Hz, 2H), 1.93-1.81 (m, 2H), 1.80-1.69 (m, 2H), 1.60-1.49 (m, 2H); $^{13}$C NMR (100 MHz, CDCl$_3$, $\delta_C$) 152.85, 152.44, 150.91, 146.24, 136.30, 134.42, 134.28, 133.35, 131.66, 129.84, 127.48, 125.87, 123.87, 118.70, 116.87, 115.51, 107.83, 74.93, 67.89, 67.67, 53.95, 50.80, 49.39, 45.19, 28.01, 25.80, 25.15, 17.31. ESI-MS: 744.2 (M+H$^+$), 766.2 (M+Na$^+$). Purity: 94.9%, $t_R$=5.36 min.

Example 22 cis-(2S,4R)-4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-((3-ethyloxetan-3-yl)methyl)-3H-1,2,4-triazol-3-one cis-(2S,4R)-4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-((3-ethyloxetan-3-yl)methyl)-3H-1,2,4-triazol-3-one (7v). This compound was synthesized as a yellowish oil from 17a (30.0 mg, 0.046 mmol), 3v (18.7 mg, 0.069 mmol), K$_2$CO$_3$ (12.8 mg, 0.092 mmol), and 18-Crown-6 (12.2 mg, 0.046 mmol) in 40% yield by following typical procedure B: $^1$H NMR (400 MHz, CDCl$_3$, $\delta_H$) 8.21 (s, 1H), 7.90 (s, 1H), 7.72-7.52 (m, 2H), 7.52-7.36 (m, 3H), 7.25 (dd, J=8.5, 2.2 Hz, 1H), 7.13-6.72 (m, 6H), 4.91-4.69 (m, 4H), 4.45 (d, J=6.3 Hz, 2H), 4.41-4.32 (m, 1H), 4.07 (s, 2H), 3.92 (dd, J=8.3, 6.7 Hz, 1H), 3.87-3.73 (m, 2H), 3.54-3.44 (m, 1H), 3.43-3.32 (m 4H), 3.30-3.23 (m, 4H), 1.74 (dd, J=14.9, 7.4 Hz, 2H), 1.00 (t, J=7.4 Hz, 3H); $^{13}$C NMR (100 MHz, CDCl$_3$, $\delta_C$) 152.84, 151.60, 150.92, 146.20, 145.18, 136.28, 134.63, 134.27, 133.34, 131.65, 129.84, 127.48, 125.80, 123.79, 118.70, 116.87, 115.49, 107.84, 78.88, 74.92, 67.86, 67.66, 53.82, 50.80, 49.38, 49.26, 44.25, 27.57, 8.34. ESI-MS: 747.3 (M+H$^+$), 769.3 (M+Na$^+$). Purity: 94.6%, $t_R$=5.85 min.

Example 23 cis-(2S,4R)-4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(2-(3-methyl-3H-diazirin-3-yl)ethyl)-3H-1,2,4-triazol-3-one cis-(2S,4R)-4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(2-(3-methyl-3H-diazirin-3-yl)ethyl)-3H-1,2,4-triazol-3-one (7w). This compound was synthesized as a yellowish oil from 17a (20.2 mg, 0.031 mmol), 3w (10.3 mg, 0.040 mmol), K$_2$CO$_3$ (8.6 mg, 0.062 mmol), and 18-Crown-6 (8.2 mg, 0.031 mmol) in 55% yield by following typical procedure B: $^1$H NMR (400 MHz, CDCl$_3$, $\delta_H$) 8.24 (s, 1H), 7.90 (s, 1H), 7.64 (s, 1H), 7.58 (d, J=8.4 Hz, 1H), 7.48 (d, J=2.1 Hz, 1H), 7.45-7.39 (m, 2H), 7.26 (dd, J=8.6, 2.1 Hz, 1H), 7.04 (d, J=9.0 Hz, 2H), 6.94 (d, J=8.6 Hz, 2H), 6.81 (d, J=8.7 Hz, 2H), 4.81 (q, J=14.7 Hz, 2H), 4.43-4.31 (m, 1H), 3.98-3.85 (m, 3H), 3.85-3.75 (m, 2H), 3.49 (dd, J=9.4, 6.4 Hz, 1H), 3.40-3.34 (m, 4H), 3.28-3.20 (m, 4H), 1.81 (t, J=7.1 Hz, 2H), 1.10 (s, 3H); $^{13}$C NMR (100 MHz, CDCl$_3$, $\delta_C$) 152.84, 152.36, 150.95, 146.23, 136.29, 134.68, 134.28, 133.35, 131.66, 129.84, 127.47, 125.85, 123.95, 118.70, 116.87, 115.51, 107.84, 74.93, 67.88, 67.67, 53.90, 50.80, 49.39, 41.08, 33.91, 24.16, 19.57. ESI-MS: 731.2 (M+H$^+$), 753.2 (M+Na$^+$). Purity: 93.7%, $t_R$=9.84 min.

Example 24 cis-(2S,4R)-4-[4-[4-[[2-(2,4-Dichlorophenyl)-2-(1H-1,2,4-triazol-1-ylmethyl)-1,3-dioxolan-4-yl]methoxy]phenylI]-lpiperazinyl] phenyl]-2,4-dihydro-2-(7-(3-methyl-3H-diazirin-3-yl)heptyl)-3H-1,2,4-triazol-3-one cis-(2S,4R)-4-[4-[4-[[2-(2,4-Dichlorophenyl)-2-(1H-1,2,4-triazol-1-ylmethyl)-1,3-dioxolan-4-yl]methoxy]phenyl]-lpiperazinyl]phenyl]-2,4-dihydro-2-(7-(3-methyl-3H-diazirin-3-yl)heptyl)-3H-1,2,4-triazol-3-one (7x). This compound was synthesized as a yellowish oil from 17a (21.9 mg, 0.034 mmol), 3x (16.4 mg, 0.051 mmol), K$_2$CO$_3$ (9.3 mg, 0.067 mmol), and 18-Crown-6 (8.9 mg, 0.034 mmol) in 57% yield by following typical procedure B: $^1$H NMR (400 MHz, CDCl$_3$, $\delta$H) 8.22 (s, 1H), 7.90 (s, 1H), 7.64-7.52 (m, 2H), 7.52-7.33 (m, 3H), 7.25 (dd, J=8.5, 1.9 Hz, 1H), 7.05-6.88 (m, 4H), 6.80 (d, J=8.6 Hz, 2H), 4.80 (q, J=14.7 Hz, 2H), 4.46-4.27 (m, 1H), 3.99-3.71 (m, 5H), 3.57-3.42 (m, 1H), 3.43-3.28 (m, 4H), 3.28-3.15 (m, 4H), 1.78 (dt, J=14.7, 7.3 Hz, 2H), 1.44-1.08 (m, 10H), 1.02-0.92 (m, 3H); $^{13}$C NMR (100 MHz, CDCl$_3$, $\delta_C$) 152.84, 152.33, 150.81, 146.19, 136.28, 134.27, 134.16, 133.34, 131.65, 129.83, 127.47, 126.04, 123.80, 118.70, 116.88, 115.49, 107.84, 74.92, 67.86, 67.66, 53.86, 50.81, 49.41, 45.76, 34.47, 29.21, 29.15, 28.78, 26.59, 24.15, 20.11. ESI-MS: 801.3 (M+H$^+$), 823.3 (M+Na$^+$). Purity: 92.9%, $t_R$=10.84 min.

Example 25

4-(4-(4-(4-(((2R,4S)-2-(1H-1,2,4-triazol-1-yl)methyl)-2-(2,4-dichlorophenyl)-1,3-dioxolan-4-yl)methoxy)phenyl)piperazin-1-yl)phenyl)-1H-1,2,4-triazol-5(4H)-one (17a)

Compounds 17a and 17b were prepared according to Scheme 3 (and as described in J. Heeres, L. J. J. B., and J. Van Cutsem (1984). "Antimycotic azoles. 7. Synthesis and antifungal properties of a series of novel triazol-3-ones." J. Med. Chem. 27(4): 894-900).

Scheme 4: Itraconazole Analogs.

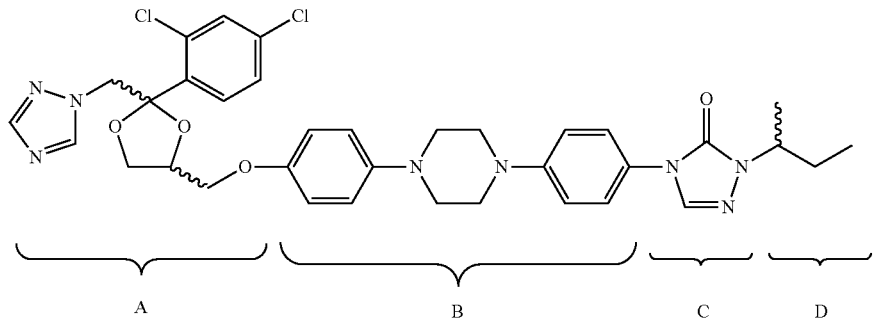

A  B  C  D a)

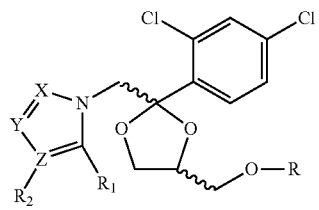

I

1: R₁ = H; X = Y = Z = C;
2: R₁ = CH₃; X = Y = Z = C;
3: R₁ = H; X = N; Y = Z = C;
4: R₁ = CH₃; X = N; Y = Z = C;
5: R₁ = H; X = Y = C; Z = N;
6: R₁ = CH₃; X = Y = C; Z = N;
7: R₁ = H; X = Y = N; Z = C;
8: R₁ = CH₃; X = Y = N; Z = C;
9: R₁ = H; X = C; Y = Z = N;
10: R₁ = CH₃; X = C; Y = Z = N;
11: R₁ = H; X = Y = Z = N;
12: R₁ = CH₃; X = Y = Z = N;
13: R₁ = CH₃; R₂ = H; X = N; Y = C; Z = C;
14: R₁ = H; R₂ = CH₃; X = N; Y = C; Z = C;
15: R₁ = CH₃; R₂ = H; X = C; Y = N; Z = C;
16: R₁ = H; R₂ = CH₃; X = C; Y = N; Z = C;
17: R₁ = CH₃; R₂ = H; X = Y = N; Z = C;
18: R₁ = H; R₂ = CH₃; X = Y = N; Z = C.

b)

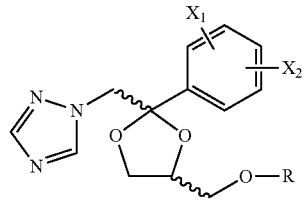

II

19: X₁ = H; : X₂ = H;
20: X₁ = Cl; : X₂ = Cl;
21: X₁ = Cl; : X₂ = H;
22: X₁ = H; : X₂ = Cl;
23: X₁ = F; : X₂ = F;
24: X₁ = H; : X₂ = F;
25: X₁ = F; : X₂ = H;
26: X₁ = F; : X₂ = Cl;
27: X₁ = Cl; : X₂ = F;
28: X₁ = H; : X₂ = CF₃;
29: X₁ = CF₃; : X₂ = H;
30: X₁ = H; : X₂ = Br;
31: X₁ = Br; : X₂ = H.

c)

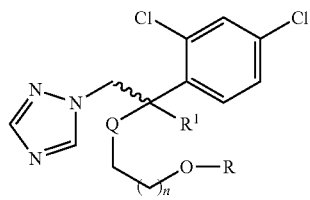

32: R₁ = H; n = 1; Q = O
33: R₁ = H; n = 2; Q = O
34: R₁ = OH; n = 1; Q = O
35: R₁ = OH; n = 2; Q = O
36: R₁ = H; n = 0; Q = C
37: R₁ = H; n = 1; Q = C
38: R₁ = OH; n = 0; Q = C
39: R₁ = OH; n = 1; Q = C

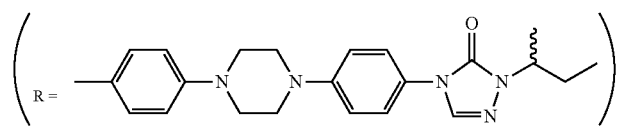

Scheme 5: Synthesis of Itraconazole Analogs.
Synthesis:
Preparation of fragment I, II, III and IV:

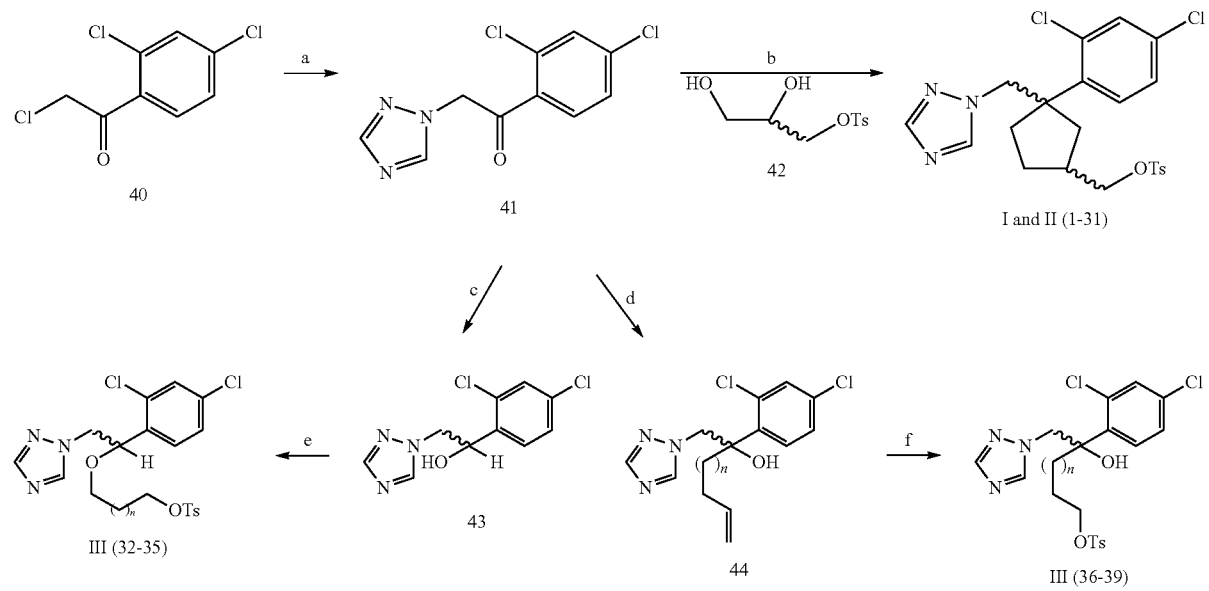

Reagents and conditions: (a) 1H-1,2,4-Triazole, NaHCO₃, NaHCO₃, toluene, reflux. (b) TfOH, toluene, rt. (c) NaBH4, ethanol, 60° C.. (d) Allylzinc, THF.
(e) 2-Bromoethanol, K₂CO₃, DMF, 80° C.; (ii) TsCl, Et₃N, DMAP, CH₂Cl₂. (f) (i) Osmium tetroxide, N-methylmorpholine N-oxide, t-BuOH, THF;
(ii) NaBH₄, THF; (iii) TsCl, Et₃N, DMAP, CH₂Cl₂.

Scheme 6: Synthesis of Itraconazole Analogs.
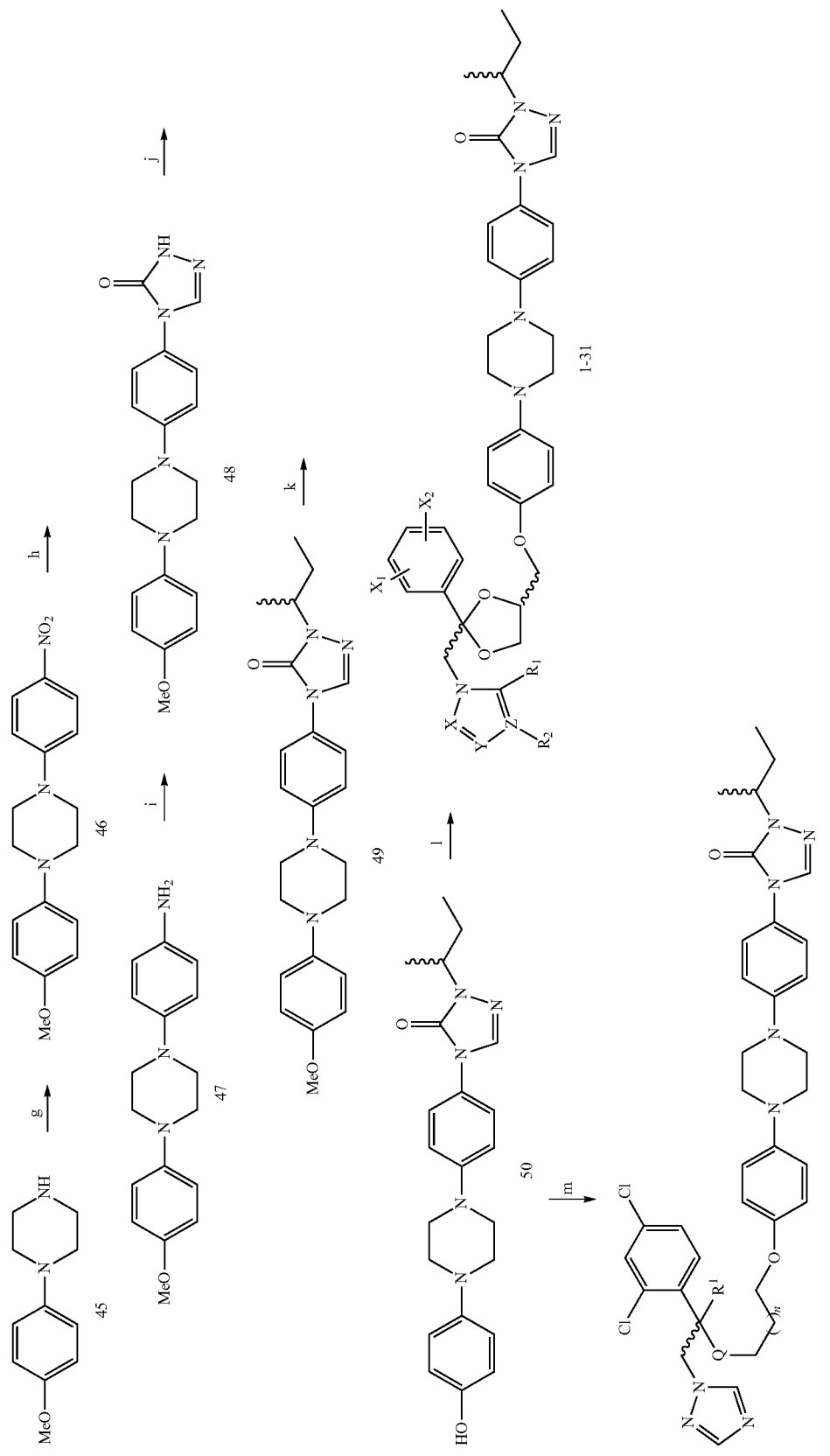
Reagents and conditions: (g) 4-Chloro nitrobenzene, K₂CO₃, DMSO, 160° C. (h) 10% Pd/C, NH₂NH₂·H₂O, EtOH, reflux. (i) (I) Phenylchloro formate, pyridine, CH₃CN; (ii) NH₂NH₂·H₂O, 1,4-dioxane, reflux; (iii) Formamidine acetate, 1-propanol, reflux. (j) 2-Bromo butane, K₂CO₃, DMSO, 80 6 C... (k) 48% Aqueous HBr, 110° C... (i) I or II, NaH, DMSO, 50° C. to 80° C... (m) III, NaH, DMSO, 50° C. to 80° C...

Scheme 7: Itraconazole Analogs.

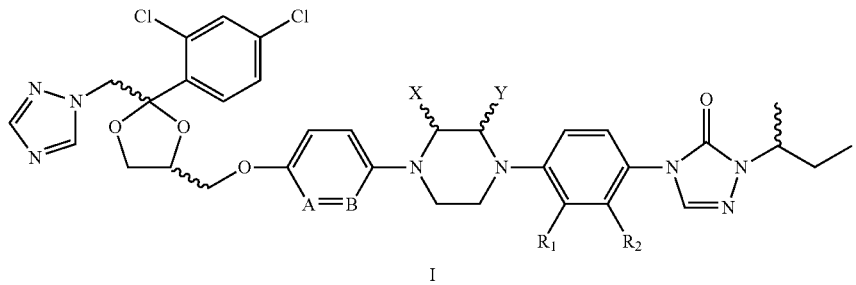

I

A = B = Nitrogen or Carbon
X = Y = Hydrogen or Methyl
R₁ = R₂ = Hydrogen of Fluorine 50: A = N; B = C; R₁ = R₂ = H; X = Y = H;
51: A = N; B = C; R₁ = H; R₂ = F; X = Y = H;
52: A = N; B = C; R₁ = F; R₂ = H; X = Y = H;
53: A = C; B = N; R₁ = R₂ = H; X = Y = H;
54: A = C; B = N; R₁ = H; R₂ = F; X= Y = H;
55: A = C; B = N; R₁ = F; R₂ = H; X = Y = H;
56: A = B = C; R₁ = H; R₂ = F; X = Y = H;
57: A = B = C; R₁ = F; R₂ = H; X = Y = H.

58: A = N; B = C; R₁ = R₂ = H; X = CH₃; Y = H;
59: A = N; B = C; R₁ = H; R₂ = F; X = CH₃; Y = H;
60: A = N; B = C; R₁ = F; R₂ = H; X = CH₃; Y = H;
61: A = C; B = N; R₁ = R₂ = H; X = CH₃; Y = H;
62: A = C; B = N; R₁ = H; R₂ = F; X= CH₃; Y = H;
63: A = C; B = N; R₁ = F; R₂ = H; X = CH₃; Y = H;
64: A = B = C; R₁ = H; R₂ = F; X = CH₃; Y = H;
65: A = B = C; R₁ = F; R₂ = H; X = CH₃; Y = H.

66: A = N; B = C; R₁ = R₂ = H; X = H; Y = CH₃;
67: A = N; B = C; R₁ = H; R₂ = F; X = H; Y = CH₃;
68: A = N; B = C; R₁ = F; R₂ = H; X = H; Y = CH₃;
69: A = C; B = N; R₁ = R₂ = H; X = H; Y = CH₃;
70: A = C; B = N; R₁ = H; R₂ = F; X = H; Y = CH₃;
71: A = C; B = N; R₁ = F; R₂ = H; X = H; Y = CH₃;
72: A = B = C; R₁ = H; R₂ = F; X = H; Y = CH₃;
73: A = B = C; R₁ = F; R₂ = H; X = H; Y = CH₃.

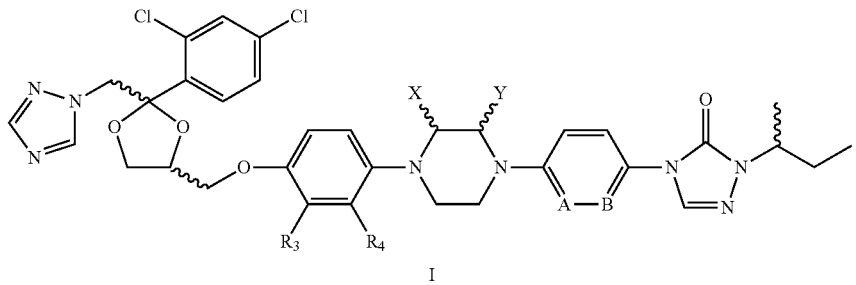

I

A = B = Nitrogen or Carbon
X = Y = Hydrogen or Methyl
R₃ = R₄ = Hydrogen of Fluorine 74: R₃ = R₄ = H; A =N; B = C; X = Y = H;
75: R₃ = R₄ = H; A = C; B = N; X = Y = H;
76: R₃ = H; R₄ = F; A = B = C; X = Y = H;
77: R₃ = H; R₄ = F; A = N; B = C; X = Y = H;
78: R₃ = H; R₄ = F; A = C; B = N; X = Y = H;
79: R₃ = F; R₄ = H; A = B = C; X = Y = H;
80: R₃ = H; R₄ = F; A = N; B = C; X = Y = H;
81: R₃ = H; R₄ = F; A = C; B = N; X = Y = H.

82: R₃ = R₄ = H; A =N; B = C; X = CH₃; Y = H;
83: R₃ = R₄ = H; A = C; B = N; X = CH₃; Y = H;
84: R₃ = H; R₄ = F; A = B = C; X = CH₃; Y = H;
85: R₃ = H; R₄ = F; A = N; B = C; X = CH₃; Y = H;
86: R₃ = H; R₄ = F; A = C; B = N; X = CH₃; Y = H;
87: R₃ = F; R₄ = H; A = B = C; X = CH₃; Y = H;
88: R₃ = H; R₄ = F; A = N; B = C; X = CH₃; Y = H;
89: R₃ = H; R₄ = F; A = C; B = N; X = CH₃; Y = H.

90: R₃ = R₄ = H; A =N; B = C; X = H; Y = CH₃;
91: R₃ = R₄ = H; A = C; B = N; X = H; Y = CH₃;
92: R₃ = H; R₄ = F; A = B = C; X = H; Y = CH₃;
93: R₃ = H; R₄ = F; A = N; B = C; X = H; Y = CH₃;
94: R₃ = H; R₄ = F; A = C; B = N; X = H; Y = CH₃;
95: R₃ = F; R₄ = H; A = B = C; X = H; Y = CH₃;
96: R₃ = H; R₄ = F; A = N; B = C; X = H; Y = CH₃;
97: R₃ = H; R₄ = F; A = C; B = N; X = H; Y = CH₃.

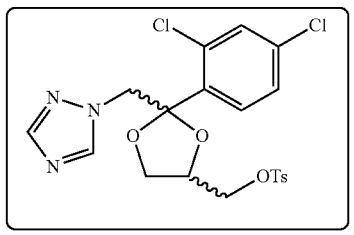

Scheme 8: Preparation of fragment B:
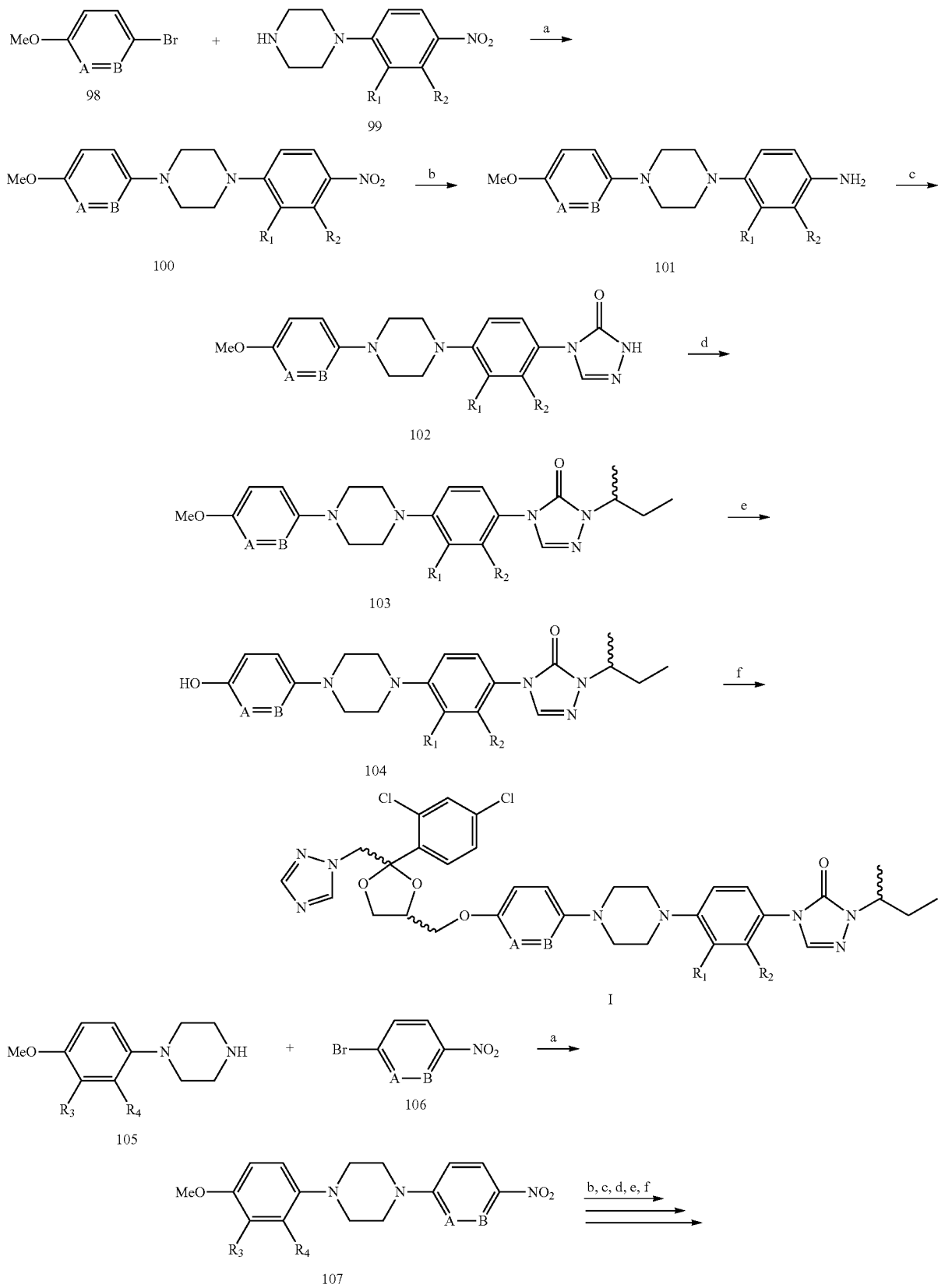

-continued
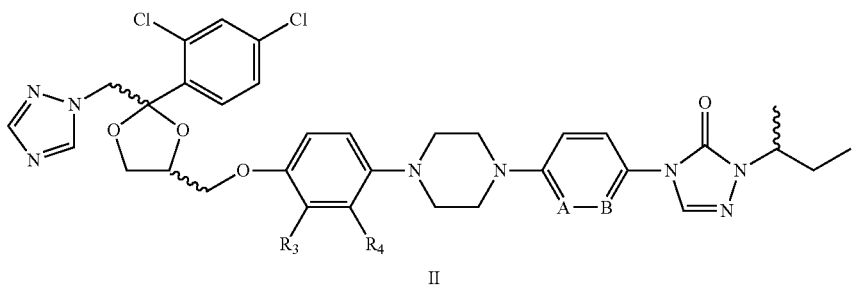
II
Reagents and conditions: (a) Pd$_2$(dba)$_3$, BINAP, NatOBu, toluene, 80° C. (b) 10% Pd/C, NH$_2$NH$_2$, H$_2$O, EtOH, reflux. (c) (i) Phenyl chloroformate, pyridine, CH3CN; (ii) NH$_2$NH$_2$•H$_2$O, 1,4-dioxane, reflux; (iii) Formamidine acetate, 1-propanol, reflux. (d) 2-Bromobutane, K$_2$CO$_3$, DMSO, 80° C. (e) 48% Aqueous HBr, 110° C. (f) 108, NaH, DMSO, 50° C. to 80° C.
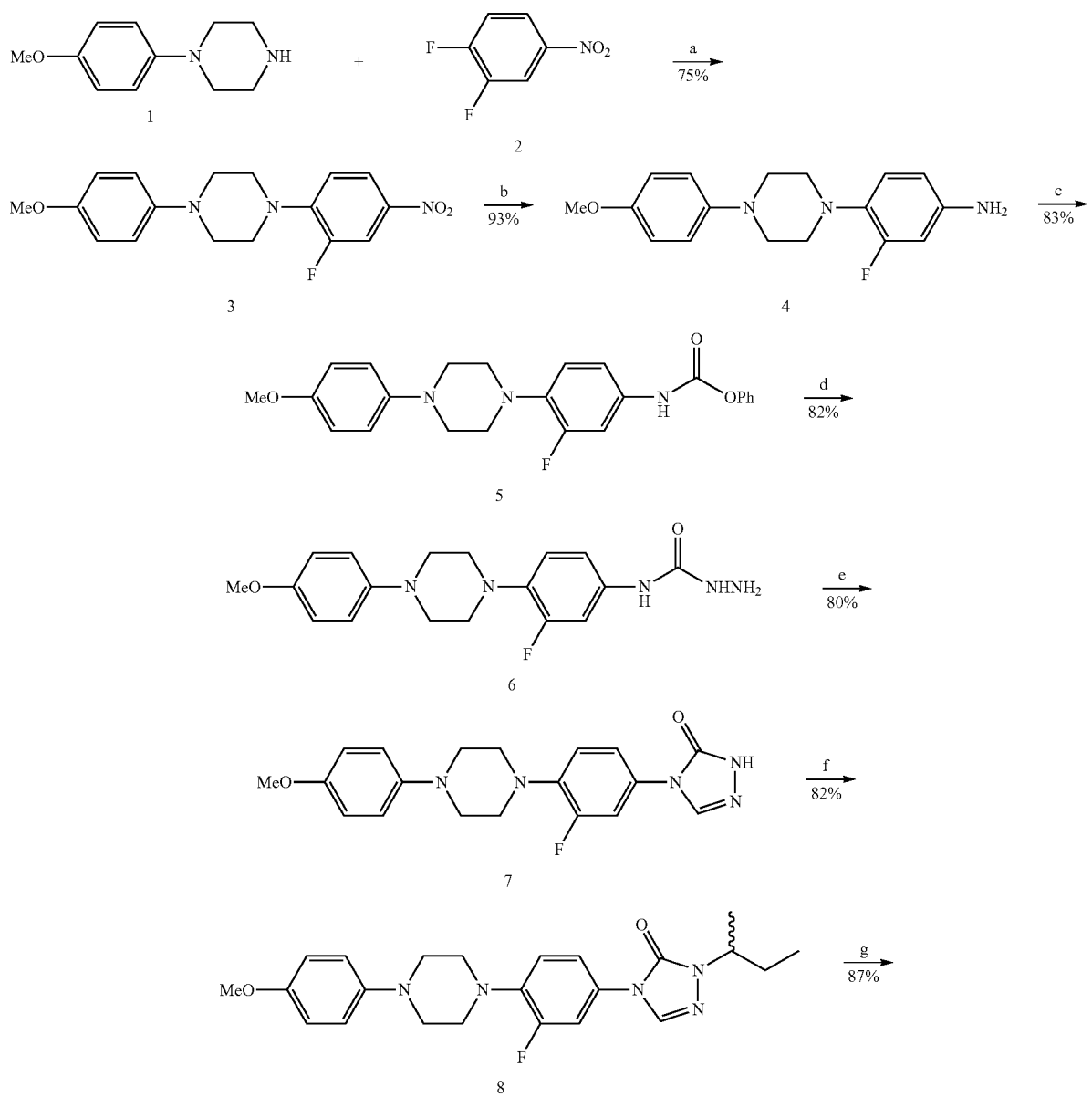

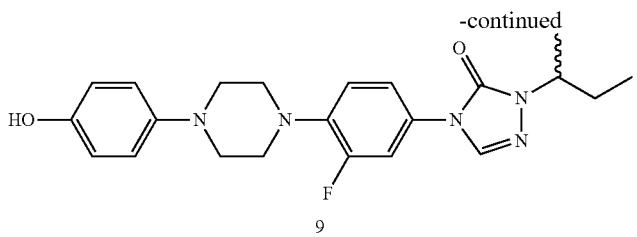

9

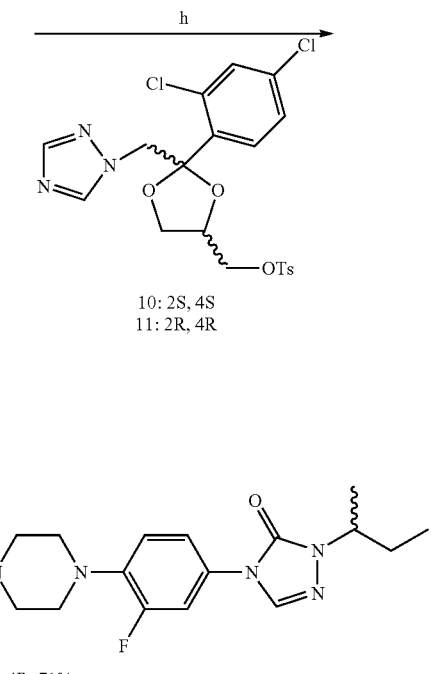

10: 2S, 4S
11: 2R, 4R

12: 2S, 4R, 71%
13: 2R, 4S, 75%

Reagents and conditions: (a) DIPEA, CH$_3$CN, rt, over night (b) 10% Pd/C, NH$_2$NH$_2$, H$_2$O, EtOH, reflux. (c) Phenyl chloroformate, pyridine, CH$_2$CN (d) NH$_2$NH$_2$·H$_2$O, 1,4-dioxane, reflux, (e) Formamidine acetate, 1-proanol, relux. (f) 2-Bromo butane, K$_2$CO$_3$, DMSO, 80° C. (g) 48% Aqueous HBr, 110° C. (h) 10 or 11, NaH, DMSO, 50° C. to 70° C.

1-(2-Fluoro-4-nitrophenyl)-4-(4-methoxyphenyl) piperazine (3)

To a suspension containing 0.16 g of 1,2-difluoro-4-nitrobenzene (2) and 0.28 mL of N-diisopropyl ethylamine (DIPEA) in 4 mL acetonitrile, 0.19 of 1-(4-methoxyphenyl) piperazine (1) was added. The reaction mixture was stirred at room temperature for over night (12 h). The reaction mixture was filtered to get the yellowish solid. Then the collected solid was washed with hexane to get nitro compound 3 (0.25 g, 75%). $^1$H NMR (400 MHz, CDCl$_3$, $\delta_H$): 8.01 (dd, J=8.8, 2.4 Hz, 1H), 7.93 (dd, J=12.8, 2.4 Hz, 1H), 6.99-6.97 (m, 3H), 6.89-6.87 (m, 2H), 3.79 (s, 3H), 3.47 (bs, 4H), 3.26 (d, J=4.8 Hz, 4H). $^{13}$C NMR (100 MHz, CDCl$_3$, $\delta_C$): 154.4, 151.9, 121.0, 118.9, 117.3, 114.6, 112.8, 112.5, 55.6, 51.0, 49.6.

3-Fluoro-4-(4-(4-methoxyphenyl)piperazin-1-yl) aniline (4)

To a stirred suspension of compound 3 (0.2 g, 0.6 mmol) and palladium catalyst (10% Pd on carbon 0.04 g) in ethanol (6 mL), hydrazine monohydrate (0.29 mL, 5.7 mmol) was added slowly and the reaction mixture was heated to reflux for 4 h. After cooling to room temperature, the reaction mixture was filtered and the filtrate was concentrated to obtain amine 4 (0.17 g, 93%).

Phenyl (3-fluoro-4-(4-(4-methoxyphenyl)piperazin-1-yl)phenyl)carbamate (5)

To a solution of 4 (0.32 g, 1 mmol) and pyridine (0.12 mL, 1.5 mmol) in acetonitrile (4 mL, 0.25M), phenyl chloroformate (0.16 mL, 1.2 mmol) was added at 0° C. and the reaction mixture was stirred at room temperature for overnight. Then water was added and the mixture was stirred for 30 min. The precipitated white solid was filtered and the solid was washed with acetonitrile and then dried under vacuum to obtain compound 5 (0.35 g, 83%).

N-(3-fluoro-4-(4-(4-methoxyphenyl)piperazin-1-yl) phenyl)hydrazinecarboxamide (6)

To a solution containing 5 (0.3 g, 0.7 mmol) and hydrazine monohydride (0.19 mL, 3.7 mmol) in 1,4-dioxane. The reaction mixture was stirred and heated to reflux for 4 h. After cooling to room temperature water was added and the mixture was stirred for 30 min. The precipitated solid was filtered and the solid was washed with acetonitrile and then dried under vacuum to obtain the hydrazinecarboxamide intermediate 6 (0.2 g, 82%).

4-(3-fluoro-4-(4-(4-methoxyphenyl)piperazin-1-yl) phenyl)-1H-1,2,4-triazol-5(4H)-one (7)

The mixture of hydrazinecarboxamide 7 (0.15 g, 0.4 mmol) and formamidine acetate (0.27 g, 2.8 mmol) in 1-propanol (4 mL, 0.1M) was heated to reflux for 3 h. After cooling to room temperature, the reaction mixture was diluted with water. The solid was filtered, washed with 50% aqueous 1-propanol, and then dried under vacuum to obtain 7 (0.11 g, 80%) as an off-white solid.

1-(sec-butyl)-4-(3-fluoro-4-(4-(4-methoxyphenyl) piperazin-1-yl)phenyl)-1H-1,2,4-triazol-5(4H)-one (8)

To a suspension of triazolone 7 (0.11 g, 0.3 mmol) in dimethylsulfoxide (4 mL) was added K$_2$CO$_3$ (0.08 g, 0.6 mmol). The resulting mixture was stirred at room temperature for 1 h. After the addition of 2-bromo butane (0.05 mL, 0.45 mmol), the temperature increased to 80° C. for overnight. After cooling to room temperature, the reaction mixture was diluted with water and extracted with dichlormethane. The combined organic layer was dried over Na$_2$SO$_4$, filtered, and concentrated to yield the crude product, which was purified by column chromatography to obtain triazolone 8 (0.11 g, 87%). $^1$H NMR (400 MHz, CDCl$_3$, δ$_H$): 7.64 (s, 1H), 7.37 (dd, J=13.0, 2.2 Hz, 1H), 7.26-7.24 (m, 1H), 7.04 (t, J=8.8 Hz, 1H), 6.99-6.97 (m, 2H), 6.88-6.84 (m, 2H), 4.31-4.26 (m, 1H), 3.77 (s, 3H), 3.26 (bs, 8H), 1.86-1.81 (m, 1H), 1.73-1.71 (m, 1H), 1.38 (d, J=6.8 Hz, 3H), 0.89 (t, J=7.4 Hz, 3H). $^{13}$C NMR (100 MHz, CDCl$_3$, δ$_C$): 154.6, 154.2, 151.6, 139.4, 133.3, 128.4, 119.4, 118.7, 118.0, 114.5, 111.0, 110.8, 55.6, 52.8, 51.0, 50.5, 28.4, 19.3, 10.8.

1-(sec-butyl)-4-(3-fluoro-4-(4-(4-hydroxyphenyl)piperazin-1-yl)phenyl)-1H-1,2,4-triazol-5(4H)-one (9)

Triazolone 8 (0.1 g, 0.23 mmol) was added to aqueous HBr (48%, 1.9 mL). The reaction was heated to 120° C. and refluxed overnight. The reaction mixture was cooled to room temperature and the solution was neutralized with saturated Na$_2$CO$_3$ and extracted with dichloromethane (DCM). The combined organic layer was dried (Na$_2$SO$_4$), filtered, and concentrated to yield the product, which was purified by column chromatography to obtain compound 9 (0.08 g, 83%). $^1$H NMR (400 MHz, CDCl$_3$, δ$_H$): 7.57 (s, 1H), 7.24 (dd, J=10.2, 2.0 Hz, 1H), 7.15 (dd, J=6.8, 1.6 Hz, 1H), 6.92 (t, J=7.0 Hz, 1H), 6.79 (d, J=6.8 Hz, 2H), 6.67 (d, J=7.2 Hz, 2H), 4.24-4.20 (m, 1H), 3.17-3.16 (m, 8H), 1.82-1.77 (m, 1H), 1.66-1.63 (m, 1H), 1.32 (d, J=5.6 Hz, 3H), 0.82 (t, J=5.8 Hz, 3H). $^{13}$C NMR (100 MHz, CDCl$_3$, δ$_C$): 156.3, 154.3, 150.8, 144.9, 139.7, 133.6, 127.8, 119.4, 118.9, 116.0, 111.4, 53.1, 51.2, 50.5, 28.4, 19.3, 10.8.

General experimental procedure for the preparation of 12 or 13

To a solution of 9 in DMSO was added NaH (60% dispersion in mineral oil) and the temperature increased to 50° C. under argon for 1 h. A solution of 10 or 11 in DMSO was added drop wise and the temperature was increased to 70° C. and stirred for 3 h. After cooling to room temperature, the reaction mixture was quenched with 50% aqueous NaCl solution and the reaction mixture was diluted in water. The aqueous solution was extracted with DCM, the organic layer was dried over Na$_2$SO$_4$, which was purified by column chromatography.

Scheme 10: Itraconazole Analogs and Synthesis Thereof.

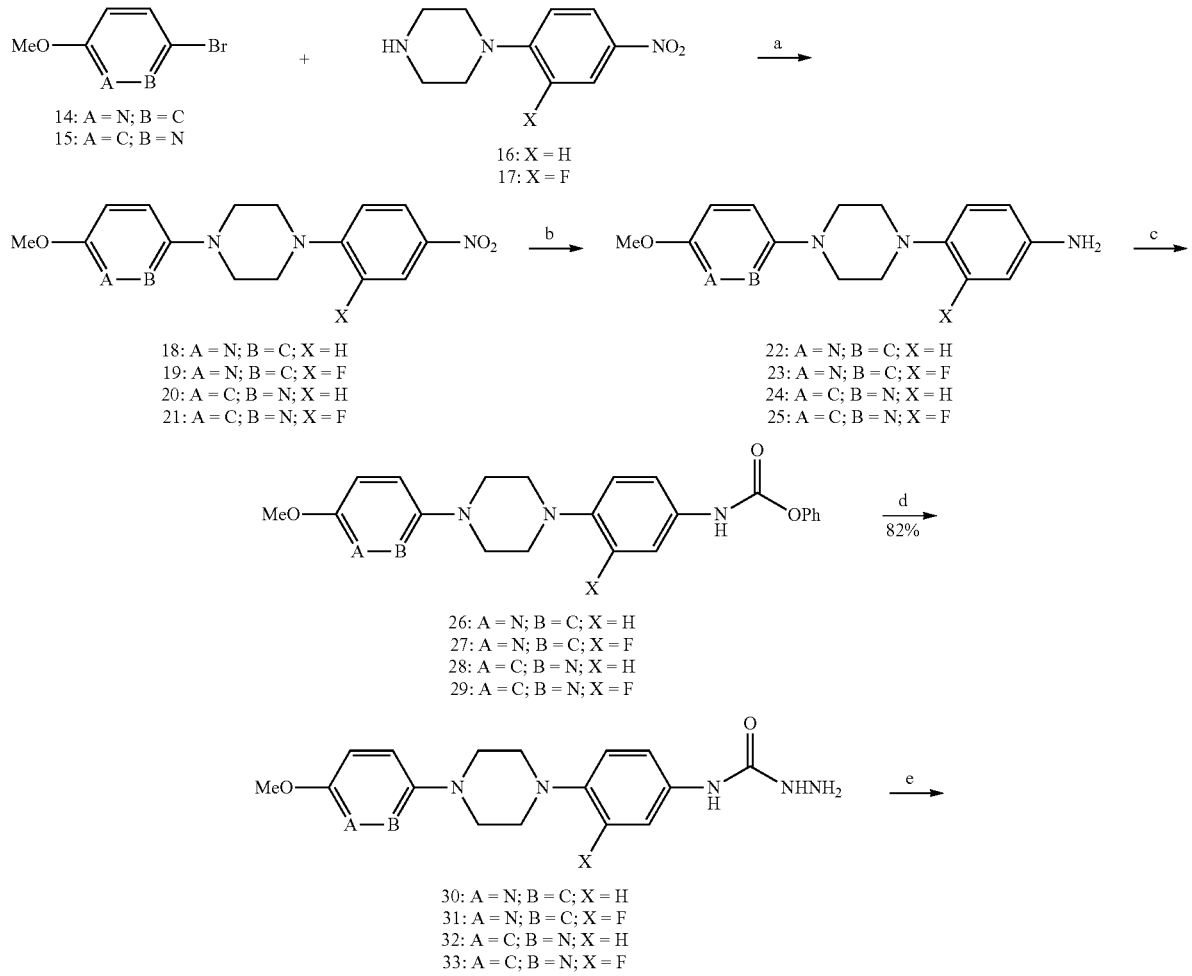

-continued

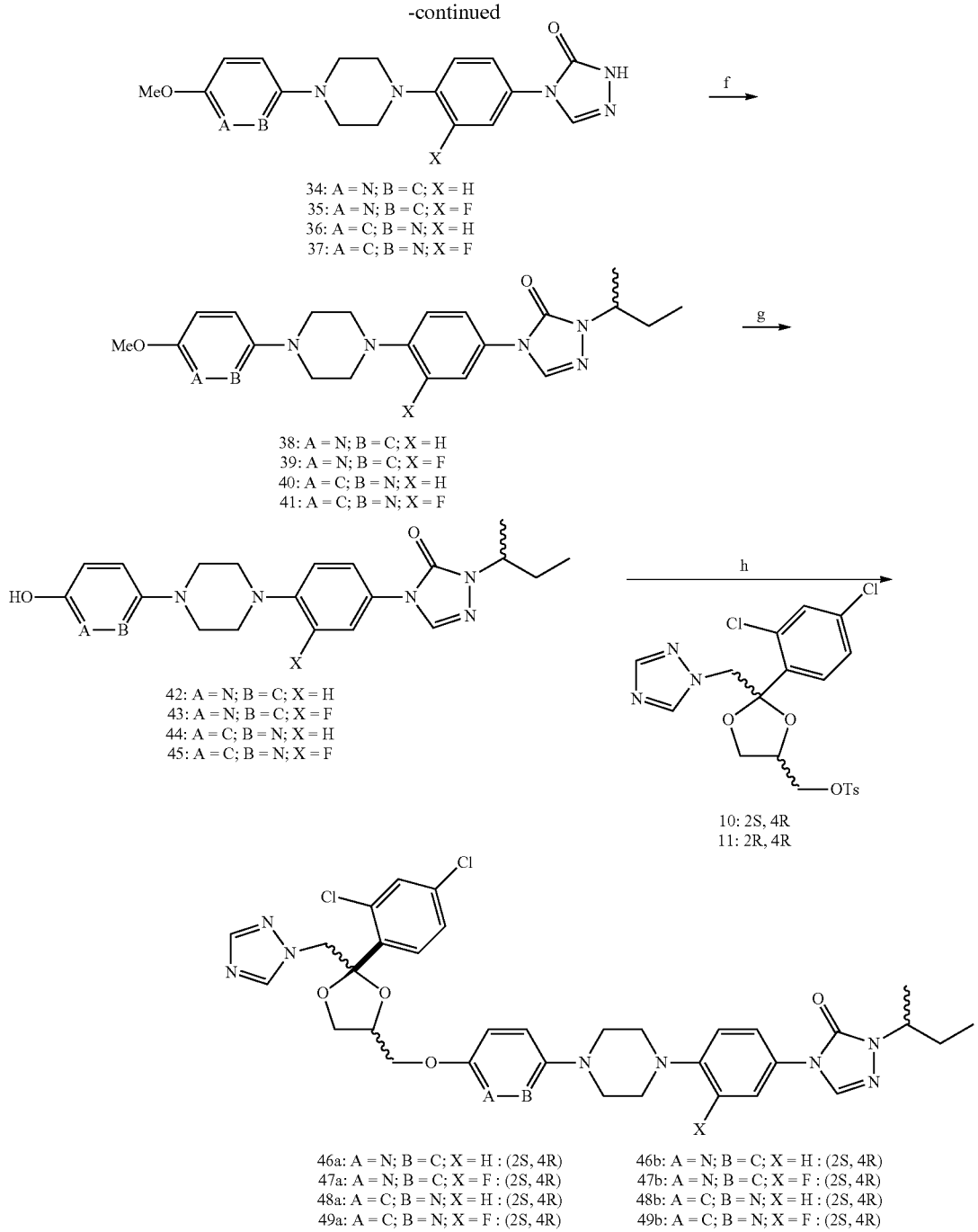

34: A = N; B = C; X = H
35: A = N; B = C; X = F
36: A = C; B = N; X = H
37: A = C; B = N; X = F

38: A = N; B = C; X = H
39: A = N; B = C; X = F
40: A = C; B = N; X = H
41: A = C; B = N; X = F

42: A = N; B = C; X = H
43: A = N; B = C; X = F
44: A = C; B = N; X = H
45: A = C; B = N; X = F

10: 2S, 4R
11: 2R, 4R

46a: A = N; B = C; X = H : (2S, 4R)      46b: A = N; B = C; X = H : (2S, 4R)
47a: A = N; B = C; X = F : (2S, 4R)      47b: A = N; B = C; X = F : (2S, 4R)
48a: A = C; B = N; X = H : (2S, 4R)      48b: A = C; B = N; X = H : (2S, 4R)
49a: A = C; B = N; X = F : (2S, 4R)      49b: A = C; B = N; X = F : (2S, 4R)

Reagents and conditions: (a) $Pd_2(dba)_3$, BINAP, $Na^tOBu$, toluene, 80° C., over night (b) 10% Pd/C, $NH_2NH_2 \cdot H_2O$, EtOH, reflux. (c) Phenl chloroformate, pyridine, $CH_3CN$. (d) $NH_2NH_2 \cdot H_2O$, 1,4-dioxane, reflux. (e) Formamidine acetate, 1-propanol, reflux; (f) 2-Bromo butane, $K_2CO_3$, DMSO, 80° C. (g) 48% Aqueous HBr, 110° C. (h) 10 or 11, NaH, DMSO, 50° C. to 70° C.

General experimental procedure for the preparation of 18-21

The mixture of compounds 14 or 15, 16 or 17, $Pd_2(dba)_3$, t-BuONa, and rac-BINAP in dry toluene was stirred overnight at 80° C. under argon atmosphere. After cooling to room temperature, the reaction mixture was diluted in water and the resulting solid was filtered. The aqueous solution was extracted with DCM, the organic layer was dried over $Na_2SO_4$, which was purified by column chromatography.

The synthetic methods for the following compounds 22-25 were similar to the synthesis of compound 4.

The synthetic methods for the following compounds 26-29 were similar to the synthesis of compound 5.

The synthetic methods for the following compounds 30-33 were similar to the synthesis of compound 6.

The synthetic methods for the following compounds 34-37 were similar to the synthesis of compound 7.

The synthetic methods for the following compounds 38-41 were similar to the synthesis of compound 8.

The synthetic methods for the following compounds 42-45 were similar to the synthesis of compound 9.

The synthetic methods for the following compounds 46a-49b and 46a-49b were similar to the synthesis of compound 12 or 13.

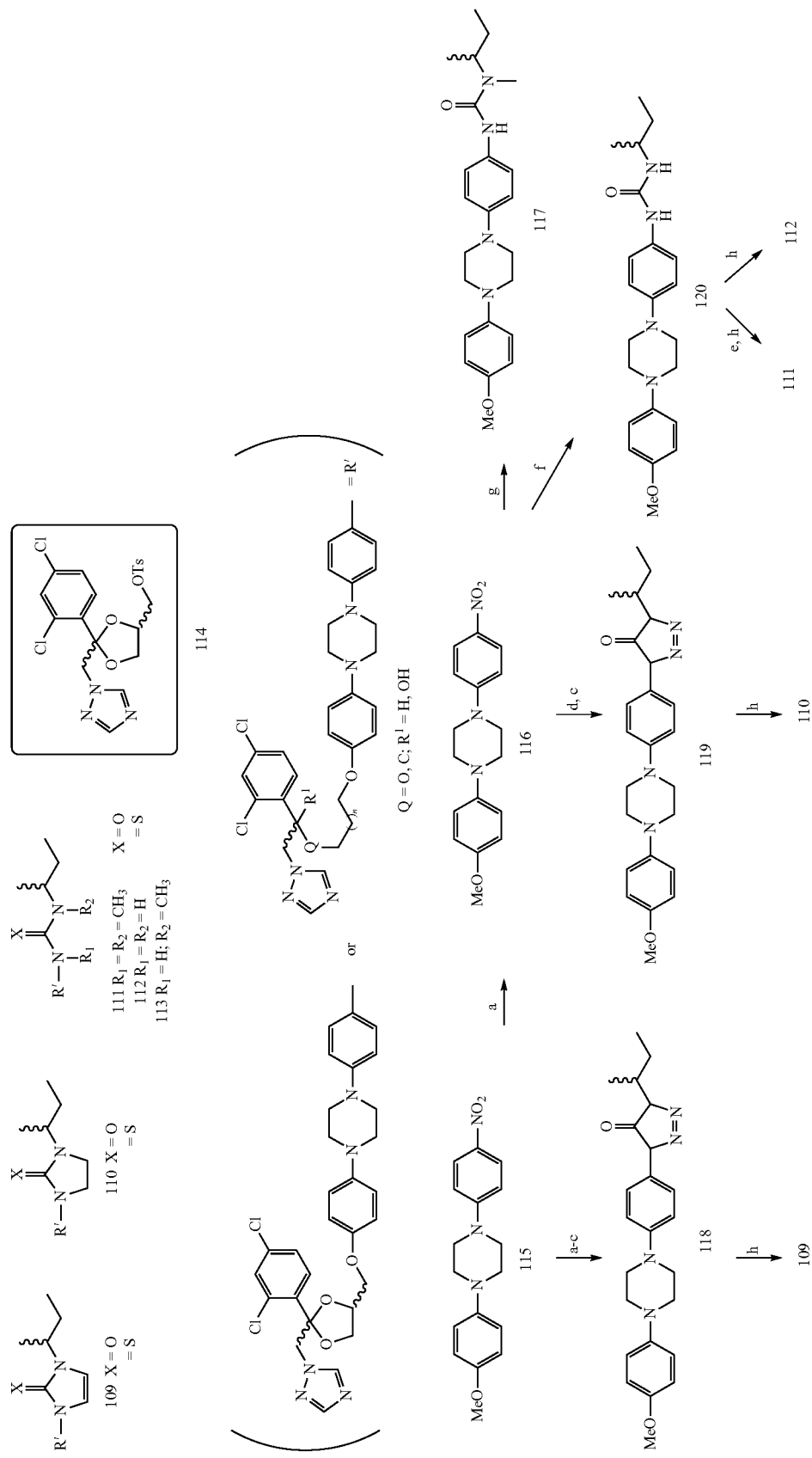

The biological activity of the compounds in Examples 1-24 is illustrated in the following assays. The other compounds listed above, which have not yet been made and/or tested, are predicted to have activity in these assays as well.

Biological Activity Assay

HUVEC Culture and Proliferation Assays

Pooled HUVEC (Lonza) were grown in EGM-2 bullet kit media (Lonza) and used at passage eight or lower. The proliferation assays were conducted as previously described (Nacev, B.; Low, W. K.; Huang, Z.; Su, T.; Su, Z.; Alkuraya, H.; Kasuga, D.; Sun, W.; Trager, M.; Braun, M.; Fischer, G.; Zhang, K.; Liu, J. O., A calcineurin-independent mechanism of angiogenesis inhibition by a non-immunosuppressive Cyclosporin A analog. J. Pharmacol. Exp. Ther. 2011, DOI: 10.1124/jpet.111.18085).

TABLE 5

Itraconazole analogs & Their Activity in HUVEC Proliferation ($IC_{50}$).

| No. | Compound | Structure | $IC_{50}$ (nM) |
|---|---|---|---|
| 1 | Itraconazole (Standard) | 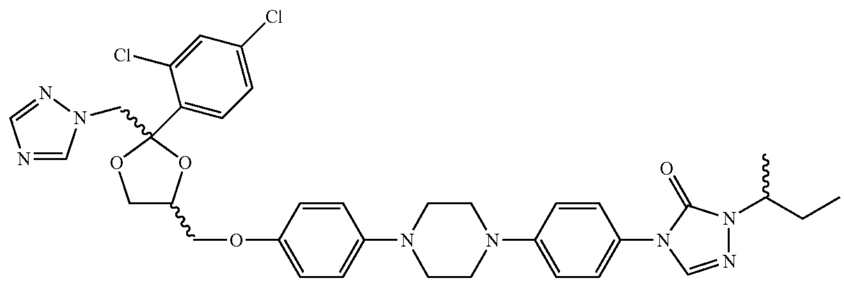 [SMILES: CC[C@@H](C)n1ncn(-c2ccc(N3CCN(c4ccc(OC[C@@H]5CO[C@@](Cn6cncn6)(c6ccc(Cl)cc6Cl)O5)cc4)CC3)cc2)c1=O] | 180.5 |
| 2 | Itraconazole A (2S, 4R, 2'S) | 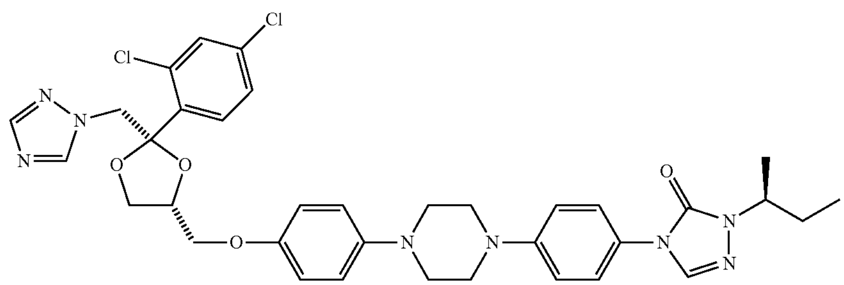 | 167.3 |
| 3 | Itraconazole C (2S, 4R, 2'R) | 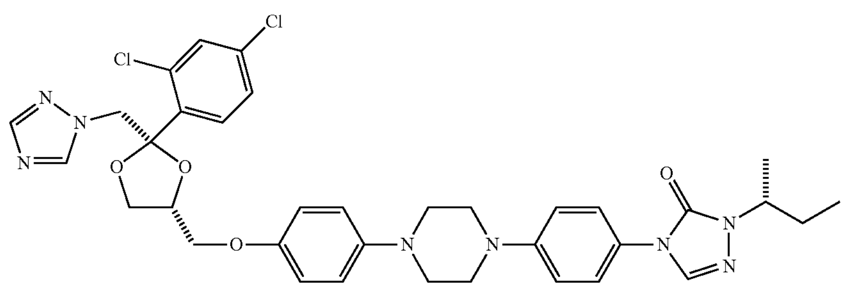 | 151.9 |
| 4 | 13 | 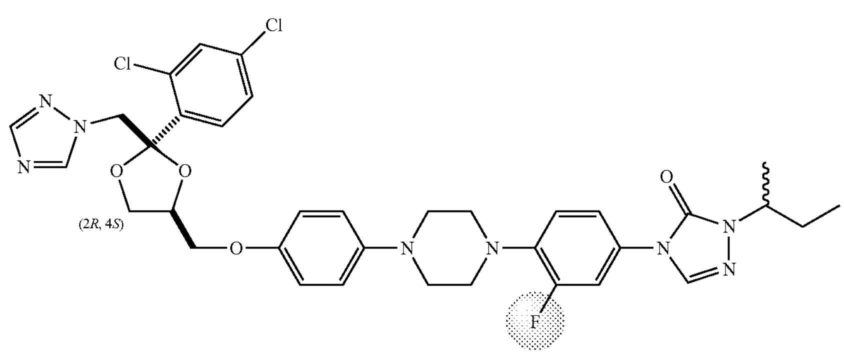 | 419.0 |

TABLE 5-continued

Itraconazole analogs & Their Activity in HUVEC Proliferation (IC$_{50}$).

| No. | Compound | Structure | IC$_{50}$ (nM) |
|---|---|---|---|
| 5 | 12 | 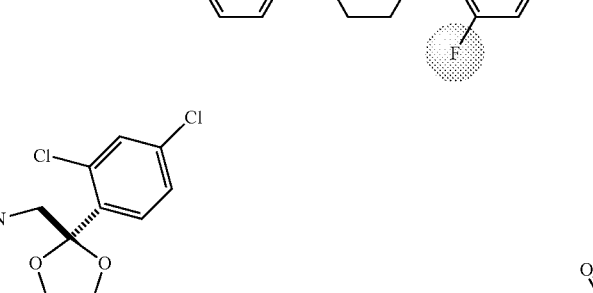 (2S, 4R) | 235.9 |
| 6 | 46b | 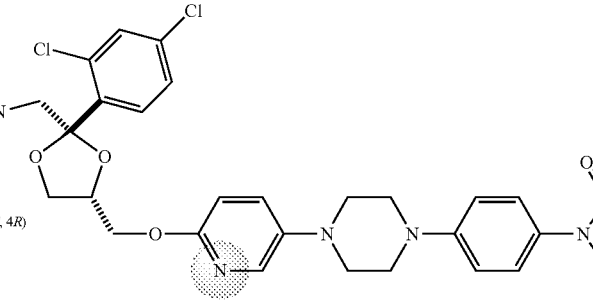 (2R, 4S) | 235.9 |
| 7 | 46a | 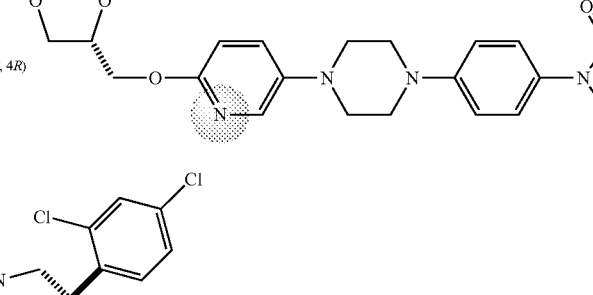 (2S, 4R) | 154.9 |
| 8 | 47a | 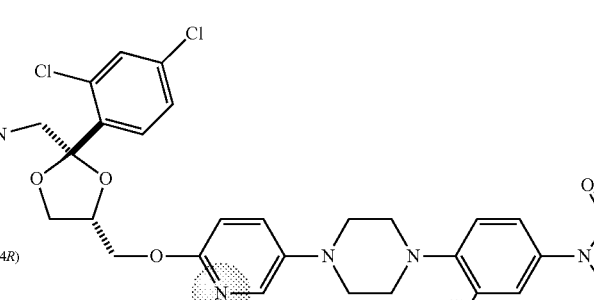 (2S, 4R) | 154.8 |

VEGFR2 Glycosylation

HUVEC were seeded at 5×10$^4$ per well of a 6-well plate in 3 mL of media. After an overnight recovery, the media was replaced with 2 mL fresh media and the analogs were added from 200× stocks in DMSO. Following a 24-h incubation, the media was aspirated and 2×SDS sample buffer was added to the cells which were incubated on ice for 10 min and then boiled for 10 min. The lysate was then subjected to 6% SDS-PAGE and transferred to PVDF (Bio-Rad) membranes which were subsequently blocked in 5% BSA (Sigma) in TBS-T (10 mM Tris pH 8.0, 150 mM NaCl, 0.05 Tween 20 [Sigma]) and then incubated with 1% anti-VEGFR2 in 1% BSA in TBS-T (cell signaling #2749). Following three washes in TBS-T, the membrane was incubated with anti-rabbit horseradish peroxidase conjugated IgG (GE Healthcare) (1:5000-1:10000 dilution) in 1% BSA in TBS-T. The membranes were washed three times in TBS-T, incubated for 1-5 minutes with ECL substrate (Immobilon Wester, Milipore) and visualized (Kodak Image Staion 440 CF).

Medulloblastoma Culture

Figure 9:
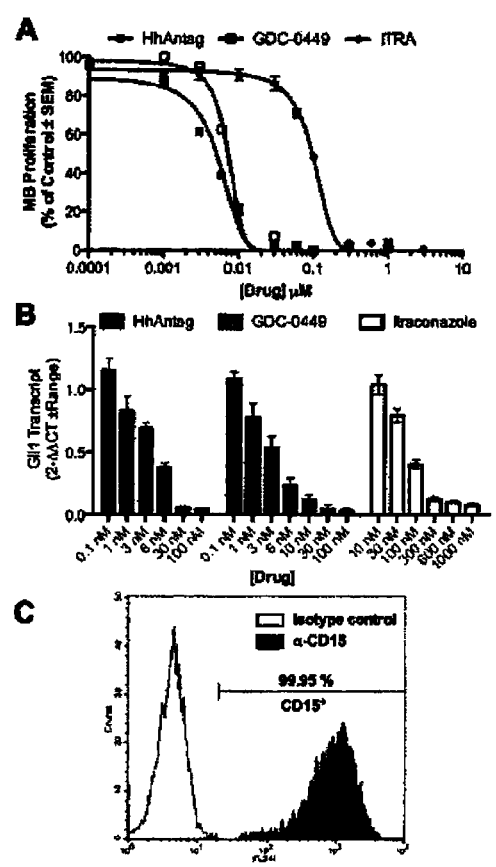
FIG. 9 is a graphic representation of validation and characterization by Smo inhibitor activity on proliferation and Hh pathway activation and enrichment of CD15 expressing cells in MB cultures. A. Dose-dependent inhibition of MB proliferation by HhAntag (■), GDC-0449 (□), and Itraconazole (●). B. Dose-dependent inhibition of Gli1 transcript levels by HhAntag (■), GDC-0449 (■), and Itraconazole (□) in established MB cultures is coupled to inhibition of MB proliferation. C. Flow cytometric analysis of CD15 expression in MB cultures; white=isotype control, black=α-CD15.

MB cultures were derived from mouse Ptch$^{-/-}$; p53$^{-/-}$ MB grown as hind-flank allografts in nude mice (Harlan). Briefly, tumors were mechanically disrupted and made into single cell suspensions by two passages through a 70 μm nylon filter. Cells were pelleted by centrifugation and resuspended in PBS pH 7.4 twice. The cell suspension was then subjected to centrifugation at 1000×g for 25 min over a ficoll gradient. The viable cell layer formed at the ficoll boundary was then collected, suspended in PBS, and pelleted by centrifugation. The resulting pellet was then suspended and cultured as "neurospheres" in Neurobasal Media-A supplemented with retinoic acid deficient B-27 extract (NBMedia). Cells were cultured for three passages, with neurospheres disaggregated using Accumax (Innovative Cell Technologies) between passages. Prior to assaying, CD 15 expression was confirmed by flow cytometric analysis. Inhibition of proliferation and Gli transcription was also confirmed in response to HhAntag and GDC-0449 (FIG. 9).

Medulloblastoma Proliferation Assay

Cultured MB neurospheres were disaggregated as described and 1×10$^4$ cells were seeded into wells of a 96-well assay plate in NBMedia and exposed to multiple analogue concentrations. Relative cell numbers following a 96-h incubation were quantified by CeliTiter 96® AQ$_{ueous}$ One Solution Cell Proliferation Assay (Promega) per manufacturer's recommendations using a SpectraMax M2e spectrophotometer and SoftMax Pro software (Molecular Devices). Data was analyzed using Prism5 (GraphPad Software) and IC$_{50}$ and IC$_{90}$ values were determined from dose-response curves fitted to mean corrected absorbance normalized to control treatment.

Quantification of Gli1 Transcript by TaqMan Analysis.

MB neurospheres were cultured in NBMedia to confluence in 25 cm$^3$ culture flasks and exposed for 24 h to analogs at the experimentally determined IC$_{90}$ for proliferation. Following drug exposure, cells were washed in PBS and pelleted by centrifugation at 300×g. Cell pellets were lysed in Trizol reagent (Invitrogen). Total RNA was separated and collected in the aqueous phase following centrifugation of lysate in the presence of chloroform. Total RNA was ethanol precipitated and purified over RNeasy Mini Kit (Qiagen) filter columns per manufacturer's recommendations. Transcript levels were quantified using gene-specific TaqMan primer/probe sets and the StepOne Plus Real-Time PCR system (Applied Biosystems) on cDNA reverse transcribed using the QuantiTect Reverse Transcription Kit (Qiagen) per manufacturers' recommendations. Results were quantified using StepOne Plus software v2.1 (Applied Biosystems) and were expressed as fold induction relative to control samples using the ΔΔCt ($2^{-\Delta\Delta Ct}$) method with actin as an internal control. The primer/probe set (Applied Biosystems) for TaqMan PCR for mouse Gli-1 was Mm00494645_ml, and for mouse actin was Mm00607939_sl. Fold induction values for Gli1 transcript at the IC$_{90}$ for MB proliferation were scored on a three-point semi-quantitative scale as follows: ++, ≤0.15; +, 0.16 to 0.44; −, ≥0.45.

Although the invention has been described with reference to the above example, it will be understood that modifications and variations are encompassed within the spirit and scope of the invention. Accordingly, the invention is limited only by the following claims.

What is claimed is:

1. A compound of structural Formula (IV):

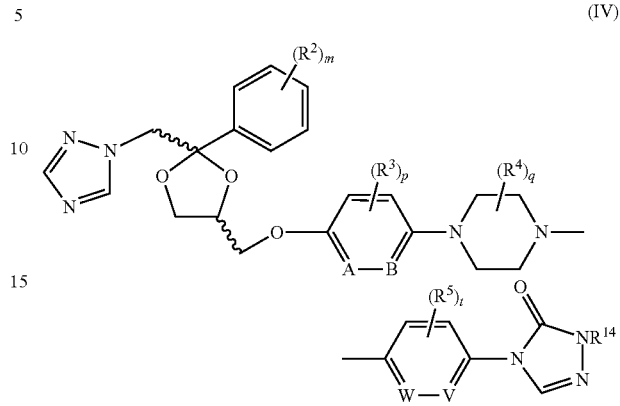

(IV)

or an optically pure stereoisomer or pharmaceutically acceptable salt thereof, wherein:

A is CR$^6$ or N;
B is CR$^7$ or N;
W is CR$^8$;
V is CR$^9$;
each R$^2$, R$^3$, and R$^4$ are independently chosen from the group consisting of alkoxy, alkyl, amino, halogen, hydroxyl, haloalkyl, perhaloalkyl, perhaloalkoxy, nitro, and cyano;
R$^6$, R$^7$, R$^8$, and R$^9$ are each independently chosen from the group consisting of hydrogen, and halogen;
p is an integer between 0 and 2;
m is an integer between 0 and 4;
q is 0; and
R$^{14}$ is chosen from the group consisting of hydrogen, alkyl, arylalkyl, alkoxyalkyl, arylalkoxy, alkynylalkyl, alkenylalkyl, cycloalkyl, cyanoalkyl, and cycloalkylalkyl,
wherein at least one of A or B is N, and further wherein A and B are not both simultaneously N, wherein:
each R5 is independently halogen; and
t is 1 or 2.
2. The compound of claim 1, wherein:
m is 2; and
each R$^2$ is independently chlorine.
3. The compound of claim 2, wherein R$^{14}$ is

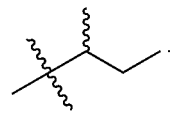 [SMILES: *C(C)CC]

4. The compound of claim 1, wherein p is 0.
5. The compound of claim 1, wherein A is CR$^6$.
6. The compound of claim 5, wherein B is N.
7. The compound of claim 1, wherein A is N.
8. The compound of claim 7, wherein B is CR$^7$.
9. The compound of claim 8, wherein R$^7$ is hydrogen.
10. The compound of claim 8, wherein p is 0.
11. The compound of claim 8, wherein m is 2.
12. The compound of claim 11, wherein R$^2$ is halogen.
13. The compound of claim 8, wherein R$^9$ is hydrogen.
14. The compound of claim 13, wherein R$^8$ is halogen.
15. A pharmaceutical composition comprising the compound of claim 1 together with a pharmaceutically acceptable carrier.

* * * * *